US011136310B2

(12) United States Patent
Charlton et al.

(10) Patent No.: US 11,136,310 B2
(45) Date of Patent: Oct. 5, 2021

(54) IMINOTETRAHYDROPYRIMIDINONE DERIVATIVES AS PLASMEPSIN V INHIBITORS

(71) Applicant: UCB Biopharma SPRL, Brussels (BE)

(72) Inventors: Rebecca Louise Charlton, Durham (GB); Teresa De Haro Garcia, Slough (GB); Martin Alexander Lowe, Slough (GB); Malcolm Maccoss, Seabrook Island, SC (US); Trevor Morgan, Garden City (GB); Richard David Taylor, Slough (GB); Zhaoning Zhu, Slough (GB)

(73) Assignee: UCB Biopharma SRL, Brussels (BE)

( * ) Notice: Subject to any disclaimer, the term of this patent is extended or adjusted under 35 U.S.C. 154(b) by 45 days.

(21) Appl. No.: 15/774,332

(22) PCT Filed: Nov. 24, 2016

(86) PCT No.: PCT/EP2016/078664
§ 371 (c)(1),
(2) Date: May 8, 2018

(87) PCT Pub. No.: WO2017/089453
PCT Pub. Date: Jun. 1, 2017

(65) Prior Publication Data
US 2020/0283416 A1    Sep. 10, 2020

(30) Foreign Application Priority Data

Nov. 25, 2015 (GB) ...................................... 1520808
Jul. 26, 2016 (GB) ...................................... 1612944

(51) Int. Cl.
*C07D 403/10* (2006.01)
*C07D 417/10* (2006.01)
*C07D 471/04* (2006.01)

(52) U.S. Cl.
CPC ......... *C07D 403/10* (2013.01); *C07D 417/10* (2013.01); *C07D 471/04* (2013.01)

(58) Field of Classification Search
CPC ..... A61P 33/06; C07D 401/10; C07D 403/10; C07D 417/10; C07D 471/04
See application file for complete search history.

(56) References Cited

U.S. PATENT DOCUMENTS

2009/0062282 A1* 3/2009 Albert .................... A61P 25/16
514/235.8

FOREIGN PATENT DOCUMENTS

| JP | 2008-516946 A | 5/2008 |
| WO | WO2006/041405 | 4/2006 |
| WO | 2007/073284 | 6/2007 |
| WO | 2007/146225 | 12/2007 |
| WO | 2008/103351 | 8/2008 |

OTHER PUBLICATIONS

Stamford et al., "Discovery of an Orally Available, Brain Penetrant BACE1 Inhibitor That Affords Robust CNS A-beta Reduction," ACS Medicinal Chemtry Letters, vol. 3, Jul. 12, 2012, pp. 897-902.
Japanese Office Action for Japanese Patent Application JP 2018-526893 dated Sep. 24, 2020, 7 pages.

* cited by examiner

*Primary Examiner* — Umamaheswari Ramachandran
(74) *Attorney, Agent, or Firm* — McDonnell Boehnen Hulbert & Berghoff LLP

(57) ABSTRACT

A series of 2-imino-6-methyltetrahydropyrimidin-4(1H)-one derivatives, substituted in the 6-position by a phenyl moiety which in turn is meta-substituted by an optionally substituted unsaturated fused bicyclic ring system containing at least one nitrogen atom, being selective inhibitors of plasmepsin V activity, are beneficial as pharmaceutical agents, especially in the treatment of malaria.

10 Claims, No Drawings

IMINOTETRAHYDROPYRIMIDINONE DERIVATIVES AS PLASMEPSIN V INHIBITORS

This application is a U.S. national phase application under 35 USC 371 of International Patent Application no. PCT/EP2016/078664, filed Nov. 24, 2016, which claims the benefit of Great Britain application no. 1520808.5, filed Nov. 25, 2015, and of Great Britain application no. 1612944.7, filed Jul. 26, 2016.

The present invention relates to a class of heterocyclic compounds, and to their use in therapy. More particularly, this invention is concerned with pharmacologically active substituted iminotetrahydropyrimidinone derivatives. These compounds are potent and selective inhibitors of plasmepsin V activity, and are accordingly of benefit as pharmaceutical agents, especially in the treatment of malaria.

Malaria is a mosquito-borne infectious disease, caused by a parasite of the genus *Plasmodium*, which has devastating consequences. In 2010, an estimated 225 million cases were reported, with 610,000 to 971,000 deaths, approximately 80% of which occurred in sub-Saharan Africa, mostly in young children (aged 5 years or less).

The aspartyl protease, plasmepsin V, is reported to be essential for the viability of the *Plasmodium falciparum*: parasite and has accordingly been proposed as representing an attractive target enzyme for the discovery of antimalarial medicines (cf. I. Russo et al., *Nature*, 2010, 463, 632-636; and B. E. Sleebs et al., *J. Med. Chem.*, 2014, 57, 7644-7662).

The compounds in accordance with the present invention, being potent and selective inhibitors of plasmepsin V activity, are therefore beneficial in the treatment of malaria.

In addition, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2008/103351, WO 2006/065277 and WO 2005/058311 describe a family of heterocyclic compounds that are stated to be aspartyl protease inhibitors. The compounds described in those publications are also stated to be effective in a method of inhibiting inter alia plasmepsins (specifically plasmepsins I and II) for treatment of malaria. However, there is no explicit suggestion in any of those publications that the compounds described therein might be effective in a method of inhibiting plasmepsin V activity.

WO 2006/041404 describes a family of heterocyclic compounds that are stated to be inhibitors of Beta site APP (amyloid precursor protein) Cleaving Enzyme (BACE). The compounds described in that publication are also stated to be effective in a method of modulating BACE activity; and in methods of treating or preventing an amyloid-β-protein-related (Aβ-related) pathology, including Downs syndrome and Alzheimer disease. However, there is no suggestion anywhere in that publication that the compounds described therein might be effective in a method of inhibiting plasmepsin activity generally; or, more specifically, that they might be effective in a method of inhibiting plasmepsin V activity.

The present invention provides a compound of formula (I) or a pharmaceutically acceptable salt thereof:

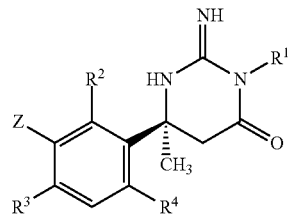

wherein
Z represents a fused bicyclic ring system comprising ring A and ring B, in which
ring A is an unsaturated five- or six-membered ring that is directly attached to the benzene ring depicted in formula (I) above;
ring A contains at least one nitrogen atom;
ring B is an unsaturated five- or six-membered ring that is fused to ring A;
the fused bicyclic ring system Z optionally contains one, two or three additional heteroatoms selected from nitrogen, oxygen and sulfur, of which not more than one is an oxygen atom or a sulfur atom; and
the fused bicyclic ring system Z is optionally substituted by one or more substituents;
$R^1$ represents hydrogen; or $R^1$ represents $C_{1-6}$ alkyl, optionally substituted by hydroxy; and
$R^2$, $R^3$ and $R^4$ independently represent hydrogen or halogen.

The compounds in accordance with the present invention are encompassed within the broadest generic scope of WO 2008/103351, WO 2006/065277, WO 2005/058311 and WO 2006/041404. There is, however, no specific disclosure in any of those publications of a compound of formula (I) as defined above, or a pharmaceutically acceptable salt thereof.

The present invention also provides a compound of formula (I) as defined above, or a pharmaceutically acceptable salt thereof, for use in therapy.

The present invention also provides a compound of formula (I) as defined above, or a pharmaceutically acceptable salt thereof, for use in the treatment and/or prevention of malaria.

The present invention also provides a method for the treatment and/or prevention of malaria which comprises administering to a patient in need of such treatment an effective amount of a compound of formula (I) as defined above, or a pharmaceutically acceptable salt thereof.

The present invention also provides the use of a compound of formula (I) as defined above, or a pharmaceutically acceptable salt thereof, for the manufacture of a medicament for the treatment and/or prevention of malaria.

Where any of the groups in the compounds of formula (I) above is stated to be optionally substituted, this group may be unsubstituted, or substituted by one or more substituents. Typically, such groups will be unsubstituted, or substituted by one, two or three substituents, generally by one or two substituents.

For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharma-* ceutical Salts: Properties, Selection and Use, ed. P. H. Stahl & C. G. Wermuth, Wiley-VCH, 2002.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulfonyl" and "$C_{1-6}$ alkylamino" are to be construed accordingly.

The term "heteroaryl" as used herein refers to monovalent aromatic groups containing at least five atoms derived from a single ring or multiple condensed rings, wherein one or more carbon atoms have been replaced by one or more heteroatoms selected from oxygen, sulfur and nitrogen. Suitable heteroaryl groups include furyl, benzofuryl, dibenzofuryl, thienyl, benzothienyl, thieno[2,3-c]pyrazolyl, thieno[3,2-c]-pyridinyl, dibenzothienyl, pyrrolyl, indolyl, pyrrolo[2,3-b]pyridinyl, pyrrolo[3,2-c]-pyridinyl, pyrrolo[3,4-b]pyridinyl, pyrazolyl, pyrazolo[1,5-a]pyridinyl, pyrazolo[3,4-d]-pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]-thiazolyl, imidazo[1,2-a]pyridinyl, imidazo[4,5-b]pyridinyl, purinyl, imidazo[1,2-a]-pyrimidinyl, imidazo[1,2-a]pyrazinyl, oxadiazolyl, thiadiazolyl, triazolyl, [1,2,4]triazolo-[1,5-a]pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

The absolute stereochemical configuration of the chiral carbon atom in the iminotetrahydropyrimidinone nucleus of the compounds according to the invention is as depicted in formula (I) above. Generally, the compounds in accordance with the invention are at least 51% enantiomerically pure (by which it is meant that a sample thereof comprises a mixture of enantiomers containing 51% or more of the enantiomer depicted in formula (I) and 49% or less of the opposite antipode). Typically, the compounds in accordance with the invention are at least 60% enantiomerically pure. Appositely, the compounds in accordance with the invention are at least 75% enantiomerically pure. Suitably, the compounds in accordance with the invention are at least 80% enantiomerically pure. More suitably, the compounds in accordance with the invention are at least 85% enantiomerically pure. Still more suitably, the compounds in accordance with the invention are at least 90% enantiomerically pure. Even more suitably, the compounds in accordance with the invention are at least 95% enantiomerically pure. Preferably, the compounds in accordance with the invention are at least 99% enantiomerically pure. Ideally, the compounds in accordance with the invention are at least 99.9% enantiomerically pure.

Where the compounds of formula (I) have one or more additional asymmetric centres, they may accordingly exist as enantiomers. Where the compounds of use in the invention possess one or more additional asymmetric centres, they may also exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=O)↔enol (CH=CHOH) tautomers or amide (NHC=O)↔hydroxyimine (N=COH) tautomers or imide (NHC=NH)↔aminoimine (N=CNH$_2$) tautomers. Formula (I) and the formulae depicted hereinafter are intended to represent all individual tautomers and all possible mixtures thereof, unless stated or shown otherwise. In addition, under certain circumstances, e.g. where $R^2$ represents fluoro, compounds of formula (I) may exist as atropisomers. Formula (I) and the formulae depicted hereinafter are intended to represent all individual atropisomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, ring A is an unsaturated five-membered ring. In a second embodiment, ring A is an unsaturated six-membered ring.

In a first embodiment, ring B is an unsaturated five-membered ring. In a second embodiment, ring B is an unsaturated six-membered ring.

Thus, the fused bicyclic ring system Z may typically comprise a five-membered ring fused to a five-membered ring, or a six-membered ring fused to a five-membered ring, or a six-membered ring fused to a six-membered ring, any of which ring systems may be optionally substituted by one or more substituents. The fused bicyclic ring system Z may suitably comprise a six-membered ring fused to a five-membered ring, or a six-membered ring fused to a six-membered ring, either of which ring systems may be optionally substituted by one or more substituents. In a first embodiment, the fused bicyclic ring system Z comprises a five-membered ring fused to a five-membered ring, which ring system may be optionally substituted by one or more substituents. In a second embodiment, the fused bicyclic ring system Z comprises a six-membered ring fused to a five-membered ring, which ring system may be optionally substituted by one or more substituents. In a third embodiment, the fused bicyclic ring system Z comprises a six-membered ring fused to a six-membered ring, which ring system may be optionally substituted by one or more substituents.

In a first embodiment, the fused bicyclic ring system Z contains one nitrogen atom (in ring A) and no additional heteroatoms. In a second embodiment, the fused bicyclic ring system Z contains one nitrogen atom (in ring A) and one additional heteroatom selected from nitrogen, oxygen and sulfur. In a third embodiment, the fused bicyclic ring system Z contains one nitrogen atom (in ring A) and two additional heteroatoms selected from nitrogen, oxygen and sulfur, of which not more than one is an oxygen atom or a sulfur atom. In a fourth embodiment, the fused bicyclic ring system Z contains one nitrogen atom (in ring A) and three additional heteroatoms selected from nitrogen, oxygen and sulfur, of which not more than one is an oxygen atom or a sulfur atom.

Typically, ring A represents a pyrrole, pyrazole, oxazole, isoxazole, thiazole, isothiazole, imidazole, oxadiazole, thiadiazole, triazole, pyridine, pyridazine, pyrimidine, pyrazine or triazine ring. Additionally, ring A may represent an imidazoline ring.

Suitably, ring A represents a pyrrole, pyrazole, thiazole, imidazole or pyridine ring. Additionally, ring A may represent an imidazoline ring.

Typically, ring B represents a benzene, furan, thiophene, pyrrole, pyrazole, oxazole, isoxazole, thiazole, isothiazole, imidazole, oxadiazole, thiadiazole, triazole, pyridine, pyridazine, pyrimidine, pyrazine or triazine ring.

Suitably, ring B represents a benzene or pyridine ring.

Typical values of the fused bicyclic ring system Z include thieno[2,3-c]pyrazolyl, thieno[3,2-c]pyridinyl, indolyl, pyrrolo[2,3-b]pyridinyl, pyrrolo[3,2-c]pyridinyl, pyrrolo-[3,4-b]pyridinyl, pyrazolo[1,5-a]pyridinyl, pyrazolo[3,4-d]pyrimidinyl, indazolyl, benzoxazolyl, benzothiazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]-pyrazinyl, [1,2,4]triazolo[1,5-a]pyrimidinyl, benzotriazolyl, quinolinyl, isoquinolinyl, naphthyridinyl, cinnolinyl, phthalazinyl, quinazolinyl, quinoxalinyl and pteridinyl, any of which groups may be optionally substituted by one or more substituents.

Suitable values of the fused bicyclic ring system Z include indolyl, pyrazolo[1,5-a]pyridinyl, indazolyl, benzothiazolyl, benzimidazolyl, imidazo[1,2-a]pyridinyl, imidazo-[4,5-b]pyridinyl and quinolinyl, any of which groups may be optionally substituted by one or more substituents.

Typical values of optional substituents on Z include one, two or three substituents independently selected from halogen, cyano, nitro, $C_{1-6}$ alkyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl. Additional values include oxo and di($C_{1-6}$)alkylamino($C_{1-6}$)-alkyl. Further values include difluoromethyl, cyclopropyl, cyclobutyl, pyrrolidinyl, morpholinyl and benzylamino.

Selected values of optional substituents on Z include one, two or three substituents independently selected from halogen, cyano, $C_{1-6}$ alkyl, difluoromethyl, trifluoromethyl, cyclopropyl, cyclobutyl, pyrrolidinyl, morpholinyl, methylpyrazolyl, oxo, hydroxy, hydroxy($C_{1-6}$)alkyl, $C_{1-6}$ alkoxy, difluoromethoxy, $C_{1-6}$ alkylsulfonyl, amino, $C_{1-6}$ alkylamino, di($C_{1-6}$)alkylamino, di($C_{1-6}$)alkylamino($C_{1-6}$)alkyl, benzylamino, carboxy, di($C_{1-6}$)alkylaminocarbonyl and di($C_{1-6}$)alkylaminosulfonyl.

Apposite values of optional substituents on Z include one, two or three substituents independently selected from halogen, cyano, $C_{1-6}$ alkyl, trifluoromethyl, methylpyrazolyl, oxo, hydroxy, hydroxy($C_{1-6}$)alkyl, $C_{1-6}$ alkoxy, $C_{1-6}$ alkylsulfonyl, di($C_{1-6}$)alkylamino, di($C_{1-6}$)alkylamino($C_{1-6}$) alkyl, carboxy, di($C_{1-6}$)alkylaminocarbonyl and di($C_{1-6}$)alkylaminosulfonyl.

Suitable values of optional substituents on Z include one, two or three substituents independently selected from halogen, cyano, $C_{1-6}$ alkyl, trifluoromethyl, methylpyrazolyl, hydroxy($C_{1-6}$)alkyl, $C_{1-6}$ alkoxy, $C_{1-6}$ alkylsulfonyl, carboxy, di($C_{1-6}$)alkylaminocarbonyl and di($C_{1-6}$)alkylaminosulfonyl.

Typical values of particular substituents on Z include one, two or three substituents independently selected from fluoro, chloro, bromo, cyano, nitro, methyl, ethyl, isopropyl, trifluoromethyl, methylpyrazolyl, hydroxy, hydroxymethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl and dimethylaminosulfonyl. Additional values include oxo, hydroxyethyl, hydroxyisopropyl and dimethylaminomethyl. Further values include difluoromethyl, cyclopropyl, cyclobutyl, pyrrolidinyl, morpholinyl and benzylamino.

Selected values of particular substituents on Z include one, two or three substituents independently selected from fluoro, chloro, bromo, cyano, methyl, ethyl, difluoromethyl, trifluoromethyl, cyclopropyl, cyclobutyl, pyrrolidinyl, morpholinyl, methylpyrazolyl, oxo, hydroxy, hydroxymethyl, hydroxyethyl, hydroxyisopropyl, methoxy, difluoromethoxy, methylsulfonyl, amino, methylamino, dimethylamino, dimethylaminomethyl, benzylamino, carboxy, dimethylaminocarbonyl and dimethylaminosulfonyl.

Apposite values of particular substituents on Z include one, two or three substituents independently selected from fluoro, chloro, bromo, cyano, methyl, ethyl, trifluoromethyl, methylpyrazolyl, oxo, hydroxy, hydroxymethyl, hydroxyethyl, hydroxyisopropyl, methoxy, methylsulfonyl, dimethylamino, dimethylaminomethyl, carboxy, dimethylaminocarbonyl and dimethylaminosulfonyl.

Suitable values of particular substituents on Z include one, two or three substituents independently selected from chloro, bromo, cyano, methyl, ethyl, trifluoromethyl, methylpyrazolyl, hydroxymethyl, methoxy, methylsulfonyl, carboxy, dimethylaminocarbonyl and dimethylaminosulfonyl.

Selected values of Z include (chloro)(cyano)(methyl) indolyl, dimethylpyrazolo-[1,5-a]pyridinyl, chloroindazolyl, benzothiazolyl, chlorobenzimidazolyl, methyl-benzimidazolyl, (chloro)(methyl)benzimidazolyl, (bromo) (methyl)benzimidazolyl, (cyano)(methyl)benzimidazolyl, (chloro)(ethyl)benzimidazolyl, (fluoro)(trifluoromethyl)-benzimidazolyl, (methyl)(trifluoromethyl)benzimidazolyl, (chloro)(cyclobutyl)-benzimidazolyl, (chloro)(pyrrolidinyl) benzimidazolyl, (chloro)(morpholinyl)-benzimidazolyl, (methyl)(methylpyrazolyl)benzimidazolyl, (chloro)(oxo) benzimidazolyl, (hydroxy)(methyl)benzimidazolyl, (chloro) (hydroxymethyl)benzimidazolyl, (hydroxymethyl)(methyl) benzimidazolyl, (hydroxyethyl)(methyl)benzimidazolyl, (hydroxyisopropyl)(methyl)benzimidazolyl, (methoxy) (methyl)benzimidazolyl, (methyl)(methylsulfonyl)benzimidazolyl, (chloro)(methylamino)benzimidazolyl, (chloro)(dimethylamino)benzimidazolyl, (cyano)(dimethylamino) benzimidazolyl, (dimethylaminomethyl)(methyl) benzimidazolyl, (carboxy)(methyl)benzimidazolyl, (dimethylaminocarbonyl)(methyl)benzimidazolyl, (dimethylaminosulfonyl)(methyl)-benzimidazolyl, (dichloro)(methyl)benzimidazolyl, (difluoromethyl)(fluoro)(methyl)-benzimidazolyl, (fluoro)(methyl)(trifluoromethyl) benzimidazolyl, (chloro)(methyl)-(trifluoromethyl) benzimidazolyl, (cyclobutyl)(fluoro)(trifluoromethyl) benzimidazolyl, (cyclopropyl)(fluoro)(trifluoromethyl) benzimidazolyl, (fluoro)(oxo)(trifluoromethyl)-benzimidazolyl, (chloro)(oxo)(trifluoromethyl) benzimidazolyl, (chloro)(hydroxy)-(methyl) benzimidazolyl, (fluoro)(hydroxyisopropyl) (trifluoromethyl)benzimidazolyl, (fluoro)(methoxy) (trifluoromethyl)benzimidazolyl, (chloro)(methoxy)

(methyl)-benzimidazolyl, (difluoromethoxy)(fluoro)(methyl)benzimidazolyl, (amino)(fluoro)-(trifluoromethyl)benzimidazolyl, (fluoro)(methylamino)(trifluoromethyl)benzimidazolyl, (fluoro)(dimethylamino)(trifluoromethyl)benzimidazolyl, (chloro)(cyano)(dimethyl-amino)benzimidazolyl, (benzylamino)(fluoro)(trifluoromethyl)benzimidazolyl, imidazo[1,2-a]pyridinyl, (chloro)(methyl)imidazo[1,2-a]pyridinyl, (methyl)-(methylpyrazolyl)imidazo[1,2-a]pyridinyl, (chloro)(methyl)imidazo[4,5-b]pyridinyl, dimethylimidazo[4,5-b]pyridinyl and quinolinyl.

Apposite values of Z include (chloro)(cyano)(methyl)indolyl, dimethylpyrazolo-[1,5-a]pyridinyl, chloroindazolyl, benzothiazolyl, chlorobenzimidazolyl, methyl-benzimidazolyl, (chloro)(methyl)benzimidazolyl, (bromo)(methyl)benzimidazolyl, (cyano)(methyl)benzimidazolyl, (chloro)(ethyl)benzimidazolyl, (fluoro)(trifluoromethyl)benzimidazolyl, (methyl)(trifluoromethyl)benzimidazolyl, (methyl)(methylpyrazolyl)-benzimidazolyl, (hydroxy)(methyl)benzimidazolyl, (chloro)(hydroxymethyl)-benzimidazolyl, (hydroxymethyl)(methyl)benzimidazolyl, (hydroxyethyl)(methyl)-benzimidazolyl, (hydroxyisopropyl)(methyl)benzimidazolyl, (methoxy)(methyl)-benzimidazolyl, (methyl)(methylsulfonyl)benzimidazolyl, (chloro)(dimethylamino)-benzimidazolyl, (dimethylaminomethyl)(methyl)benzimidazolyl, (carboxy)(methyl)-benzimidazolyl, (dimethylaminocarbonyl)(methyl)benzimidazolyl, (dimethylamino-sulfonyl)(methyl)benzimidazolyl, (dichloro)(methyl)benzimidazolyl, (fluoro)(methyl)-(trifluoromethyl)benzimidazolyl, (chloro)(methyl)(trifluoromethyl)benzimidazolyl, (fluoro)(oxo)(trifluoromethyl)benzimidazolyl, (chloro)(hydroxy)(methyl)benzimidazolyl, (chloro)(methoxy)(methyl)benzimidazolyl, (fluoro)(dimethylamino)(trifluoromethyl)-benzimidazolyl, imidazo[1,2-a]pyridinyl, (chloro)(methyl)imidazo[1,2-a]pyridinyl, (methyl)(methylpyrazolyl)imidazo[1,2-a]pyridinyl, (chloro)(methyl)imidazo[4,5-b]-pyridinyl, dimethylimidazo[4,5-b]pyridinyl and quinolinyl.

Suitable values of Z include (chloro)(cyano)(methyl)indolyl, dimethylpyrazolo-[1,5-a]pyridinyl, chloroindazolyl, benzothiazolyl, chlorobenzimidazolyl, methyl-benzimidazolyl, (chloro)(methyl)benzimidazolyl, (bromo)(methyl)benzimidazolyl, (cyano)(methyl)benzimidazolyl, (chloro)(ethyl)benzimidazolyl, (methyl)(trifluoro-methyl)benzimidazolyl, (methyl)(methylpyrazolyl)benzimidazolyl, (chloro)-(hydroxymethyl)benzimidazolyl, (methoxy)(methyl)benzimidazolyl, (methyl)-(methylsulfonyl)benzimidazolyl, (carboxy)(methyl)benzimidazolyl, (dimethylaminocarbonyl)(methyl)benzimidazolyl, (dimethylaminosulfonyl)(methyl)benzimidazolyl, (dichloro)(methyl)benzimidazolyl, imidazo[1,2-a]pyridinyl, (chloro)(methyl)imidazo[1,2-a]pyridinyl, (methyl)(methylpyrazolyl)imidazo[1,2-a]pyridinyl, (chloro)(methyl)imidazo-[4,5-b]pyridinyl, dimethylimidazo[4,5-b]pyridinyl and quinolinyl.

Generally, $R^1$ represents hydrogen or $C_{1-6}$ alkyl.
More particularly, $R^1$ represents $C_{1-6}$ alkyl.
Appositely, $R^1$ represents hydrogen or $C_{1-4}$ alkyl.
Typically, $R^1$ represents $C_{1-4}$ alkyl.
Illustratively, $R^1$ represents hydrogen, $C_{1-6}$ alkyl or hydroxy($C_{1-6}$)alkyl.
More precisely, $R^1$ represents hydrogen, $C_{1-4}$ alkyl or hydroxy($C_{1-4}$)alkyl.
In a first embodiment, $R^1$ represents hydrogen. In a second embodiment, $R^1$ represents $C_{1-6}$ alkyl, especially $C_{1-4}$ alkyl. In a third embodiment, $R^1$ represents hydroxy($C_{1-6}$)alkyl, especially hydroxy($C_{1-4}$)alkyl.
Illustrative values of $R^1$ include hydrogen, methyl, ethyl and hydroxyethyl.

Selected values of $R^1$ include hydrogen, methyl, ethyl and 2-hydroxyethyl.
Typical values of $R^1$ include hydrogen and methyl.
Particular values of $R^1$ include methyl, ethyl and isopropyl.
Suitably, $R^1$ represents methyl.
In one embodiment, $R^2$ represents hydrogen. In another embodiment, $R^2$ represents halogen, especially fluoro or chloro. In one aspect of that embodiment, $R^2$ represents fluoro. In another aspect of that embodiment, $R^2$ represents chloro.
Selected values of $R^2$ include hydrogen, fluoro and chloro.
Suitably, $R^2$ represents hydrogen or fluoro.
In one embodiment, $R^3$ represents hydrogen. In another embodiment, $R^3$ represents halogen, especially fluoro or chloro. In one aspect of that embodiment, $R^3$ represents fluoro. In another aspect of that embodiment, $R^3$ represents chloro.
Suitably, $R^3$ represents hydrogen or fluoro.
In one embodiment, $R^4$ represents hydrogen. In another embodiment, $R^4$ represents halogen, especially fluoro or chloro. In one aspect of that embodiment, $R^4$ represents fluoro. In another aspect of that embodiment, $R^4$ represents chloro.
Suitably, $R^4$ represents hydrogen or fluoro.
In a first embodiment, $R^2$, $R^3$ and $R^4$ all represent hydrogen. In a second embodiment, $R^2$ represents halogen, and $R^3$ and $R^4$ both represent hydrogen. In a third embodiment, $R^2$ and $R^4$ both represent hydrogen, and $R^3$ represents halogen. In a fourth embodiment, $R^2$ and $R^3$ both represent halogen, and $R^4$ represents hydrogen. In a fifth embodiment, $R^2$ and $R^3$ both represent hydrogen, and $R^4$ represents halogen. In a sixth embodiment, $R^2$ and $R^4$ both represent halogen, and $R^3$ represents hydrogen. In a seventh embodiment, $R^2$ represents hydrogen, and $R^3$ and $R^4$ both represent halogen. In an eighth embodiment, $R^2$, $R^3$ and $R^4$ all represent halogen.
Suitably, $R^2$ represents hydrogen or halogen; $R^3$ represents hydrogen or halogen; and $R^4$ represents hydrogen.
Generally, $R^2$ represents hydrogen or halogen; and $R^3$ and $R^4$ both represent hydrogen.
One sub-class of compounds according to the invention is represented by the compounds of formula (IIA), and pharmaceutically acceptable salts thereof:

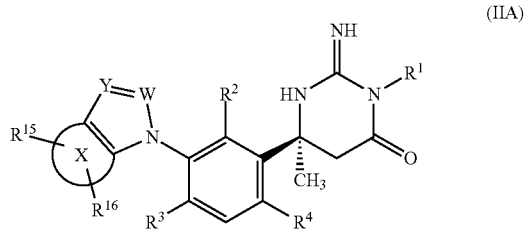

(IIA)

wherein
ring X represents a benzene or pyridine ring;
W represents N or C—$R^3$;
Y represents N or C—$R^{14}$;
$R^{13}$ represents hydrogen, methyl, ethyl, cyclopropyl, cyclobutyl, pyrrolidinyl, morpholinyl, hydroxymethyl, hydroxyisopropyl, methoxy, amino, methylamino, dimethylamino or benzylamino;
$R^{14}$ represents hydrogen, cyano or $C_{1-4}$ alkyl;
$R^{15}$ and $R^{16}$ independently represent hydrogen, halogen, cyano, nitro, $C_{1-6}$ alkyl, difluoromethyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; and $R^1$, $R^2$, $R^3$ and $R^4$ are as defined above.

As specified above, ring X represents a benzene or pyridine ring, by which it is meant that the partial ring enclosing the integer X, when taken together with the two carbon atoms of the adjoining five-membered ring, represents a benzene or pyridine ring.

In a first embodiment, ring X represents a benzene ring. In a second embodiment, ring X represents a pyridine ring.

In a first embodiment, W represents N. In a second embodiment, W represents C—$R^{13}$.

In a first embodiment, Y represents N. In a second embodiment, Y represents C—$R^{14}$.

Suitably, W represents C—$R^{13}$ and Y represents N; or W represents C—$R^{13}$ and Y represents C—$R^{14}$; or W represents N and Y represents C—$R^{14}$.

In a first embodiment, W represents C—$R^{13}$ and Y represents N. In a second embodiment, W represents C—$R^{13}$ and Y represents C—$R^{14}$. In a third embodiment, W represents N and Y represents C—$R^{14}$.

Generally, $R^{13}$ represents hydrogen, methyl, ethyl, hydroxymethyl or dimethyl-amino.

More particularly, $R^{13}$ represents hydrogen, methyl, ethyl or hydroxymethyl.

In a first embodiment, $R^{13}$ represents hydrogen. In a second embodiment, $R^{13}$ represents methyl. In a third embodiment, $R^{13}$ represents ethyl. In a fourth embodiment, $R^{13}$ represents cyclopropyl. In a fifth embodiment, $R^{13}$ represents cyclobutyl. In a sixth embodiment, $R^{13}$ represents pyrrolidinyl, especially pyrrolidin-1-yl. In a seventh embodiment, $R^{13}$ represents morpholinyl, especially morpholin-4-yl. In an eighth embodiment, $R^{13}$ represents hydroxymethyl. In a ninth embodiment, $R^{13}$ represents hydroxyisopropyl, especially 2-hydroxyprop-2-yl. In a tenth embodiment, $R^{13}$ represents methoxy. In an eleventh embodiment, $R^{13}$ represents amino. In a twelfth embodiment, $R^{13}$ represents methylamino. In a thirteenth embodiment, $R^{13}$ represents dimethylamino. In a fourteenth embodiment, $R^{13}$ represents benzylamino.

In a first embodiment, $R^{14}$ represents hydrogen. In a second embodiment, $R^{14}$ represents cyano. In a third embodiment, $R^{14}$ represents $C_{1-4}$ alkyl, especially methyl.

Suitably, $R^{14}$ represents hydrogen or cyano.

Generally, $R^{15}$ and $R^{16}$ independently represent hydrogen, halogen, cyano, nitro, $C_{1-6}$ alkyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, di($C_{1-6}$)alkylamino($C_{1-6}$)alkyl, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl.

More particularly, $R^{15}$ and $R^{16}$ independently represent hydrogen, halogen, cyano, nitro, $C_{1-6}$ alkyl, trifluoromethyl, methylpyrazolyl, hydroxy, hydroxy($C_{1-6}$)alkyl, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl. Additional values include di($C_{1-6}$)alkylamino($C_{1-6}$)alkyl.

Typically, $R^{15}$ and $R^{16}$ may independently represent hydrogen, fluoro, chloro, bromo, cyano, nitro, methyl, ethyl, isopropyl, trifluoromethyl, methylpyrazolyl, hydroxy, hydroxymethyl, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, ethoxycarbonyl, aminocarbonyl, methylaminocarbonyl, dimethylaminocarbonyl, aminosulfonyl, methylaminosulfonyl or dimethylaminosulfonyl. Additional values include hydroxyethyl, hydroxyisopropyl and dimethylaminomethyl. Further values include difluoromethyl.

Favoured values of $R^{15}$ include hydrogen, halogen, cyano, $C_{1-6}$ alkyl, difluoromethyl, trifluoromethyl, methylpyrazolyl, hydroxy, hydroxy($C_{1-6}$)alkyl, $C_{1-6}$ alkoxy, difluoromethoxy, $C_{1-6}$ alkylsulfonyl, di($C_{1-6}$)alkylamino($C_{1-6}$)alkyl, carboxy, di($C_{1-6}$)alkylaminocarbonyl and di($C_{1-6}$)alkylaminosulfonyl.

Suitable values of $R^{15}$ include hydrogen, halogen, cyano, $C_{1-6}$ alkyl, trifluoro-methyl, methylpyrazolyl, hydroxy, hydroxy($C_{1-6}$)alkyl, $C_{1-6}$ alkoxy, $C_{1-6}$ alkylsulfonyl, di($C_{1-6}$)alkylamino($C_{1-6}$)alkyl, carboxy, di($C_{1-6}$)alkylaminocarbonyl and di($C_{1-6}$)alkylaminosulfonyl.

Typical values of $R^{15}$ include hydrogen, halogen, cyano, $C_{1-6}$ alkyl, trifluoro-methyl, methylpyrazolyl, $C_{1-6}$ alkoxy, $C_{1-6}$ alkylsulfonyl, carboxy, di($C_{1-6}$)alkylaminocarbonyl and di($C_{1-6}$)alkylaminosulfonyl.

Specific values of $R^{15}$ include hydrogen, fluoro, chloro, bromo, cyano, methyl, difluoromethyl, trifluoromethyl, methylpyrazolyl, hydroxy, hydroxymethyl, hydroxyethyl, hydroxyisopropyl, methoxy, difluoromethoxy, methylsulfonyl, dimethylaminomethyl, carboxy, dimethylaminocarbonyl and dimethylaminosulfonyl.

Particular values of $R^{15}$ include hydrogen, fluoro, chloro, bromo, cyano, methyl, trifluoromethyl, methylpyrazolyl, hydroxy, hydroxymethyl, hydroxyethyl, hydroxyisopropyl, methoxy, methylsulfonyl, dimethylaminomethyl, carboxy, dimethylaminocarbonyl and dimethylaminosulfonyl.

Selected values of $R^{15}$ include hydrogen, chloro, bromo, cyano, methyl, trifluoro-methyl, methylpyrazolyl, methoxy, methylsulfonyl, carboxy, dimethylaminocarbonyl and dimethylaminosulfonyl.

Typical values of $R^{16}$ include hydrogen and halogen.

In a first embodiment, $R^{16}$ represents hydrogen. In a second embodiment, $R^{16}$ represents halogen. In a first aspect of that embodiment, $R^{16}$ represents fluoro. In a second aspect of that embodiment, $R^{16}$ represents chloro.

Apposite values of $R^{16}$ include hydrogen, fluoro and chloro.

Suitable values of $R^{16}$ include hydrogen and chloro.

Particular subgroups of the compounds of formula (IIA) above are represented by the compounds of formula (IIA-1), (IIA-2) and (IIA-3), and pharmaceutically acceptable salts thereof:

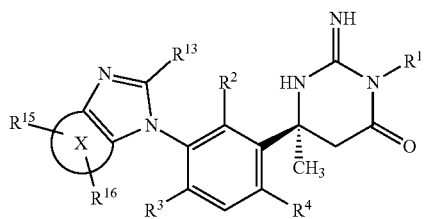
(IIA-1)

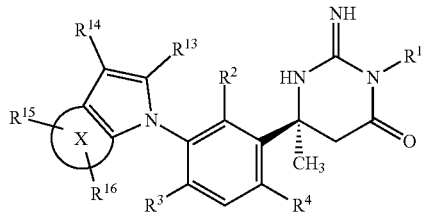
(IIA-2)

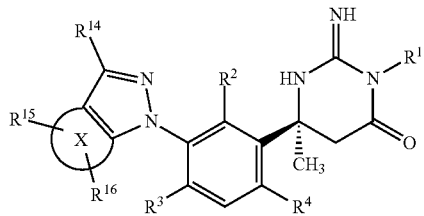
(IIA-3)

wherein X, R¹, R², R³, R⁴, R¹³, R¹⁴, R¹⁵ and R¹⁶ are as defined above.

Specific subgroups of the compounds of formula (IIA-1) above include the compounds of formula (IIA-1a), (IIA-1b) and (IIA-1c), and pharmaceutically acceptable salts thereof:

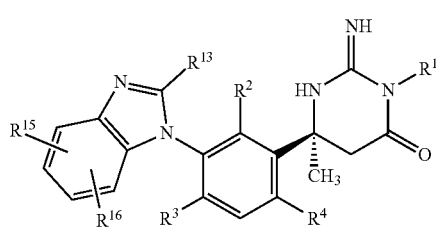
(IIA-1a)

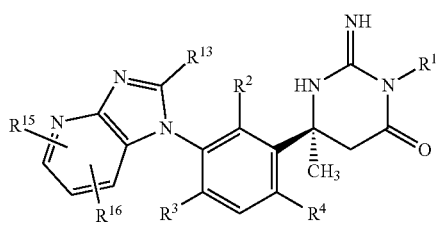
(IIA-1b)

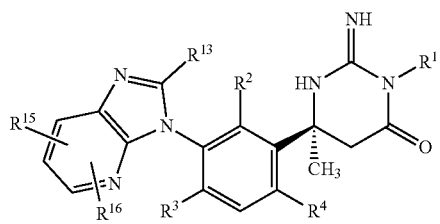
(IIA-1c)

wherein R¹, R², R³, R⁴, R¹³, R¹⁵ and R¹⁶ are as defined above.

A specific subgroup of the compounds of formula (IIA-2) above includes the compounds of formula (IIA-2a), and pharmaceutically acceptable salts thereof:

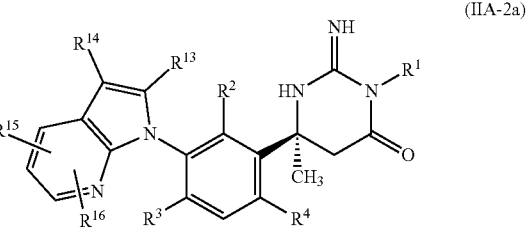
(IIA-2a)

wherein R¹, R², R³, R⁴, R¹³, R¹⁴, R¹⁵ and R¹⁶ are as defined above.

A specific subgroup of the compounds of formula (IIA-3) above includes the compounds of formula (IIA-3a), and pharmaceutically acceptable salts thereof:

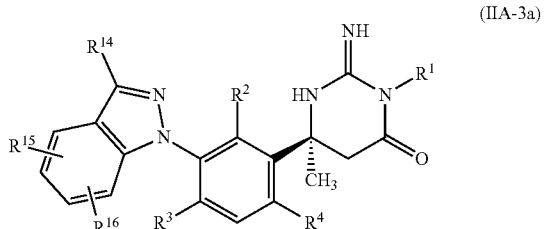
(IIA-3a)

wherein R¹, R², R³, R⁴, R¹⁴, R¹⁵ and R¹⁶ are as defined above.

Another sub-class of compounds according to the invention is represented by the compounds of formula (IIB), and pharmaceutically acceptable salts thereof:

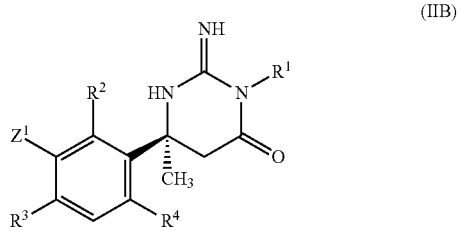
(IIB)

wherein

Z¹ represents a group of formula (Za), (Zb), (Zc) or (Zd):

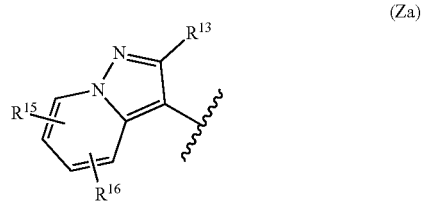
(Za)

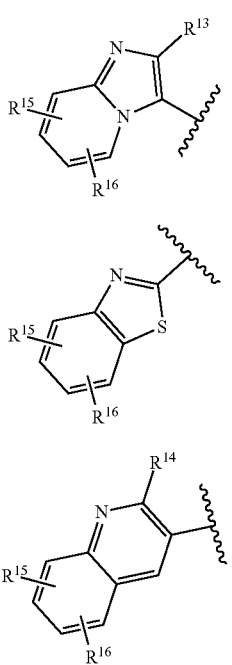

in which the wavy line represents the point of attachment to the remainder of the molecule; and $R^1$, $R^2$, $R^3$, $R^4$, $R^{13}$, $R^{14}$, $R^{15}$ and $R^{16}$ are as defined above.

In a first embodiment, $Z^1$ represents a group of formula (Za) as defined above. In a second embodiment, $Z^1$ represents a group of formula (Zb) as defined above. In a third embodiment, $Z^1$ represents a group of formula (Zc) as defined above. In a fourth embodiment, $Z^1$ represents a group of formula (Zd) as defined above.

Another sub-class of compounds according to the invention is represented by the compounds of formula (IIC), and pharmaceutically acceptable salts thereof:

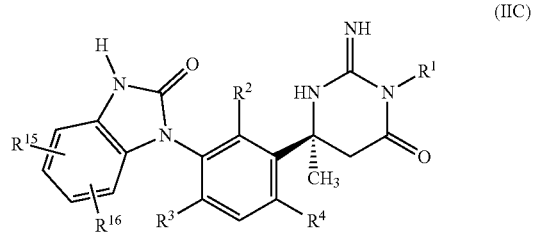

wherein $R^1$, $R^2$, $R^3$, $R^4$, $R^{15}$ and $R^{16}$ are as defined above.

Specific novel compounds in accordance with the present invention include each of the compounds whose preparation is described in the accompanying Examples, and pharmaceutically acceptable salts thereof.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

General methods for the preparation of the compounds of formula (I) as defined above are described in WO 2008/103351 and WO 2006/041404.

The compounds in accordance with the invention as represented by formula (IIA-1) above may be prepared by a process which comprises reacting a compound of formula $R^{13}$—CHO with a compound of formula (III):

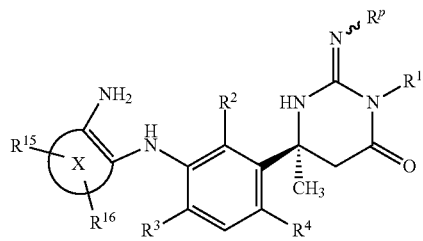

wherein X, $R^1$, $R^2$, $R^3$, $R^4$, $R^{13}$, $R^{15}$ and $R^{16}$ are as defined above, and $R^p$ represents hydrogen or an N-protecting group; in the presence of a transition metal catalyst; followed, as necessary, by removal of the N-protecting group $R^p$.

Suitably, the transition metal catalyst of use in the above reaction is a copper(II) salt, e.g. copper(II) acetate.

The reaction between the compound of formula $R^{13}$—CHO and compound (III) is conveniently accomplished at an elevated temperature in a suitable solvent, e.g. a $C_{1-4}$ alkanol such as methanol or ethanol.

In an alternative procedure, the compounds in accordance with the invention as represented by formula (IIA-1) above may be prepared by a process which comprises reacting a compound of formula $R^{13}$—$CO_2H$ with a compound of formula (III) as defined above; followed, as necessary, by removal of the N-protecting group $R^p$.

The reaction between the compound of formula $R^{13}$—$CO_2H$ and compound (III) is conveniently accomplished by mixing the reactants at an elevated temperature.

In an alternative procedure, the compounds in accordance with the invention as represented by formula (IIA-1) above, wherein $R^{13}$ represents dimethylamino, may be prepared by a process which comprises reacting (dichloromethylene) dimethylammonium chloride (Vilsmeier reagent) with a compound of formula (III) as defined above; followed, as necessary, by removal of the N-protecting group $R^p$.

The reaction between Vilsmeier reagent and compound (III) is conveniently accomplished at ambient temperature in a suitable solvent, e.g. a chlorinated solvent such as dichloromethane.

Similarly, the compounds in accordance with the invention as represented by formula (IIA-1) above, wherein $R^{13}$ represents pyrrolidin-1-yl, may be prepared by a process which comprises reacting 1-(dichloromethylene)pyrrolidinium chloride with a compound of formula (III) as defined above; followed, as necessary, by removal of the N-protecting group $R^p$.

The reaction between 1-(dichloromethylene)pyrrolidinium chloride and compound (III) is conveniently accomplished at ambient temperature in a suitable solvent, e.g. a chlorinated solvent such as dichloromethane.

In an alternative procedure, the compounds in accordance with the invention as represented by formula (IIA-1) above, wherein $R^{13}$ represents methylamino or benzylamino, may be prepared by a process which comprises reacting methyl isothiocyanate or benzyl isothiocyanate respectively with a compound of formula (III) as defined above; followed, as necessary, by removal of the N-protecting group $R^p$.

The reaction between methyl isothiocyanate or benzyl isothiocyanate and compound (III) is typically effected in the presence of an activating agent such as 1-ethyl-3-(3-dimethylaminopropyl)carbodiimide (EDCI). The reaction is conveniently accomplished at an elevated temperature in a suitable solvent, e.g. tetrahydrofuran or pyridine.

Suitably, the N-protecting group $R^p$ is tert-butoxycarbonyl (BOC).

Where the N-protecting group $R^p$ is BOC, subsequent removal of the BOC group may suitably be accomplished by treatment with an acid, e.g. a mineral acid such as hydrochloric acid, or an organic acid such as trifluoroacetic acid, typically at ambient temperature in a suitable solvent, e.g. a chlorinated solvent such as dichloromethane, or a cyclic ether such as 1,4-dioxane.

The intermediates of formula (III) above may be prepared by treating a compound of formula (IV):

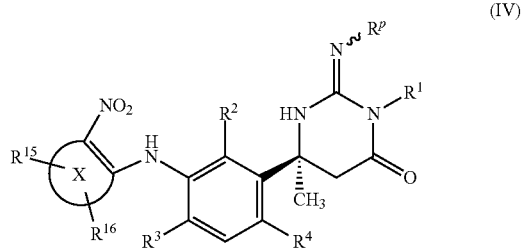

wherein X, $R^1$, $R^2$, $R^3$, $R^4$, $R^{15}$, $R^{16}$ and $R^p$ are as defined above; with a reducing agent.

Suitably, the reducing agent of use in the above reaction may be a mixture of zinc and ammonium formate, in which case the reaction may conveniently be accomplished at ambient temperature in a suitable solvent, e.g. a $C_{1-4}$ alkanol such as methanol.

Alternatively, the reducing agent may be tin(II) chloride, in which case the reaction may conveniently be accomplished at an elevated temperature in a suitable solvent, e.g. a $C_{1-4}$ alkanol such as ethanol.

Alternatively, the compound of formula (IV) may be reduced by conventional catalytic hydrogenation, in which case the reaction may conveniently be accomplished by treating compound (IV) with hydrogen gas in the presence of a hydrogenation catalyst, e.g. palladium on charcoal. The reaction will typically be performed at ambient temperature in a suitable solvent, e.g. a $C_{1-4}$ alkanol such as methanol.

The intermediates of formula (IV) above may be prepared by reacting a compound of formula (V) with a compound of formula (VI):

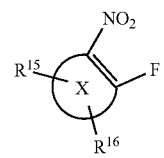

(V)

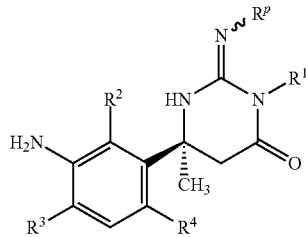

(VI)

wherein X, $R^1$, $R^2$, $R^3$, $R^4$, $R^{15}$, $R^{16}$ and $R^p$ are as defined above.

The reaction will generally be accomplished in the presence of a base, typically a strong organic base such as lithium bis(trimethylsilyl)amide or tert-butyllithium. The reaction may conveniently be effected in a suitable solvent, e.g. a cyclic ether such as tetrahydrofuran.

The compounds in accordance with the invention as represented by formula (IIA-2) above may be prepared by a two-step procedure which comprises: (i) reacting a compound of formula (VI) as defined above with a compound of formula (VII):

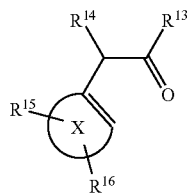

(VII)

wherein X, $R^{13}$, $R^{14}$, $R^{15}$ and $R^{16}$ are as defined above; and (ii) treatment of the resulting material with [bis(trifluoroacetoxy)iodo]benzene; followed, as necessary, by removal of the N-protecting group $R^p$.

Step (i) is conveniently effected at an elevated temperature in acetic acid.

Step (ii) is conveniently effected in a suitable solvent, e.g. a chlorinated solvent such as dichloromethane.

The compounds in accordance with the invention as represented by formula (IIA-3) above may be prepared by a process which comprises reacting a compound of formula (VIII) with a compound of formula (IX):

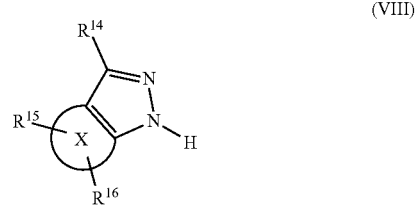

(VIII)

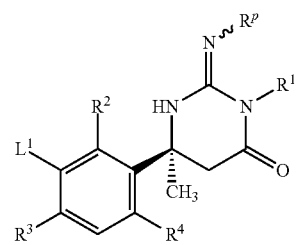

(IX)

wherein X, $R^1$, $R^2$, $R^3$, $R^4$, $R^{14}$, $R^{15}$, $R^{16}$ and $R^p$ are as defined above, and $L^1$ represents a suitable leaving group; in the presence of a transition metal catalyst; followed, as necessary, by removal of the N-protecting group $R^p$.

The leaving group $L^1$ is typically a halogen atom, e.g. bromo.

Suitably, the transition metal catalyst of use in the above reaction is a copper(II) salt, e.g. copper(II) acetate.

The reaction is conveniently accomplished at an elevated temperature in a suitable solvent, e.g. a dipolar aprotic solvent such as N,N-dimethylformamide, typically in the presence of pyridine.

The compounds in accordance with the invention as represented by formula (IIB) above may be prepared by a process which comprises reacting a compound of formula $Z^1$—$L^2$ with a compound of formula (X):

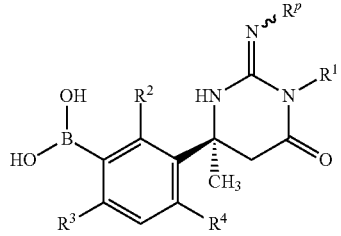

(X)

wherein $Z^1$, $R^1$, $R^2$, $R^3$, $R^4$ and $R^p$ are as defined above, and $L^2$ represents a suitable leaving group; in the presence of a transition metal catalyst; followed, as necessary, by removal of the N-protecting group $R^p$.

The leaving group $L^2$ is typically a halogen atom, e.g. bromo.

The transition metal catalyst of use in the reaction between the compound of formula $Z^1$—$L^2$ and compound (X) is suitably a palladium-containing catalyst such as chloro(2-dicyclohexylphosphino-2',4',6'-triisopropyl-1,1'-biphenyl)[2-(2'-amino-1,1'-biphenyl)]palladium(II).

The reaction is conveniently carried out at an elevated temperature in a suitable solvent, e.g. a $C_{1-4}$ alkanol such as ethanol, typically in the presence of 2-dicyclohexyl-phosphino-2',4',6'-triisopropylbiphenyl and a salt such as potassium acetate, potassium carbonate, potassium phosphate or sodium carbonate.

The intermediates of formula (X) above may be prepared by reacting a compound of formula (IX) as defined above with tetrahydroxydiboron; in the presence of a transition metal catalyst; under conditions analogous to those described above for the reaction between the compound of formula $Z^1$—$L^2$ and compound (X).

The compounds in accordance with the invention as represented by formula (IIC) above may be prepared by a process which comprises reacting a compound of formula (III) as defined above with triphosgene; followed, as necessary, by removal of the N-protecting group $R^p$.

The reaction will generally be accomplished in the presence of a base, e.g. an organic base such as trimethylamine. The reaction is conveniently effected at ambient temperature in a suitable solvent, e.g. a cyclic ether such as tetrahydrofuran.

Where they are not commercially available, the starting materials of formula (V), (VI), (VII), (VIII) and (IX) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

By way of example, a compound of formula (I) wherein Z is substituted by halogen, e.g. bromo or chloro, may be converted into the corresponding compound wherein Z is substituted by 1-methylpyrazol-4-yl by treatment with 1-methylpyrazol-4-ylboronic acid or a cyclic ester thereof formed with an organic diol, e.g. pinacol, 1,3-propanediol or neopentyl glycol. The reaction is typically effected in the presence of a transition metal catalyst, e.g. a palladium-containing catalyst such as (2-dicyclohexyl-phosphino-2',4',6'-triisopropylbiphenyl)palladium(II) phenethylamine chloride or chloro(2-dicyclohexylphosphino-2',4',6'-triisopropyl-1,1'-biphenyl)[2-(2'-amino-1,1'-biphenyl)]palladium(II), and a base, e.g. an inorganic base such as potassium tert-butoxide, potassium acetate or potassium carbonate.

A compound of formula (I) wherein Z is substituted by $C_{1-6}$ alkoxy, e.g. methoxy, may be converted into the corresponding compound wherein Z is substituted by hydroxy by treatment with boron tribromide.

A compound wherein Z is substituted by acetyl may be converted into the corresponding compound wherein Z is substituted by 2-hydroxyprop-2-yl by treatment with a methylmagnesium halide, e.g. methylmagnesium bromide. A compound wherein Z is substituted by acetyl may be converted into the corresponding compound wherein Z is substituted by 1-hydroxyethyl by treatment with a reducing agent such as sodium borohydride.

A compound of formula (IIA-1) wherein $R^{13}$ represents hydrogen may be converted into the corresponding compound of formula (IIA-1) wherein $R^{13}$ represents 2-hydroxyprop-2-yl by treatment with acetone in the presence of a base, e.g. n-butyllithium.

A compound of formula (IIC) may be converted into the corresponding compound of formula (IIA-1a) wherein $R^{13}$ represents methoxy by treatment with trimethyloxonium tetrafluoroborate.

A compound of formula (IIC) may be converted into the corresponding compound of formula (IIA-1a) wherein $R^{13}$ represents pyrrolidin-1-yl or morpholin-4-yl by a two-step procedure which comprises: (i) treatment with phosphorus oxychloride; and (ii) treatment of the chloro derivative thereby obtained with pyrrolidine or morpholine respectively. Step (i) is conveniently effected at an elevated temperature. Step (ii) is conveniently effected at an elevated temperature in a suitable solvent, e.g. a $C_{1-4}$ alkanol such as propan-2-ol.

A compound of formula (IIC) may be converted into the corresponding compound of formula (IIA-1a) wherein $R^{13}$ represents amino by a two-step procedure which comprises: (i) treatment with phosphorus oxychloride; and (ii) treatment of the chloro derivative thereby obtained with ammonia. Step (i) is conveniently effected at an elevated temperature. Step (ii) is conveniently effected at an elevated temperature in a suitable solvent, e.g. a $C_{1-4}$ alkanol such as methanol.

A compound of formula (I) containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds of the present invention are potent and selective inhibitors of plasmepsin V activity, inhibiting the aspartyl protease activity of *Plasmodium falciparum*: plasmepsin V ($IC_{50}$) at concentrations of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective activity, typically at least a 20-fold selective activity, suitably at least a 50-fold selective activity, and ideally at least a 100-fold selective activity, for *Plasmodium falciparum*: plasmepsin V relative to human aspartyl protease enzymes (including BACE).

Plasmepsin V Enzyme Assays

The assays used to measure the effect of test compounds on plasmepsin V activity were fluorescent resonant energy transfer (FRET) based, using a peptide substrate that had been labelled at each end with one of the FRET pair EDANS/Dabcyl. Excitation of EDANS results in fluorescent resonant energy transfer to Dabcyl, which is a dark quencher. Cleavage of the peptide by the protease prevents FRET with a resultant increase in EDANS fluorescent emission. Inhibition of the protease results in a decrease in the fluorescent signal. Test compounds were assayed in either one or the other of the two assays described below.

Plasmepsin V Assay 1

Plasmepsin V enzyme was diluted to 12.5 nM in assay buffer (50 mM sodium citrate, pH 6.5, 0.002% Tween 20). Test compounds were serially diluted 3-fold in DMSO (10 point titration), before being further diluted 1 in 10 in assay buffer. Plasmepsin V substrate (Anaspec catalogue number 64939) was dissolved in DMSO to 1 mM, before being further diluted 1 in 10 in assay buffer to 100 μM. Diluted test compound (5 μL) was mixed with plasmepsin V (40 μL) and incubated for 30 minutes at room temperature after addition of diluted plasmepsin V substrate (5 μL). The final concentrations of enzyme and substrate were 10 nM and 10 μM respectively. Final concentrations of test compound ranged from 100,000 nM to 5 nM in 2% DMSO. Fluorescent signal was measured using an Analyst HT plate reader (Excitation 330 nm, Emission 485 nm). Compound effect was expressed as % inhibition of the maximum signal generated (DMSO only controls) after subtraction of the minimum signal (no enzyme controls) from both. The $IC_{50}$ value was calculated from % inhibition, using a four parameter logistic curve fit.

Plasmepsin V Assay 2

Plasmepsin V enzyme was diluted to 40 nM in assay buffer (50 mM sodium citrate, pH 6.5, 0.002% Tween 20). Test compounds were serially diluted 2-fold in assay buffer (15 point titration). Plasmepsin V substrate (Anaspec catalogue number 64939) was dissolved in DMSO to 1 mM, before being further diluted 1 in 25 in assay buffer to 40 μM. Diluted test compound (12.5 μL) was mixed with plasmepsin V (6.25 μL) and incubated for 30 minutes at room temperature after addition of of diluted plasmepsin V substrate (6.25 μL). The final concentrations of enzyme and substrate were 10 nM and 10 μM respectively. Final top concentrations of test compound ranged from 5 μM to 30 μM in 1% DMSO. Fluorescent signal was measured using a SpectraMax Paradigm plate reader (Excitation 360 nm, Emission 465 nm). Fluorescence intensity of the samples with test compound was used to calculate the $IC_{50}$ value, using a four parameter logistic curve fit.

When tested in the plasmepsin V enzyme assay as described above (Assay 1 or Assay 2), the compounds of the accompanying Examples were all found to exhibit $IC_{50}$ values of 50 μM or better.

Thus, when tested in the plasmepsin V assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

EXAMPLES

Abbreviations

DCM: dichloromethane EtOAc: ethyl acetate
DMSO: dimethyl sulfoxide THF: tetrahydrofuran
MeOH: methanol DMF: N,N-dimethylformamide
DIPEA: N,N-diisopropylethylamine EtOH: ethanol
NBS: N-bromosuccinimide TFA: trifluoroacetic acid
LiHMDS: lithium bis(trimethylsilyl)amide HOBT: 1-hydroxybenzotriazole
EDCI: 1-ethyl-3-(3-dimethylaminopropyl)carbodiimide
$Pd(PPh_3)Cl_2$: dichlorobis(triphenylphosphine)palladium(II)
$Pd(dppf)Cl_2$: [1,1'-bis(diphenylphosphino)ferrocene]dichloropalladium(II)
PIFA: [bis(trifluoroacetoxy)iodo]benzene
XPhos: 2-dicyclohexylphosphino-2',4',6'-triisopropylbiphenyl
XPhos Pd G2: chloro(2-dicyclohexylphosphino-2',4',6'-triisopropyl-1,1'-biphenyl)[2-(2'-amino-1,1'-biphenyl)]palladium(II)
h: hour M: mass
DAD: Diode Array Detector
HPLC: High Performance Liquid Chromatography
LCMS: Liquid Chromatography Mass Spectrometry
ES+: Electrospray Positive Ionisation Nomenclature Compounds were named with the aid of ACD/Name Batch (Network) version.

Analytical Conditions

LCMS data for all Examples were determined by using Method 1, Method 2 or Method 3 below.

Preparative HPLC for all compounds that required it was performed using Method 4 or Method 5 below.

Method 1

| Waters Acquity-QDa SQD Mass Spectrometer - ESI Source | |
|---|---|
| Capillary Voltage | 0.80 kV |
| Cone Voltage | 30 V |
| Source Temperature | 120° C. |
| Desolvation Temperature | 600° C. |
| Mass Range | 120-800 |
| Sampling Frequency | 5 Hz |
| Column | Phenomenex Kinetex EVO 1.7 μm 2.1 × 50 mm |
| Injection Volume | 1-5 μL |
| UV data | 210 to 400 nm |
| Sample Temperature | Ambient |
| Column Temperature | 40° C. |
| Flow Rate | 1 mL/minute |

-continued

Waters Acquity-QDa
SQD Mass Spectrometer - ESI Source

| Solvent A | 10 mM ammonium formate + 0.1% ammonia |
| Solvent B | 95% acetonitrile + 5% water + 0.1% ammonia |

| Gradient: | Time | % A | % B |
| --- | --- | --- | --- |
| | 0.00 | 95 | 5 |
| | 0.10 | 95 | 5 |
| | 1.10 | 5 | 95 |
| | 1.35 | 5 | 95 |
| | 1.40 | 95 | 5 |
| | 1.60 | END | |

Method 2

| Column: | Phenomenex Luna C18(2) 5 µm 150 × 4.6 mm |
| Flow Rate | 1.5 mL/minute |
| Temperature | Ambient |
| Injection Volume | 20 µL |
| Detection: | |
| MS - ESI+ m/z | 150 to 800 |
| UV - DAD | 220-400 nm |
| Solvent A | 20 mM ammonium bicarbonate in water (freshly prepared and unadjusted) |
| Solvent B | acetonitrile |

| Gradient profile: | Time | Solvent B (%) |
| --- | --- | --- |
| | 0.10 | 1.5 |
| | 0.2 | 10 |
| | 9.0 | 99 |
| | 11.0 | 99 |
| | 11.1 | 10 |
| | 11.95 | 10 |
| | 12.0 | 10 |

A pre-conditioning run of 2 minutes with the starting conditions was used to re-equilibrate the column.

Method 3

| Column: | Waters x Bridge C18, 2.1 × 30 mm, 2.5 µm |
| Injection Volume | 5.0 µL |
| Flow Rate | 1.00 mL/minute |
| Detection: | |
| MS-ESI+ m/z | 150 to 800 |
| UV - DAD | 220-400 nm |
| Solvent A | 5 mM ammonium formate in water + 0.1% ammonia |
| Solvent B | acetonitrile + 5% Solvent A + 0.1% ammonia |
| Gradient program: | 5% B to 95% B in 4.0 minutes; hold until 5.00 minutes; at 5.10 minutes concentration of B is 5%; hold up to 6.5 minutes |

Method 4

| System: | Waters Fractionlynx system, with 2545 pump, 2998 PDA, 2767 fraction collector and a Waters 3100 MS |
| Column: | Waters XSelect CSH Prep C18, 5 µM, 19 × 100 mm |
| Flow Rate | 19 mL/minute (+1 mL/minute acetonitrile ACD) |
| Column Temperature | Ambient |
| Solvent A | 10 mM aqueous ammonium bicarbonate solution + 0.1% formic acid |
| Solvent B | acetonitrile + 0.1% formic acid |

| Gradient: | Time (min) | % A | % B |
| --- | --- | --- | --- |
| | 0 | 90 | 10 |
| | 2.3 | 90 | 10 |
| | 11 | 70 | 30 |
| | 11.5 | 5 | 95 |
| | 13 | 5 | 95 |
| | 13.2 | 90 | 10 |

Method 5

| System: | Shimadzu LC-8A |
| Column: | YMC ODS 500 × 30 mm, 10 µm |
| Flow Rate | 35 mL/minute |
| Solvent A | 0.1% formic acid in water |
| Solvent B | 0.1% formic acid in acetonitrile |

| Time (min) | % B |
| --- | --- |
| 0.01 | 10 |
| 2 | 10 |
| 15 | 40 |
| 20 | 90 |
| 20.10 | 100 |
| 25 | 100 |
| 25.10 | 10 |
| 30 | 10 |

Intermediate 1

(NE)-2-Methyl-N-[1-(3-nitrophenyl)ethylidene]propane-2-sulfinamide (R)-(+)-2-Methyl-2-propanesulfinamide (95.4 g, 787 mmol), 1-(3-nitrophenyl)ethanone (130 g, 787 mmol) and titanium(IV) ethoxide (359 g, 1.57 mol) in THF (1.70 L) were stirred at 80° C. for 16 h. Brine (1.5 L) was added and the mixture was stirred at 25° C. for 30 minutes, then filtered. The filter cake was washed with ethyl acetate (3×1 L) and the filtrate was washed with brine (500 mL), then dried over $Na_2SO_4$. The organic layer was concentrated. The residue was treated with 1:1 tert-butyl methyl ether:petroleum ether (1 L) and filtered. The filter cake was dried at 45° C. to give the title compound (120 g, 63%) as a yellow solid. $\delta_H$ (400 MHz, $CDCl_3$) 8.68 (s, 1H), 8.33 (dd, J 8.2, 1.4 Hz, 1H), 8.20 (d, J 7.8 Hz, 1H), 7.63 (t, J 7.8 Hz, 1H), 2.77-2.89 (m, 3H), 1.34 (s, 9H).

Intermediate 2

(NE)-N-[1-(3-Aminophenyl)ethylidene]-2-methylpropane-2-sulfinamide

To a solution of Raney-Ni (20.1 g, 234 mmol) in MeOH (1.0 L) was added Intermediate 1 (100 g, 372 mmol). The mixture was stirred at 25° C. for 24 h under $H_2$ (15 psi), then filtered. The filtrate was concentrated to give the title compound (88 g, crude) as a yellow oil, which was used without further purification. $\delta_H$ (400 MHz, $CDCl_3$) 7.15-7.24 (m, 1H), 6.79 (d, J 7.2 Hz, 1H), 3.80 (br s, 2H), 2.70 (s, 3H), 1.30 (s, 9H).

Intermediate 3

Benzyl N-(3-{(E)-N—[(R)-tert-butylsulfinyl]-C-methylcarbonimidoyl}phenyl)carbamate To a solution of Intermediate 2 (100 g, 419 mmol) in THF (1.0 L) were added DIPEA (108 g, 839 mmol) and benzyl chloroformate (107 g, 629 mmol) at 0° C. The mixture was stirred at 25° C. for 16 h. Water (1 L) was added and the mixture was extracted with ethyl acetate (3×1 L). The combined organic layers were dried over $Na_2SO_4$ and concentrated. The residue was purified by silica gel chromatography (5:1 petroleum ether:ethyl acetate) to give the title compound (116 g, 74%) as a yellow oil. $\delta_H$ (400 MHz, $CDCl_3$) 7.89 (br s, 1H), 7.51-7.65 (m, 2H), 7.30-7.45 (m, 6H), 6.90-7.02 (m, 1H), 5.21 (s, 2H), 2.73 (s, 3H), 1.31 (s, 9H).

Intermediate 4

Methyl (3S)-3-[3-(benzloxycarbonylamino)phenyl]-3-{[(R)-tert-butylsulfinyl]amino}-butanoate A mixture of Zn (181 g, 2.78 mol) and CuCl (27.5 g, 277 mmol) in dry THF (1.0 L) was heated under reflux (70° C.) for 0.5 h. Methyl 2-bromoacetate (85.0 g, 555 mmol) in dry THF (400 mL) was added dropwise to maintain a gentle reflux (70° C.). The mixture was cooled to 0° C., then a solution of Intermediate 3 (103 g, 277 mmol) in dry THF (400 mL) was added at 0° C. in one portion. The mixture was stirred at 25° C. for 5.5 h. Water (2 L) was added, then the mixture was filtered and the filter cake was washed with ethyl acetate (2×1 L). The filtrate was extracted with ethyl acetate (3×1 L). The combined organic layers were washed with brine (1 L), then dried over $Na_2SO_4$ and concentrated. The residue was purified by silica gel chromatography (1:1 petroleum ether:ethyl acetate; $R_f$ 0.1) to give the title compound (100 g, 80%) as a yellow solid. $\delta_H$ (400 MHz, $CDCl_3$) 7.53 (br s, 1H), 7.18-7.41 (m, 7H), 6.96-7.06 (m, 1H), 6.20 (s, 1H), 5.17 (s, 2H), 3.58 (s, 3H), 3.00-3.24 (m, 2H), 1.80 (s, 3H), 1.36 (s, 9H).

Intermediate 5

Methyl (3S)-3-amino-3-[3-(benzloxycarbonylamino) phenyl]butanoate

To a solution of Intermediate 4 (150 g, 335 mmol) in MeOH (1.3 L) was added HCl in MeOH (4.5M, 223.93 mL) at 0° C. The mixture was stirred at 25° C. for 0.5 h, then concentrated. The residue was quenched with saturated aqueous $Na_2CO_3$ solution (1.5 L) and ethyl acetate (1.5 L), then the mixture was extracted with ethyl acetate (3×1 L). The combined organic layers were washed with brine (500 mL), then dried over $Na_2SO_4$ and concentrated, to give the title compound (60 g, 52%) as a yellow oil. $\delta_H$ (400 MHz, $CDCl_3$) 7.47 (br s, 1H), 7.29-7.41 (m, 6H), 7.21-7.27 (m, 1H), 7.02-7.12 (m, 2H), 5.17 (s, 2H), 3.54 (s, 3H), 2.77-2.93 (m, 4H), 1.53 (s, 3H).

Intermediate 6 tert-Butyl (NE)-N-{(4S)-4-[3-(benzyloxycarbonylamino)phenyl]-1,4-dimethyl-6-oxo-hexahydropyrimidin-2-ylidene}carbamate To a solution of Intermediate 5 (180 g, 525 mmol) and tert-butyl N-(methyl-carbamothioyl)carbamate (100 g, 525 mmol) in DMF (2.20 L) were added EDCI (120 g, 630 mmol) and DIPEA (81.5 g, 630 mmol) at 25° C. The mixture was stirred at 25° C. for 16 h. Water (2.5 L) was added and the mixture was extracted with ethyl acetate (3×1.5 L). The combined organic layers were washed with brine (500 mL), then dried over $Na_2SO_4$ and concentrated. The residue was purified by column chromatography (3:1→0:1 petroleum ether:ethyl acetate; $R_f$ 0.43) to give the title compound (118 g, 48%) as a white solid. $\delta_H$ (400 MHz, $CDCl_3$) 10.29 (s, 1H), 7.25-7.41 (m, 7H), 6.98 (d, J 7.2 Hz, 1H), 6.75 (s, 1H), 5.18 (s, 2H), 3.12-3.21 (m, 4H), 2.81-2.88 (m, 1H), 1.64 (s, 3H), 1.54 (s, 9H).

Intermediate 7 tert-Butyl (NE)-N-[(4S)-4-(3-aminophenyl)-1,4-dimethyl-6-oxohexahydropyrimidin-2-ylidene]carbamate To a solution of Intermediate 6 (59.0 g, 126 mmol) in MeOH (1.20 L) was added Pd/C (12.00 g) at 25° C. The mixture was stirred at 25° C. for 16 h under $H_2$ at 15 psi. The mixture was filtered through celite and washed with MeOH (1 L), then the filtrate was concentrated. The residue was treated with a mixture of petroleum ether/ethyl acetate (1:1, 300 mL), and the mixture was filtered. The filter cake was dried at 45° C. under vacuum to give the title compound (27.5 g, 65%) as a white solid. $\delta_H$ (400 MHz, $CDCl_3$) 10.27 (br s, 1H), 7.13 (t, J 7.8 Hz, 1H), 6.66 (d, J 7.8 Hz, 1H), 6.54-6.61 (m, 2H), 3.72 (br s, 2H), 3.21 (s, 3H), 3.17 (d, J 16.0 Hz, 1H), 2.83 (d, J 16.0 Hz, 1H), 1.63 (s, 3H), 1.55 (s, 9H). MS (ES+) 333 MH$^+$.

Intermediate 8

(NE)-N-[1-(3-Bromophenyl)ethylidene]-2-methyl-propane-2-sulfinamide

To a solution of 1-(3-bromophenyl)ethanone (400 g, 2.01 mol) in THF (2.0 L) were added (R)-2-methylpropane-2-sulfinamide (267.9 g, 2.21 mmol) and tetraethyl titanate (2300 g, 10.1 mol). The reaction mixture was stirred at 80° C. for 22 h, then poured into brine (4 L) and filtered. The filter cake was washed with EtOAc (4×500 mL). The filtrate was combined, washed with brine (2×600 mL) and dried over $Na_2SO_4$, then filtered and concentrated, to afford the title compound (548 g), which was used without further purification. $\delta_H$ (400 MHz, $CDCl_3$) 7.99 (br s, 1H), 7.78 (d, J 7.6 Hz, 1H), 7.60 (d, J 7.6 Hz, 1H), 7.30 (t, J 8.0 Hz, 1H), 2.73 (s, 3H), 1.31 (s, 9H).

Intermediate 9

Ethyl (3S)-3-(3-bromophenyl)-3-{[(R)-tert-butylsulfinyl]amino}butanoate

Zn (802.6 g, 12.3 mol) and CuCl (260.4 g, 2.6 mol) were heated under a flow of $N_2$ gas. Dry THF (4.3 L) was added and the suspension was stirred at 80° C. for 2 h. A solution of methyl 2-bromoacetate (732.1 g, 4.38 mol) in dry THF (0.5 L) was added dropwise to maintain a gentle reflux. The mixture was cooled to 0° C. A solution of Intermediate 8 (530 g, 1.75 mol) in dry THF (0.5 L) was added in one portion. The reaction mixture was stirred at room temperature for 2.5 h, then partitioned between EtOAc (2.4 L) and aqueous citric acid solution (480 g in 3 L water). The aqueous layer was washed with EtOAc (2.4 L). The combined organic fractions were washed with water (2.4 L), saturated aqueous $NaHCO_3$ solution (2.4 L) and brine (2.4 L). The organic layer was concentrated to afford the title compound (900 g), which was used without further purification. $\delta_H$ (400 MHz, $CDCl_3$) 7.52 (br s, 1H), 7.39-7.41 (d, J 8.0 Hz, 1H), 7.30 (d, J 7.6 Hz, 1H), 7.22 (d, J 8.0 Hz, 1H), 6.20 (s, 1H), 4.03-4.14 (m, 2H), 3.25 (d, J 16.8 Hz, 1H), 3.08 (d, J 16.4 Hz, 1H), 1.83 (s, 4H), 1.40 (s, 9H), 1.18 (t, J 7.2 Hz, 3H).

Intermediate 10

Ethyl (3S)-3-amino-3-(3-bromophenyl)butanoate

To a solution of Intermediate 9 (900.0 g, 2.3 mmol) in EtOAc (900 mL) was added HCl/EtOAc (1M, 2700 mL). The reaction mixture was stirred at 10° C. for 1.5 h, then partitioned between water (1.7 L) and petroleum ether (1.7 L). The organic layer was discarded. The aqueous phase was basified with aqueous $Na_2CO_3$ solution (4M) to pH 8, then extracted with ethyl acetate (2×1.7 L). The organic layer was concentrated to afford the title compound (270.0 g, 68%) as a brown oil. $\delta_H$ (400 MHz, $CDCl_3$) 7.66 (s, 1H), 7.41 (d, J 8.0 Hz, 1H), 7.35 (d, J 10.0 Hz, 1H), 7.20 (t, J 7.6 Hz, 1H), 4.00-4.08 (m, 2H), 2.82 (d, J 15.2 Hz, 1H), 2.68 (d, J 15.2 Hz, 1H), 2.04 (br s, 2H), 1.50 (s, 3H), 1.14 (t, J 7.6 Hz, 3H).

Intermediate 11 tert-Butyl (NE)-N-[(4S)-4-(3-bromophenyl)-1,4-dimethyl-6-oxohexahydropyrimidin-2-ylidene]carbamate Intermediate 10 (130 g, 450 mmol), tert-butyl N-(methylcarbamothioyl)carbamate (99.4 g, 520 mmol), EDCI (95.8 g, 500 mmol) and DIPEA (234.8 g, 1820 mmol) were stirred in dry DMF (1.3 L) at room temperature for 23 h. The reaction mixture was poured into water (2.6 L), then extracted with ethyl acetate (2×2.6 L). The organic layer was washed with aqueous citric acid solution (2.6 L) and brine (2×1.3 L), then concentrated. The resulting yellow oil was triturated with petroleum ether and ethyl acetate (5:1, 300 mL), then the solid was filtered and dried, to afford the title compound (104 g, 58%) as a light yellow solid. $\delta_H$ (400 MHz, $CDCl_3$) 10.35 (m, 1H), 7.44-7.46 (m, 2H), 7.24-7.26 (m, 2H), 3.22 (s, 3H), 3.18 (d, J 16.4 Hz, 1H), 2.80 (d, J 16.4 Hz, 1H), 1.67 (s, 3H), 1.57 (s, 9H).

Intermediate 12 (General Method 1a)

tert-Butyl (NE)-N-[(4S)-4-{3-[(4-cyano-2-nitrophenyl)amino]phenyl}-1,4-dimethyl-6-oxotetrahydropyrimidin-2(1H)-ylidene]carbamate To a solution of Intermediate 7 (0.20 g, 0.60 mmol) in THF (15 mL) was added LiHMDS (1.80 mL, 1.80 mmol) at −78° C. The reaction mixture was stirred at −78° C. for 15 minutes, followed by dropwise addition of a solution of 4-fluoro-3-nitrobenzonitrile (0.10 g, 0.60 mmol) in THF (5 mL) at −78° C. The reaction mixture was stirred at room temperature for 16 h, then quenched with saturated aqueous $NH_4Cl$ solution (50 mL) and extracted with EtOAc (100 mL). The organic layer was separated, washed with $H_2O$ (100 mL) and brine (100 mL), then dried over anhydrous $Na_2SO_4$ and concentrated in vacuo. The crude residue was purified by column chromatography (silica 100-200 mesh, 40% EtOAc in hexanes) to afford the title compound (0.18 g, 64%) as a yellow solid. LCMS (Method 3, ES+) 479 $MH^+$, 3.41 minutes.

Intermediate 13 (General Method 1b)

tert-Butyl (NE)-N-[(4S)-4-{3-[(2-amino-4-cyanophenyl)amino]phenyl}-1,4-dimethyl-6-oxotetrahydropyrimidin-2(1H)-ylidene)carbamate To a solution of Intermediate 12 (0.18 g, 0.37 mmol) in MeOH (6 mL) were added ammonium formate (0.05 g, 0.75 mmol) and Zn dust (0.05 g, 0.75 mmol). The reaction mixture was stirred at room temperature for 2 h, then filtered through Celite and washed with EtOAc (2×50 mL). The organic layer was washed with $H_2O$ (50 mL) and brine (50 mL), then dried over anhydrous $Na_2SO_4$ and concentrated in vacuo. The crude residue was purified by column chromatography (silica 100-200 mesh, 60% EtOAc in hexanes) to afford the title compound (0.14 g, 83%) as a yellow solid. LCMS (Method 3, ES+) 449 $MH^+$, 3.17 minutes.

Intermediate 14 (General Method 1c)

tert-Butyl (NE)-N-{(4S)-4-[3-(5-cyano-2-methyl-1H-benzo[d]imidazol-1-yl)phenyl]-1,4-dimethyl-6-oxotetrahydropyrimidin-2(1H)-ylidene}carbamate To a solution of Intermediate 13 (0.14 g, 0.31 mmol) in EtOH (10 mL) were added copper(II) acetate (0.11 g, 0.62 mmol) and acetaldehyde (0.8 mL) in ethanol (10 mL). The reaction mixture was heated at 90° C. for 3 h, then concentrated in vacuo. The residue was dissolved in $H_2O$ (80 mL) and extracted with EtOAc (80 mL). The organic layer was separated, washed with $H_2O$ (100 mL) and brine (100 mL), then dried over anhydrous $Na_2SO_4$ and concentrated in vacuo. The crude residue was purified by column chromatography (silica 100-200 mesh, 90% EtOAc in hexanes) to afford the title compound (0.10 g, 71%) as a brown solid. LCMS (Method 3, ES+) 373 $[M+1-Boc]^+$, 3.04 minutes.

Intermediate 15 tert-Butyl (NE)-N-{(4S)-4-[3-(5-chloro-2-nitroanilino)phenyl]-1,4-dimethyl-6-oxo-hexahydropyrimidin-2-ylidene}carbamate Prepared from Intermediate 7 and 4-chloro-2-fluoro-1-nitrobenzene according to General Method 1a.

Intermediate 16

(6S)-6-[3-(2-Amino-5-chloroanilino)phenyl]-2-imino-3,6-dimethyl-hexahydropyrimidin-4-one Tin(II) chloride dihydrate (3.90 g, 17 mmol) was added to a solution of Intermediate 15 (1.7 g, 3.5 mmol) in ethanol (68 mL). The reaction mixture was heated to 50° C. and stirred at this temperature for 3 h. The reaction mixture was cooled to room temperature, then concentrated in vacuo. The residue was diluted with DCM (100 mL) and washed with 2M aqueous NaOH solution (100 mL). The organic layer was separated using a phase separator cartridge. The solvent was removed under reduced pressure to afford the title compound (1.0 g) as a dark oil.

Intermediate 17 tert-Butyl (NE)-N-[(4S)-4-{3-[(5-chloro-2-nitropyridin-3-yl)amino]phenyl}-1,4-dimethyl-6-oxohexahydropyrimidin-2-ylidene]carbamate Prepared from 5-chloro-3-fluoro-2-nitropyridine and Intermediate 7 according to General Method 1a. $\delta_H$ (400

MHz, CDCl$_3$) 10.29 (s, 1H), 9.21 (s, 1H), 7.81 (d, J 2.1 Hz, 1H), 7.48 (d, J 2.1 Hz, 1H), 7.43 (t, J 8.2 Hz, 1H), 7.25-7.15 (m, 3H), 3.18 (d, J 16.1 Hz, 1H), 2.89 (d, J 16.1 Hz, 1H), 1.96 (s, 3H), 1.65 (s, 3H), 1.45 (s, 9H).

Intermediate 18 (General Method 2)

tert-Butyl (NE)-N-[(4S)-4-{3-[(2-amino-5-chloro-pyridin-3-yl)amino]phenyl}-1,4-dimethyl-6-oxo-hexahydropyrimidin-2-ylidene]carbamate Tin(II) chloride dihydrate (1.43 g, 6.34 mmol) was added to a solution of Intermediate 17 (620 mg, 1.26 mmol) in ethanol (25 mL). The reaction mixture was heated at 50° C. and stirred for 4 h. The reaction mixture was cooled to room temperature, then concentrated in vacuo. The residue was diluted with DCM and washed with 2M aqueous NaOH solution, then passed through a phase separator cartridge and evaporated, to afford the title compound (358 mg), which was used without further purification.

Intermediate 19 tert-Butyl (NE)-N-{(4S)-4-[3-(5-bromo-2-nitroanilino)phenyl]-1,4-dimethyl-6-oxo-hexahydropyrimidin-2-ylidene}carbamate Prepared from 5-bromo-1-fluoro-2-nitrobenzene and Intermediate 7 according to General Method 1a. $\delta_H$ (400 MHz, CDCl$_3$) 10.40 (s, 1H), 9.45 (s, 1H), 8.37 (d, J 2.4 Hz, 1H), 7.50 (dd, J 9.2, 2.4 Hz, 1H), 7.44 (t, J 7.9 Hz, 1H), 7.27-7.15 (m, 2H), 7.12 (d, J 9.2 Hz, 1H), 3.25 (s, 3H), 2.93 (d, J 16.1 Hz, 1H), 1.71 (s, 3H), 1.55 (s, 9H).

Intermediate 20 tert-Butyl (NE)-N-{(4S)-4-[3-(2-amino-5-bromoanilino)phenyl]-1,4-dimethyl-6-oxo-hexahydropyrimidin-2-ylidene}carbamate Prepared from Intermediate 19 using General Method 2.

Intermediate 21

3-Bromo-2,5-dimethylpyrazolo[1,5-a]pyridine

To a solution of 2,5-dimethylpyrazolo[1,5-a]pyridine (0.80 g, 5.47 mmol) in DCM (20 mL) was added NBS (1.07 g, 6.02 mmol). The reaction mixture was heated at 40° C. for 3 h, then diluted with H$_2$O (100 mL) and extracted with DCM (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica 100-200 mesh, 20% EtOAc in hexanes) to afford the title compound (0.65 g, 53%) as an off-white solid. $\delta_H$ (400 MHz, CDCl$_3$) 2.38 (s, 3H) 2.43 (s, 3H), 6.53 (d, J 6.8 Hz, 1H), 7.14 (s, 1H), 8.19 (d, J 6.8 Hz, 1H).

Intermediate 22

3-Bromo-6-chloro-2-methylimidazo[1,2-a]pyridine

NBS (1.1 g, 6.0 mmol) was added to a solution of 6-chloro-2-methylimidazo[1,2-a]pyridine (1 g, 6.0 mmol) in DCM (25 mL). The reaction mixture was stirred for 2 h at room temperature. Further NBS (1.1 g, 6.0 mmol) was added to the resulting yellow solution, and the suspension was stirred vigorously. After 1 h, the reaction mixture was washed with saturated Na$_2$CO$_3$ solution and dried with Na$_2$SO$_4$, then concentrated under reduced pressure. The resulting black solid was purified by silica chromatography (gradient, 0-60% hexane/EtOAc) to afford the title compound (970 mg, 65%) as a white solid. $\delta_H$ (400 MHz, CDCl$_3$) 2.50 (s, 3H), 7.23 (dd, J 9.5, 2.0 Hz, 1H), 7.55 (dd, J, 9.5, 1.0 Hz, 1H), 8.13 (dd, J 2.0, 1.0 Hz, 1H).

Intermediate 23

3-Fluoro-N,N-dimethyl-2-nitrobenzamide

To a solution of 3-fluoro-2-nitrobenzoic acid (0.28 g, 1.51 mmol) in DCM (10 mL) were added EDCI (0.29 g, 1.51 mmol) and HOBT (0.20 g, 1.51 mmol) at 0° C. Dimethylammonium chloride (0.12 g, 1.51 mmol) and triethylamine (0.20 mL, 1.51 mmol) were added at 0° C. The reaction mixture was stirred at room temperature for 16 h, then diluted with H$_2$O (100 mL) and extracted with DCM (2×50 mL). The organic layer was separated, then washed with saturated aqueous NaHCO$_3$ solution (100 mL) and brine (100 mL). The organic layer was separated, dried over anhydrous Na$_2$SO$_4$ and concentrated in vacuo. The crude residue was purified by column chromatography (silica 100-200 mesh, 70% EtOAc in hexanes) to afford the title compound (0.25 g, 80%) as a yellow solid. $\delta_H$ (400 MHz, DMSO-d$_6$) 2.90 (s, 3H), 2.99 (s, 3H), 7.42 (d, J 7.3 Hz, 1H), 7.64-7.71 (m, 1H), 7.77-7.83 (m, 1H). LCMS (Method 3, ES+) 212.90 MH$^+$, 2.37 minutes.

Intermediate 24

2-Fluoro-N,N-dimethyl-3-nitrobenzamide

To a solution of 2-fluoro-3-nitrobenzoic acid (0.21 g, 1.13 mmol) in DCM (12 mL) were added EDCI (0.21 g, 1.13 mmol) and HOBT (0.15 g, 1.13 mmol) at 0° C. Dimethylammonium chloride (0.09 g, 1.13 mmol) and triethylamine (0.16 mL, 1.13 mmol) were added at 0° C. The reaction mixture was stirred at room temperature for 16 h, then diluted with DCM (100 mL). The organic layer was washed with H$_2$O (100 mL) and brine (100 mL). The organic layer was separated, dried over anhydrous Na$_2$SO$_4$ and concentrated in vacuo. The crude residue was purified by column chromatography (silica 100-200 mesh, 60% EtOAc in hexanes) to afford the title compound (0.18 g, 77%) as a colourless liquid. $\delta_H$ (400 MHz, CDCl$_3$) 2.98 (s, 3H), 3.18 (s, 3H), 7.36-7.43 (m, 1H), 7.68-7.74 (m, 1H), 8.09-8.17 (m, 1H).

Intermediate 25

4-Fluoro-N,N-dimethyl-3-nitrobenzamide

To a solution of 4-fluoro-3-nitrobenzoic acid (0.24 g, 1.29 mmol) in DCM (16 mL) were added EDCI (0.24 g, 1.29 mmol) and HOBT (0.17 g, 1.29 mmol) at 0° C. Dimethylammonium chloride (0.10 g, 1.29 mmol) and triethylamine (0.18 mL, 1.29 mmol) were added at 0° C. The reaction mixture was stirred at room temperature for 16 h, then quenched with H$_2$O (100 mL) and extracted with DCM (100 mL). The organic layer was washed with H$_2$O (100 mL), brine (100 mL) and saturated aqueous NaHCO$_3$ solution (100 mL). The organic layer was separated, dried over anhydrous Na$_2$SO$_4$ and concentrated in vacuo. The crude residue was purified by column chromatography (silica 100-200 mesh, 60% EtOAc in hexanes) to afford the title compound (0.16 g, 60%) as a light yellow solid. $\delta_H$ (400 MHz, CDCl$_3$) 3.05 (s, 3H), 3.15 (s, 3H), 7.37 (dd, J 10.3, 8.8 Hz, 1H), 7.76 (m, 1H), 8.17 (dd, J 6.8, 1.9 Hz, 1H).

Intermediate 26

1-(2-Fluoro-3-nitrophenyl)ethanone

Pd(dppf)Cl$_2$ (0.13 kg, 0.19 mol) was added to a solution of 1-bromo-2-fluoro-3-nitrobenzene (0.827 kg, 3.6 mol) and tributyl(1-ethoxyvinyl)tin (1.36 kg, 3.6 mol) in 1,4-dioxane (8.27 kg) at 10-30° C. under N$_2$. The solution was heated to 85-95° C. and the temperature was maintained at 85-95° C. for 4 h under N$_2$. The mixture was cooled to 10-30° C., then ethyl acetate (8.27 L) and saturated aqueous KF solution (4 L) were added. The mixture was stirred for 1 h, then the solution was filtered through a pad of celite and washed with ethyl acetate (2 L). The organic layer was separated and dried over Na$_2$SO$_4$, then concentrated. The resulting crude material was combined with two similar batches, then treated with THF (12.5 L) and 2N HCl (12.5 L). The mixture was stirred at 10-25° C. for 3 h, then extracted with ethyl acetate (3×20 L). The organic phase was separated and washed with saturated aqueous NaHCO$_3$ solution (10 L) and brine (10 L), then the solvent was concentrated. The crude residue was purified by chromatography (silica, 100-200 mesh, 4% EtOAc in petroleum ether) to give the title compound (1.70 kg, 82%). $\delta_H$ (400 MHz, CDCl$_3$) 8.21-8.13 (m, 2H), 7.42-7.38 (m, 1H), 2.71-2.69 (d, J 5.2 Hz, 3H).

Intermediate 27

(R)—(NE)-2-Methyl-N-[1-(2-fluoro-3-nitrophenyl)ethylidene]propane-2-sulfinamide (R)-(+)-2-Methyl-2-propanesulfinamide (400 g, 3.28 mmol), Intermediate 26 (500 g, 2.73 mmol) and titanium (IV) ethoxide (1.55 kg, 5.45 mol) were stirred in THF (5 L) at 60-70° C. for 16 h. Brine (1.5 L) was added, and the mixture was stirred at 25° C. for 30 minutes, then filtered. The filter cake was washed with ethyl acetate (3×15 L), then the filtrate was washed with brine (500 mL) and dried over Na$_2$SO$_4$. The organic layer was concentrated. The crude residue was purified by silica gel chromatography (20:1 petroleum ether:ethyl acetate) to give the title compound (1.2 kg, 51%). $\delta_H$ (400 MHz, DMSO-d$_6$) 8.24-8.20 (m, 1H), 8.01-7.94 (m, 1H), 7.52-7.48 (m, 1H), 2.68 (d, J 1.2 Hz, 3H), 1.19 (s, 9H).

Intermediate 28

(R)—(NE)-N-[1-(3-Amino-2-fluorophenyl)ethylidene]-2-methylpropane-2-sulfinamide

To a solution of Raney-Ni (200 g, 2.38 mol) in MeOH (8.0 L) was added Intermediate 27 (850 g, 2.97 mol). The mixture was stirred at 30-40° C. for 36 h under H$_2$ (15 psi). The filtrate was filtered and washed with MeOH (500 mL). The filtrate was concentrated to give the title compound (720 g, crude), which was used without further purification. $\delta_H$ (400 MHz, DMSO-d$_6$) 6.94-6.85 (m, 2H), 6.73-6.70 (m, 1H), 5.32 (s, 2H), 2.64 (s, 3H), 1.37 (s, 9H).

Intermediate 29

Benzyl N-(3-{(E)-N—[(R)-tert-butylsulfinyl]-C-methylcarbonimidoyl}-2-fluorophenyl)-carbamate To a solution of Intermediate 28 (720 g, 2.81 mol) in THF (7.00 L) were added DIPEA (730 g, 5.62 mol) and benzyl chloroformate (718 g, 4.22 mol) at 0° C. The mixture was stirred at 25° C. for 10 h. Water (5 L) was added and the mixture was extracted with ethyl acetate (3×6 L). The combined organic layers were dried over Na$_2$SO$_4$ and concentrated. The residue was purified by silica gel chromatography (10:1 petroleum ether:ethyl acetate) to give the title compound (860 g, 61%). $\delta_H$ (400 MHz, DMSO-d$_6$) 9.62 (s, 1H), 7.80-7.76 (m, 1H), 7.43-7.37 (m, 6H), 7.35-7.24 (m, 1H), 5.16 (s, 2H), 2.67 (s, 3H), 1.20 (s, 9H).

Intermediate 30

Methyl (3S)-3-[3-(benzyloxycarbonylamino)-2-fluorophenyl]-3-{[(R)-tert-butylsulfinyl]-amino}butanoate A mixture of Zn (293 g, 4.48 mol) and CuCl (63.4 g, 64 mmol) in dry THF (2.50 L) was heated under reflux (70° C.) for 1 h. Methyl 2-bromoacetate (190.0 g, 198 mmol) and Intermediate 29 (250 g, 64 mmol) were added at 60-70° C. and the mixture was stirred at 60-70° C. until TLC showed that most of the starting material had been consumed. Ethyl acetate (1.25 L) and a solution of citric acid (1.0 kg) in water (2.5 L) were added to the reaction mixture at 20-30° C. The two layers were separated and the aqueous layer was extracted with ethyl acetate (3×2.5 L). The combined organic layers were washed with water (1.0 L), saturated aqueous NaHCO$_3$ solution (2.0 L) and brine (2.0 L). The organic layer was concentrated under vacuum to provide the title compound (910 g, crude) as a brown oil, which was used without further purification. $\delta_H$ (400 MHz, DMSO-d$_6$) 9.38 (s, 1H), 7.60 (d, J 6 Hz, 1H), 7.39-7.33 (m, 5H), 7.32-7.27 (m, 1H), 7.17-7.07 (m, 1H), 5.11 (s, 2H), 3.43 (s, 3H), 3.11-3.02 (m, 2H), 1.73 (s, 3H), 1.12 (s, 9H) (NH signal absent).

Intermediate 31

Methyl (3S)-3-amino-3-[3-(benzyloxycarbonylamino)-2-fluorophenyl]butanoate

HCl (282 g, 7.7 mol) was added to ethyl acetate (1.8 L) at −40° C. to −30° C. A further aliquot of ethyl acetate (1.8 L) was added to the solution at 0-30° C., followed by the addition of Intermediate 30 (900 g, 1.94 mol) at 10-30° C. with stirring. The mixture was stirred at 25° C. for 3 h, then concentrated. The residue was quenched with saturated aqueous Na$_2$CO$_3$ solution (1.5 L) and ethyl acetate (2×1.5 L). The aqueous layers were combined and adjusted to pH 9-10, then extracted with ethyl acetate (4×3.6 L). The combined organic phases were concentrated. The crude residue was purified by chromatography (silica, 100-200 mesh, 0-30% ethyl acetate in dichloromethane) to give the title compound (260 g, 37%). $\delta_H$ (400 MHz, DMSO-d$_6$) 9.35 (s, 1H), 7.53 (s, 1H), 7.42-7.33 (m, 6H), 7.10-7.06 (m, 1H), 5.14 (s, 2H), 3.44 (s, 3H), 2.90 (d, J 15.2 Hz, 1H), 2.73 (d, J 14.8 Hz, 1H), 1.42 (s, 3H) (NH$_2$ signal absent owing to overlap).

Intermediate 32 tert-Butyl (NE)-N-{(4S)-4-[3-(benzyloxycarbonylamino)-2-fluorophenyl]-1,4-dimethyl-6-oxohexahydropyrimidin-2-ylidene}carbamate To a solution of tert-butyl N-(methylcarbamothioyl)carbamate (3.91 g, 20.8 mmol) in DMF (70 mL) were added Intermediate 31 (7.50 g, 20.8 mmol) and EDCI (4.77 g, 24.9 mmol), followed by the addition of DIPEA (5.50 mL, 31.2 mmol) at 0° C. The reaction mixture was stirred at room temperature for 20 h, then diluted with ice-cold H$_2$O (100 mL) and extracted with EtOAc (3×250 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, 25% EtOAc in hexanes) to afford the title compound (8.00 g, 79%) as a white solid. δ$_H$ (400 MHz, CDCl$_3$) 1.56 (s, 9H), 1.74 (s, 3H), 2.87 (d, J 16.4 Hz, 1H), 3.19 (s, 3H), 3.40 (d, J 16.4 Hz, 1H), 5.23 (s, 2H), 6.82-6.86 (m, 1H), 6.98 (br s, 1H), 7.10 (t, J 8.40 Hz, 1H), 7.33-7.41 (m, 5H), 8.10 (br s, 1H), 10.34 (s, 1H). LCMS (Method 3, ES+) 485.00 MH$^+$, 3.52 minutes.

Intermediate 33 tert-Butyl (NE)-N-[(4S)-4-(3-amino-2-fluorophenyl)-1,4-dimethyl-6-oxohexahdro-pyrimidin-2-ylidene]carbamate To a solution of Intermediate 32 (8.00 g, 16.5 mmol) in MeOH (300 mL) was added Pd/C (4.00 g) at 0° C. The reaction mixture was stirred at room temperature for 3 h under hydrogen pressure. The reaction mixture was filtered through a pad of Celite and washed with MeOH (50 mL), then the filtrate was concentrated in vacuo. The crude residue was purified by column chromatography (silica, 100-200 mesh, 30% EtOAc in hexanes) to afford the title compound (5.00 g, 86%) as a white solid. δ$_H$ (400 MHz, CDCl$_3$) 1.55 (s, 9H), 1.75 (s, 3H), 2.85 (d, J 16.0 Hz, 1H), 3.20 (s, 3H), 3.42 (d, J 16.0 Hz, 1H), 3.78 (br s, 2H), 6.50 (t, J 7.60 Hz, 1H), 6.74 (t, J 8.40 Hz, 1H), 6.87 (t, J 8.00 Hz, 1H), 10.29 (br s, 1H). LCMS (Method 3, ES+) 351 MH$^+$, 2.97 minutes.

Intermediate 34

1-Bromo-2,4-difluoro-3-nitrobenzene

To a solution of 1,3-difluoro-2-nitrobenzene (10.0 g, 62.8 mmol) in H$_2$SO$_4$ (80 mL) was added NBS (13.4 g, 75.4 mmol). The reaction mixture was heated at 80° C. for 16 h, then cooled to 0° C., poured into ice cold H$_2$O (100 mL) and extracted with EtOAc (3×100 mL). The organic layer was separated, washed with saturated aqueous NaHCO$_3$ solution (100 mL) and brine (100 mL), then dried over anhydrous Na$_2$SO$_4$ and concentrated in vacuo. The crude residue was purified by column chromatography (silica, 100-200 mesh, 2% EtOAc in hexanes) to afford the title compound (11.8 g, 79%) as a yellow liquid. δ$_H$ (400 MHz, DMSO-d$_6$) 7.53 (t, J 10.0 Hz, 1H), 8.13-8.19 (m, 1H).

Intermediate 35

1-(2,4-Difluoro-3-nitrophenyl)ethanone

To a solution of Intermediate 34 (7.00 g, 29.5 mmol) and tributyl(1-ethoxyvinyl)-tin (10.6 g, 29.5 mmol) in 1,4-dioxane (42 mL) was added Pd(PPh$_3$)$_2$Cl$_2$ (1.07 g, 1.471 mmol). The reaction mixture was purged with argon for 10 minutes, then heated at 90° C. for 5 h. The reaction mixture was cooled to room temperature, then diluted with saturated aqueous KF solution (300 mL) and EtOAc (200 mL). The reaction mixture was stirred at room temperature for 1 h, then filtered through a pad of Celite. The filtrate was washed with EtOAc (300 mL), H$_2$O (300 mL) and brine (300 mL), then dried over anhydrous Na$_2$SO$_4$ and concentrated in vacuo. The resulting crude yellow oil (9.40 g) was dissolved in THF (30 mL) and 2N HCl (20 mL) was added. The reaction mixture was stirred at room temperature for 3 h, then diluted with H$_2$O (200 mL) and extracted with EtOAc (2×200 mL). The organic layer was separated, washed with H$_2$O (200 mL) and brine (200 mL), then dried over anhydrous Na$_2$SO$_4$ and concentrated in vacuo. The crude residue was purified by column chromatography (silica, 100-200 mesh, 20% EtOAc in hexanes) to afford the title compound (6.00 g, 73%) as a yellow liquid. δ$_H$ (400 MHz, CDCl$_3$) 2.67 (s, 3H), 7.20 (t, J 10.0 Hz, 1H), 8.10-8.16 (m, 1H).

Intermediate 36

(NE)-N-[1-(2,4-Difluoro-3-nitrophenyl)ethylidene]-2-methylpropane-2-sulfinamide

To a solution of Intermediate 35 (9.00 g, 44.7 mmol) and (R)-2-methyl-2-propanesulfinamide (5.41 g, 44.7 mmol) in dry THF (120 mL) was added titanium(IV) ethoxide (20.4 g, 89.5 mmol). The reaction mixture was heated at 80° C. for 16 h, then quenched with brine (300 mL) and stirred for 30 minutes. The reaction mixture was filtered and washed with EtOAc (300 mL). The organic layer was separated, washed with H$_2$O (300 mL) and brine (300 mL), then dried over anhydrous Na$_2$SO$_4$ and concentrated in vacuo. The crude residue was purified by column chromatography (silica, 100-200 mesh, 40% EtOAc in hexanes) to afford the title compound (11.0 g, 81%) as a yellow liquid. δ$_H$ (400 MHz, CDCl$_3$) 1.31 (s, 9H), 2.79 (s, 3H), 7.16 (t, J 8.80 Hz, 1H), 7.86-7.92 (m, 1H).

Intermediate 37

(NE)-N-[1-(3-Amino-2,4-difluorophenyl)ethylidene]-2-methylpropane-2-sulfinamide

To a solution of Intermediate 36 (11.0 g, 36.1 mmol) in MeOH (150 mL) was added Raney-Ni (3.07 g, 36.1 mmol) at 0° C. The reaction mixture was stirred at room temperature for 16 h under hydrogen pressure, then filtered through Celite and washed with MeOH (100 mL). The filtrate was concentrated in vacuo. The crude residue was purified by column chromatography (silica, 100-200 mesh, 50% EtOAc in hexanes) to afford the title compound (8.00 g, 81%) as a yellow liquid. δ$_H$ (400 MHz, CDCl$_3$) 1.28 (s, 9H), 2.74 (s, 3H), 3.83 (br s, 2H), 6.84 (t, J 9.20 Hz, 1H), 6.98-7.03 (m, 1H). LCMS (Method 3, ES+) 275 MH$^+$, 2.65 minutes.

Intermediate 38

Benzyl N-(3-{(E)-N—[(R)-tert-butylsulfinyl]-C-methylcarbonimidoyl}-2,6-difluoro-phenyl)carbamate To a solution of Intermediate 37 (8.00 g, 29.1 mmol) in THF (50 mL) were added DIPEA (10.3 mL, 58.3 mmol) and benzyl chloroformate (7.40 g, 43.7 mmol) at 0° C. The reaction mixture was stirred at room temperature for 24 h, then quenched with H₂O (200 mL) and extracted with EtOAc (2×300 mL). The organic layer was separated, washed with H₂O (500 mL) and brine (500 mL), then dried over anhydrous Na₂SO₄ and concentrated in vacuo. The crude residue was purified by column chromatography (silica, 100-200 mesh, 40% EtOAc in hexanes) to afford the title compound (7.50 g, 63%) as a yellow liquid. $\delta_H$ (400 MHz, CDCl₃) 1.30 (s, 9H), 2.74 (s, 3H), 5.23 (s, 2H), 5.31 (s, 1H), 7.00 (t, J 9.60 Hz, 1H), 7.33-7.40 (m, 5H), 7.57-7.63 (m, 1H). LCMS (Method 3, ES+) 409 MH⁺, 3.13 minutes.

Intermediate 39

Methyl (3S)-3-[3-(benzyloxycarbonylamino)-2,4-difluorophenyl]-3-(tert-butylsulfinyl-amino)butanoate A suspension of CuCl (0.63 g, 6.36 mmol) and Zn (2.07 g, 31.8 mmol) in THF (20 mL) was heated at 80° C. for 30 minutes. Methyl 2-bromoacetate (1.06 mL, 9.54 mmol) in THF (5 mL) was added dropwise at 70° C. and the reaction mixture was heated at 50° C. for 40 minutes. Intermediate 38 (1.30 g, 3.18 mmol) in THF (5 mL) was added at 0° C. The reaction mixture was stirred at room temperature for 6 h, then filtered through Celite and washed with EtOAc (100 mL). The filtrate was concentrated in vacuo. The crude residue was purified by column chromatography (silica, 100-200 mesh, 60% EtOAc in hexanes) to afford the title compound (1.10 g, 72%) as a colourless semi-solid. $\delta_H$ (400 MHz, CDCl₃) 1.33 (s, 9H), 1.91 (s, 3H), 3.03 (d, J 16.8 Hz, 1H), 3.31 (d, J 16.4 Hz, 1H), 3.58 (s, 3H), 5.23 (s, 2H), 5.31 (s, 1H), 6.23 (s, 1H), 6.98 (t, J 8.80 Hz, 1H), 7.31-7.40 (m, 6H). LCMS (Method 3, ES+) 483 MH⁺, 3.03 minutes.

Intermediate 40

Methyl (3S)-3-amino-3-[3-(benzyloxycarbonylamino)-2,4-difluorophenyl]butanoate

To a solution of Intermediate 39 (1.10 g, 2.28 mmol) in MeOH (15 mL) was added 4M HCl in 1,4-dioxane (2.30 mL) at 0° C. The reaction mixture was stirred at room temperature for 2 h, then concentrated in vacuo. The crude residue was washed with diethyl ether (2×25 mL) and dried in vacuo to afford the title compound (0.98 g, crude) as yellow viscous oil, which was used without further purification. LCMS (Method 3, ES+) 379 MH⁺, 2.08 minutes.

Intermediate 41 tert-Butyl (NE)-N-{(4S)-4-[3-(benzyloxycarbonylamino)-2,4-difluorophenyl]-1,4-dimethyl-6-oxo-hexahydropyrimidin-2-ylidene}carbamate To a solution of Intermediate 40 (0.98 g, 2.59 mmol) and tert-butyl N-(methyl-carbamothioyl)carbamate (0.49 g, 2.59 mmol) in DMF (10 mL) were added EDCI (0.73 g, 3.88 mmol) and DIPEA (1.14 mL, 6.47 mmol) at 0° C. The reaction mixture was stirred at room temperature for 24 h, then diluted with H₂O (120 mL) and extracted with EtOAc (2×80 mL). The organic layer was separated, washed with H₂O (100 mL) and brine (100 mL), then dried over anhydrous Na₂SO₄ and concentrated in vacuo. The crude residue was purified by column chromatography (silica, 100-200 mesh, 25% EtOAc in hexanes) to afford the title compound (0.50 g, 38%) as an off-white solid. $\delta_H$ (400 MHz, CDCl₃) 1.52 (s, 9H), 1.74 (s, 3H), 2.88 (d, J 16.8 Hz, 1H), 3.21 (s, 3H), 3.39 (d, J 16.0 Hz, 1H), 5.23 (s, 2H), 6.19 (s, 1H), 6.93 (t, J 8.80 Hz, 1H), 7.02-7.08 (m, 1H), 7.36-7.40 (m, 5H), 10.32 (s, 1H). LCMS (Method 3, ES+) 503 MH⁺, 3.37 minutes.

Intermediate 42 tert-Butyl (NE)-N-[(4S)-4-(3-amino-2,4-difluorophenyl)-1,4-dimethyl-6-oxo-hexahydropyrimidin-2-ylidene]carbamate To a solution of Intermediate 41 (0.50 g, 0.99 mmol) in MeOH (5 mL) was added Pd/C (0.2 g) at 0° C. The reaction mixture was stirred at room temperature for 8 h under hydrogen pressure, then filtered through Celite and washed with MeOH (50 mL). The filtrate was concentrated in vacuo. The crude residue was purified by column chromatography (silica, 100-200 mesh, 30% EtOAc in hexanes) to afford the title compound (0.30 g, 82%) as an off-white solid. $\delta_H$ (400 MHz, CDCl₃) 1.56 (s, 9H), 1.74 (s, 3H), 2.86 (d, J 16.0 Hz, 1H), 3.20 (s, 3H), 3.40 (d, J 16.4 Hz, 1H), 3.81 (s, 2H), 6.43-6.49 (m, 1H), 6.77 (t, J 9.20 Hz, 1H), 10.29 (s, 1H). LCMS (Method 3, ES+) 369.00 MH⁺, 2.92 minutes.

Intermediate 43 tert-Butyl N-[(4-methoxyphenyl)methylcarbamothioyl]carbamate

To a stirred suspension of NaH (1.64 g, 68.3 mmol) in THF (50 mL) was added tert-butyl carbamate (4.00 g, 34.1 mmol) at 0° C. The reaction mixture was stirred at 0° C. for 15 minutes. 1-(Isothiocyanatomethyl)-4-methoxybenzene (4.28 g, 23.9 mmol) in THF (20 mL) was added dropwise at 0° C. The reaction mixture was stirred at room temperature for 14 h, then quenched with cold H₂O (160 mL) and extracted with EtOAc (3×150 mL). The organic layer was separated, washed with H₂O (300 mL) and brine (300 mL), then dried over anhydrous Na₂SO₄ and concentrated in vacuo. The crude residue was purified by column chromatography (silica, 100-200 mesh, 20% EtOAc in hexanes) to afford the title compound (3.45 g, 34%) as an off-white solid. $\delta_H$ (400 MHz, CDCl₃) 1.47 (s, 9H), 3.81 (s, 3H), 4.78 (d, J 4.80 Hz, 2H), 6.90 (d, J 8.40 Hz, 2H), 7.30 (d, J 8.40 Hz, 2H), 7.91 (s, 1H), 9.88 (s, 1H).

Intermediate 44 tert-Butyl (NE)-N-{(4S)-4-[3-(benzyloxycarbonylamino)-2-fluorophenyl]-1-[(4-methoxy-phenyl)methyl]-4-methyl-6-oxohexahydropyrimidin-2-ylidene}carbamate To a solution of Intermediate 43 (3.40 g, 11.4 mmol) in DMF (40 mL) were added Intermediate 31 (4.13 g, 11.4 mmol) and EDCI (2.63 g, 13.7 mmol), followed by the addition of DIPEA (3.04 mL, 17.2 mmol). The reaction mixture was stirred at room temperature for 16 h, then quenched with H₂O (300 mL) and extracted with EtOAc (2×200 mL). The organic layer was separated, washed with H₂O (300 mL) and brine (300 mL), then dried over anhydrous Na₂SO₄ and concentrated in vacuo. The crude residue was purified by column chromatography (silica, 100-200 mesh, 40% EtOAc in hexanes) to afford the title compound (5.00 g, 74%) as an off-white solid. $\delta_H$ (400 MHz, CDCl₃) 1.55 (s, 9H), 1.71 (s, 3H), 2.87 (d, J 16.0 Hz, 1H), 3.37 (d, J 15.6 Hz, 1H), 3.76 (s, 3H), 4.95-5.07 (m, 2H), 5.23 (s, 2H), 6.67-6.70 (m, 3H), 6.91-6.95 (m, 2H), 7.08 (d, J 8.80 Hz, 2H), 7.35-7.52 (m, 5H), 8.08 (br s, 1H), 10.26 (s, 1H). LCMS (Method 3, ES+) 591 MH$^+$, 3.77 minutes.

Intermediate 45 tert-Butyl (NE)-N-[(4S)-4-(3-amino-2-fluorophenyl)-4-methyl-6-oxohexahydropyrimidin-2-ylidene]carbamate To a solution of Intermediate 44 (5.00 g, 8.47 mmol) in MeOH (45 mL) was added Pd/C (2.00 g) at 0° C. The reaction mixture was stirred at room temperature for 24 h under hydrogen pressure, then filtered through Celite and washed with MeOH (100 mL). The filtrate was concentrated in vacuo. The crude residue was purified by column chromatography (silica, 100-200 mesh, 80% EtOAc in hexanes) to afford the title compound (1.90 g, 67%) as an off-white solid. $\delta_H$ (400 MHz, CDCl$_3$) 1.49 (s, 9H), 1.78 (s, 3H), 2.83 (d, J 16.0 Hz, 1H), 3.33 (d, J 16.4 Hz, 1H), 3.81 (br s, 2H), 6.57 (t, J 6.80 Hz, 1H), 6.74-6.78 (m, 1H), 6.90 (t, J 8.00 Hz, 1H), 8.20 (br s, 1H), 9.78 (br s, 1H).

Intermediate 46

4-Fluoro-3-nitrobenzoic Acid

A stirred solution of 4-fluoro-3-nitrobenzonitrile (1.00 g, 6.02 mmol) in 70% H$_2$SO$_4$ (12 mL) was heated in a sealed tube at 120° C. for 8 h. The reaction mixture was poured into ice-cold H$_2$O (100 mL) and extracted with EtOAc (2×100 mL). The organic layer was washed with H$_2$O (100 mL) and brine (100 mL), then separated, dried over anhydrous Na$_2$SO$_4$ and concentrated in vacuo. The crude residue was purified by crystallisation with DCM:hexanes (1:10, 100 mL) to afford the title compound (0.58 g, 52%) as an off-white solid. $\delta_H$ (400 MHz, DMSO-d$_6$) 7.64-7.74 (m, 1H), 8.24-8.36 (m, 1H), 8.53-8.60 (m, 1H), 13.77 (br s, 1H).

Intermediate 47

4-Fluoro-3-nitrobenzyl Alcohol

To a solution of Intermediate 46 (1.00 g, 5.40 mmol) in THF (10 mL) was added a suspension of NaBH$_4$ (0.24 g, 5.94 mmol) in THF (10 mL) at 0° C. The reaction mixture was stirred at room temperature for 1 h. Boron trifluoride diethyl etherate (0.84 g, 5.94 mmol) was added at 0° C. The reaction mixture was stirred at room temperature for 16 h, then quenched with brine (100 mL) and extracted with EtOAc (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, 50% EtOAc in hexanes) to afford the title compound (0.80 g, 87%) as a colourless liquid. $\delta_H$ (400 MHz, CDCl$_3$) 4.78 (d, J 3.34 Hz, 2H), 7.24-7.34 (m, 1H), 7.61-7.71 (m, 1H), 8.09 (d, J 6.68 Hz, 1H) (OH signal absent).

Intermediate 48 tert-Butyl (NE)-N-[(4S)-4-{3-[4-(hydroxymethyl)-2-nitroanilino]phenyl}-1,4-dimethyl-6-oxohexahydropyrimidin-2-ylidene]carbamate Prepared from Intermediate 47 and Intermediate 7 using General Method 1a. $\delta_H$ (400 MHz, CDCl$_3$) 1.53 (s, 9H), 1.70 (s, 3H), 2.88-2.94 (m, 1H), 3.14-3.20 (m, 1H), 3.24 (s, 3H), 4.65 (d, J 5.25 Hz, 2H), 7.15 (d, J 7.63 Hz, 1H), 7.19-7.25 (m, 2H), 7.37-7.49 (m, 2H), 8.22 (s, 1H), 9.46 (s, 1H), 10.36 (br s, 1H) (OH signal absent). LCMS (Method 3, ES+) 483.85 MH$^+$, 3.23 minutes.

Intermediate 49 (General Method 5)

tert-Butyl (NE)-N-[(4S)-4-{3-[2-amino-4-(hydroxymethyl)anilino]phenyl}-1,4-dimethyl-6-oxohexahydropyrimidin-2-ylidene]carbamate To a solution of Intermediate 48 (0.60 g, 1.24 mmol) in MeOH (15 mL) was added Pd/C (0.30 g) at 0° C. The reaction mixture was stirred at room temperature for 2 h under hydrogen pressure, then filtered through a pad of Celite, washed with MeOH (50 mL) and concentrated in vacuo. The crude residue was purified by column chromatography (silica, 100-200 mesh, 80% EtOAc in hexanes) to afford the title compound (0.21 g, 37%) as an off-white solid. LCMS (Method 3, ES+) 453.90 MH$^+$, 2.87 minutes.

Intermediate 50 tert-Butyl (NE)-N-[(4S)-4-{3-[5-(hydroxymethyl)-2-methylbenzimidazol-1-yl]phenyl}-1,4-dimethyl-6-oxohexahydropyrimidin-2-ylidene]carbamate Prepared from Intermediate 49 using General Method 1c. LCMS (Method 3, ES+) 478.00 MH$^+$, 2.73 minutes.

Intermediate 51

1-(4-Fluoro-3-nitrophenyl)ethanone

To a stirred solution of 1-(4-fluorophenyl)ethanone (1.10 g, 7.97 mmol) in conc. H$_2$SO$_4$ (5 mL) was added a mixture of conc. H$_2$SO$_4$ (2 mL) and conc. HNO$_3$ (1.50 mL) dropwise at −15° C. The reaction mixture was stirred at −15° C. for 80 minutes, then poured into ice-cold H$_2$O (120 mL) and extracted with EtOAc (2×100 mL). The organic layer was washed with H$_2$O (100 mL) and brine (100 mL), then separated, dried over anhydrous Na$_2$SO$_4$ and concentrated in vacuo. The crude residue was purified by column chromatography (silica, 100-200 mesh, 40% EtOAc in hexanes) to afford the title compound (0.80 g, 55%) as an off-white solid. $\delta_H$ (400 MHz, CDCl$_3$) 2.64 (s, 3H), 7.39 (t, J 9.30 Hz, 1H), 8.20-8.26 (m, 1H), 8.57-8.66 (m, 1H).

Intermediate 52

1-(4-Fluoro-3-nitrophenyl)ethan-1-ol

To a solution of Intermediate 51 (0.40 g, 2.18 mmol) in MeOH (15 mL) was added NaBH$_4$ (0.23 g, 6.55 mmol) at 0° C. The reaction mixture was stirred at room temperature for 1 h, then quenched with ice-cold H$_2$O (100 mL) and extracted with EtOAc (2×100 mL). The organic layer was separated, washed with saturated aqueous NaHCO$_3$ solution (100 mL) and brine (100 mL), then dried over anhydrous Na$_2$SO$_4$ and concentrated in vacuo. The crude residue was purified by column chromatography (silica, 100-200 mesh, 40% EtOAc in hexanes) to afford the title compound (0.32 g, 79%) as a colourless liquid. $\delta_H$ (400 MHz, CDCl$_3$) 1.53 (d, J 6.68 Hz, 3H), 4.98 (d, J 3.81 Hz, 1H), 7.23-7.34 (m, 1H), 7.60-7.69 (m, 1H), 8.08 (d, J 6.68 Hz, 1H).

Intermediate 53 tert-Butyl (NE)-N-[(4S)-4-{3-[4-(1-hydroxyethyl)-2-nitroanilino]phenyl}-1,4-dimethyl-6-oxohexahydropyrimidin-2-ylidene]carbamate Prepared from Intermediate 52 and Intermediate 7 using General Method 1a. $\delta_H$ (400 MHz, CDCl$_3$) 1.51 (s, 3H), 1.51-1.55 (s, 9H), 1.57 (s, 3H), 2.88-2.96 (m, 1H), 3.16-3.22 (m, 1H), 3.24 (s, 3H), 4.82-4.88 (m, 1H), 7.12-7.16 (m, 4H), 7.18-7.24 (m, 2H), 7.36-7.53 (m, 2H), 8.21 (br s, 1H), 9.44 (br s, 1H), 10.28-10.40 (m, 1H).

Intermediate 54 tert-Butyl (NE)-N-[(4S)-4-{3-[2-amino-4-(1-hydroxyethyl)anilino]phenyl}-1,4-dimethyl-6-oxohexahydropyrimidin-2-ylidene]carbamate Prepared from Intermediate 53 using General Method 5. LCMS (Method 3, ES+) 468.00 MH$^+$, 2.91 minutes.

Intermediate 55 tert-Butyl (NE)-N-[(4S)-4-{3-[5-(1-hydroxyethyl)-2-methylbenzimidazol-1-yl]phenyl}-1,4-dimethyl-6-oxohexahydropyrimidin-2-lidene]carbamate Prepared from Intermediate 54 using General Method 1c. $\delta_H$ (400 MHz, CDCl$_3$) 1.52 (s, 9H), 1.57 (s, 6H), 2.51 (s, 3H), 2.96 (d, J 15.74 Hz, 1H), 3.20 (m, 1H), 3.24 (s, 3H), 5.05 (m, 1H), 7.09 (d, J 8.11 Hz, 1H), 7.33-7.39 (m, 2H), 7.46 (d, J 7.63 Hz, 1H), 7.56-7.66 (m, 1H), 7.73 (s, 1H), 10.44 (br s, 1H) (2H merged into solvent peak).

Intermediate 56 tert-Butyl (NE)-N-{(4S)-4-[3-(4-acetyl-2-nitroanilino)phenyl]-1,4-dimethyl-6-oxo-hexahydropyrimidin-2-ylidene}carbamate Prepared from Intermediate 51 and Intermediate 7 using General Method 1a. $\delta_H$ (400 MHz, CDCl$_3$) 1.52 (s, 9H), 1.58 (s, 3H), 2.59 (s, 3H), 2.93 (d, J 16.14 Hz, 1H), 3.15-3.21 (m, 1H), 3.24 (s, 3H), 7.17 (d, J 8.80 Hz, 1H), 7.22-7.28 (m, 2H), 7.46 (d, J 7.83 Hz, 1H), 8.01 (d, J 8.31 Hz, 1H), 8.84 (s, 1H), 9.85 (s, 1H), 10.38 (br s, 1H). LCMS (Method 3, ES+) 396.00 [M+H-BOC], 3.41 minutes.

Intermediate 57 tert-Butyl (NE)-N-{(4S)-4-[3-(4-acetyl-2-aminoanilino)phenyl]-1,4-dimethyl-6-oxo-hexahydropyrimidin-2-ylidene}carbamate Prepared from Intermediate 56 using General Method 1b. $\delta_H$ (400 MHz, CDCl$_3$) 1.55 (s, 9H), 1.67 (s, 3H), 2.56 (s, 3H), 2.88 (d, J 16.14 Hz, 1H), 3.18 (d, J 16.14 Hz, 1H), 3.24 (s, 3H), 6.85-6.92 (m, 2H), 7.17 (d, J 8.31 Hz, 1H), 7.24-7.34 (m, 3H), 7.42 (d, J 8.31 Hz, 1H), 7.46 (s, 1H), 10.32 (br s, 1H). LCMS (Method 3, ES+) 465.95 MH$^+$, 3.12 minutes.

Intermediate 58 tert-Butyl (NE)-N-{(4S)-4-[3-(5-acetyl-2-methylbenzimidazol-1-yl)phenyl]-1,4-dimethyl-6-oxohexahydropyrimidin-2-ylidene}carbamate Prepared from Intermediate 57 using General Method 1c. $\delta_H$ (400 MHz, CDCl$_3$) 1.26 (s, 9H), 1.51 (s, 6H), 2.71 (s, 3H), 2.97 (d, J 16.14 Hz, 1H), 3.18-3.22 (m, 1H), 3.24 (s, 3H), 7.35 (br s, 2H), 7.51 (d, J 7.83 Hz, 1H), 7.65 (d, J 7.34 Hz, 1H), 7.92 (d, J 7.34 Hz, 1H), 10.44 (br s, 1H) (2H merged into solvent peak). LCMS (Method 3, ES+) 489.85 MH$^+$, 3.01 minutes.

Intermediate 59 tert-Butyl (NE)-N-[(4S)-4-{3-[5-(1-hydroxy-1-methylethyl)-2-methylbenzimidazol-1-yl]-phenyl}-1,4-dimethyl-6-oxohexahydropyrimidin-2-ylidene]carbamate To a solution of Intermediate 58 (0.18 g, 0.36 mmol) in dry THF (10 mL) was added methylmagnesium bromide (0.61 mL, 1.84 mmol) at −78° C. The reaction mixture was stirred at −78° C. for 30 minutes, then at room temperature for 2 h. The reaction mixture was quenched with saturated aqueous NH$_4$Cl solution (100 mL) and extracted with EtOAc (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, EtOAc) to afford the title compound (0.04 g, 22%) as an off-white solid. LCMS (Method 3, ES+) 506.00 MH$^+$, 2.89 minutes.

Intermediate 60 tert-Butyl (NE)-N-{(4S)-4-[3-(4-hydroxy-2-nitroanilino)phenyl]-1,4-dimethyl-6-oxo-hexahydropyrimidin-2-ylidene}carbamate Prepared from 4-fluoro-3-nitrophenol and Intermediate 7 using General Method 1a. $\delta_H$ (400 MHz, CDCl$_3$) 1.55 (s, 9H), 1.70 (s, 3H), 2.92 (d, J 16.14 Hz, 1H), 3.21 (d, J 16.14 Hz, 1H), 3.25 (s, 3H), 7.06-7.12 (m, 2H), 7.14-7.23 (m, 3H), 7.39 (t, J 7.83 Hz, 1H), 7.67 (d, J 2.93 Hz, 1H), 9.15 (s, 1H), 10.35 (br s, 1H) (OH signal absent). LCMS (Method 3, ES+) 470.00 MH$^+$, 3.01 minutes.

Intermediate 61 tert-Butyl (NE)-N-{(4S)-4-[3-(2-amino-4-hydroxyanilino)phenyl]-1,4-dimethyl-6-oxo-hexahydropyrimidin-2-ylidene}carbamate Prepared from Intermediate 60 using General Method 5. LCMS (Method 3, ES+) 440.00 MH$^+$, 2.82 minutes.

Intermediate 62 tert-Butyl (NE)-N-{(4S)-4-[3-(5-hydroxy-2-methylbenzimidazol-1-yl)phenyl]-1,4-dimethyl-6-oxohexahydropyrimidin-2-ylidene}carbamate Prepared from Intermediate 61 using General Method 1c. LCMS (Method 3, ES+) 464.05 MH$^+$, 2.81 minutes.

Intermediate 63

1-Chloro-3-fluoro-4-nitro-2-(trifluoromethyl)benzene

To a solution of conc. H$_2$SO$_4$ (3 mL) and conc. HNO$_3$ (3 mL) was added 1-chloro-3-fluoro-2-(trifluoromethyl)benzene (1.00 g, 5.05 mmol) at 0° C. The reaction mixture was stirred at 0° C. for 30 minutes, then at room temperature for 2 h. The reaction mixture was poured into ice-cold $H_2O$ (50 mL) and extracted with EtOAc (2×50 mL). The organic layer was washed with $H_2O$ (100 mL) and brine (100 mL), then separated, dried over anhydrous $Na_2SO_4$ and concentrated in vacuo. The crude residue was purified by column chromatography (silica, 100-200 mesh, 20% EtOAc in hexanes) to afford a mixture of the title compound and 2-chloro-4-fluoro-1-nitro-3-(trifluoromethyl)benzene (1.00 g, 82%) as a yellow liquid. $\delta_H$ (400 MHz, $CDCl_3$, mixture of isomers) 7.21-7.40 (m, 1H), 7.51 (d, J 8.80 Hz, 1H), 7.95 (d, J 3.42 Hz, 1H), 8.17 (br s, 1H).

Intermediate 64 tert-Butyl (NE)-N-[(4S)-4-{3-[3-chloro-6-nitro-2-(trifluoromethyl)anilino]phenyl}-1,4-dimethyl-6-oxohexahydropyrimidin-2-ylidene]carbamate Prepared from Intermediate 63 and Intermediate 7 using General Method 1a. LCMS (Method 3, ES+) 556.00 MH+, 3.61 minutes.

Intermediate 65 tert-Butyl (NE)-N-[(4S)-4-{3-[6-amino-3-chloro-2-(trifluoromethyl)anilino]phenyl}-1,4-dimethyl-6-oxohexahydropyrimidin-2-ylidene]carbamate Prepared from Intermediate 64 using General Method 1b. LCMS (Method 3, ES+) 526.00 MH+, 3.52 minutes.

Intermediate 66 tert-Butyl (NE)-N-[(4S)-4-{3-[6-chloro-2-methyl-7-(trifluoromethyl)benzimidazol-1-yl]-phenyl}-1,4-dimethyl-6-oxohexahydropyrimidin-2-ylidene]carbamate Prepared from Intermediate 65 using General Method 1c. LCMS (Method 3, ES+) 550.00 MH+, 3.52 minutes.

Intermediate 67 tert-Butyl (NE)-N-[(4S)-1,4-dimethyl-4-{3-[2-nitro-5-(trifluoromethyl)anilino]phenyl}-6-oxohexahydro-pyrimidin-2-ylidene]carbamate Prepared from 2-fluoro-1-nitro-4-(trifluoromethyl)benzene and Intermediate 7 using General Method 1a. $\delta_H$ (400 MHz, $CDCl_3$) 1.55 (s, 9H), 1.71 (s, 3H), 2.93 (d, J 16.14 Hz, 1H), 3.18-3.22 (m, 1H), 3.24 (s, 3H), 7.04 (d, J 8.80 Hz, 1H), 7.21 (br s, 1H), 7.24-7.32 (m, 2H), 7.43 (s, 1H), 7.44-7.52 (m, 1H), 8.35 (d, J 8.80 Hz, 1H), 9.51 (br s, 1H), 10.39 (br s, 1H). LCMS (Method 3, ES+) 522.00 MH+, 3.79 minutes.

Intermediate 68 tert-Butyl (NE)-N-[(4S)-4-{3-[2-amino-5-(trifluoromethyl)anilino]phenyl}-1,4-dimethyl-6-oxohexahydropyrimidin-2-ylidene]carbamate Prepared from Intermediate 67 using General Method 1b. $\delta_H$ (400 MHz, $CDCl_3$) 1.57 (s, 9H), 1.65 (s, 3H), 2.82-2.92 (m, 1H), 3.16 (d, J 16.14 Hz, 1H), 3.23 (s, 3H), 4.08 (br s, 2H), 5.31 (br s, 1H), 6.56-6.67 (m, 2H), 6.75-6.90 (m, 2H), 7.04-7.22 (m, 2H), 7.35 (br s, 1H), 10.27 (br s, 1H). LCMS (Method 3, ES+) 492.00 MH+, 3.51 minutes.

Intermediate 69 tert-Butyl (NE)-N-[(4S)-1,4-dimethyl-4-{3-[2-methyl-6-(trifluoromethyl)benzimidazol-1-yl]phenyl}-6-oxohexahydropyrimidin-2-ylidene]carbamate Prepared from Intermediate 68 using General Method 1c. $\delta_H$ (400 MHz, $CDCl_3$) 1.50 (s, 9H), 1.75 (s, 3H), 2.51 (s, 3H), 2.96 (d, J 16.14 Hz, 1H), 3.16-3.20 (m, 1H), 3.22 (s, 3H), 7.29-7.38 (m, 3H), 7.53 (t, J 6.85 Hz, 2H), 7.61-7.69 (m, 1H), 7.82 (d, J 8.31 Hz, 1H), 10.43 (br s, 1H). LCMS (Method 3, ES+) 516.00 MH+, 3.38 minutes.

Intermediate 70

4-{3-[(2E,4S)-2-tert-Butoxycarbonylimino-1,4-dimethyl-6-oxohexahydropyrimidin-4-yl]-anilino}-3-nitrobenzoic Acid Prepared from Intermediate 46 and Intermediate 7 using General Method 1a. $\delta_H$(400 MHz, DMSO-$d_6$) 1.40 (s, 9H), 1.60 (s, 3H), 3.02 (s, 3H), 3.04-3.08 (m, 1H), 7.14 (d, J 8.80 Hz, 1H), 7.22-7.28 (m, 2H), 7.39 (s, 1H), 7.44-7.52 (m, 1H), 7.92 (dd, J 9.05, 1.71 Hz, 1H), 8.63 (d, J 1.96 Hz, 1H), 9.81 (s, 1H), 10.01 (s, 1H), 13.05 (br s, 1H) (1H merged into solvent peak). LCMS (Method 3, ES+) 398.00 [M+H-BOC]+, 1.91 minutes.

Intermediate 71

3-Amino-4-{3-[(2E,4S)-2-tert-butoxycarbonylimino-1,4-dimethyl-6-oxohexahydro-pyrimidin-4-yl] aniline}benzoic Acid Prepared from Intermediate 70 using General Method 5. $\delta_H$ (400 MHz, DMSO-$d_6$) 1.40 (s, 9H), 1.59 (s, 3H), 3.02 (s, 3H), 3.04-3.11 (m, 1H), 3.17-3.24 (m, 1H), 4.97 (br s, 2H), 6.82-6.88 (m, 2H), 6.96-7.14 (m, 3H), 7.24 (t, J 7.83 Hz, 1H), 7.33 (d, J 1.96 Hz, 1H), 7.46 (s, 1H), 10.01 (s, 1H), 12.27 (br s, 1H). LCMS (Method 3, ES+) 368.00 [M+H-BOC]+, 1.75 minutes.

Intermediate 72

1-{3-[(2E,4S)-2-tert-Butoxycarbonylimino-1,4-dimethyl-6-oxohexahydropyrimidin-4-yl]-phenyl}-2-methylbenzimidazole-5-carboxylic Acid Prepared from Intermediate 71 using General Method 1c. LCMS (Method 3, ES+) 492.00 MH+, 1.72 minutes.

Intermediate 73

2-Fluoro-3-nitrobenzoic Acid

A stirred solution of 2-fluoro-3-nitrobenzonitrile (0.60 g, 3.61 mmol) in 70% $H_2SO_4$ (15 mL) was heated at 120° C. for 12 h. The reaction mixture was poured into ice-cold $H_2O$ (100 mL) and extracted with EtOAc (2×100 mL). The organic layer was washed with $H_2O$ (100 mL) and brine (100 mL), then dried over anhydrous $Na_2SO_4$ and concentrated in vacuo. The crude residue was purified by column chromatography (silica, 100-200 mesh, 60% EtOAc in hexanes) to afford the title compound (0.55 g, 82%) as an off-white solid. $\delta_H$ (400 MHz, DMSO-d$_6$) 7.53 (t, J 8.07 Hz, 1H), 8.21 (t, J 6.85 Hz, 1H), 8.34 (t, J 7.34 Hz, 1H), 13.85 (br s, 1H).

Intermediate 74

2-Fluoro-N,N-dimethyl-3-nitrobenzamide

To a solution of Intermediate 73 (0.55 g, 2.97 mmol) in DCM (12 mL) were added EDCI (0.56 g, 2.97 mmol) and HOBT (0.40 g, 2.97 mmol) at 0° C. Dimethylamine (0.24 g, 2.97 mmol) and triethylamine (0.45 mL, 3.26 mmol) were added at 0° C. The reaction mixture was stirred at room temperature for 16 h, then quenched with H$_2$O (100 mL) and extracted with DCM (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, 70% EtOAc in hexanes) to afford the title compound (0.53 g, 84%) as an off-white solid. $\delta_H$ (400 MHz, CDCl$_3$) 2.97 (s, 3H), 3.16 (s, 3H), 7.38 (t, J 7.83 Hz, 1H), 7.69 (t, J 6.11 Hz, 1H), 8.10 (t, J 7.58 Hz, 1H).

Intermediate 75

1-(2-Fluoro-3-nitrophenyl)-N,N-dimethylmethanamine

To a solution of Intermediate 74 (0.30 g, 1.41 mmol) in THF (10 mL) was added borane THF complex (4.24 mL, 4.24 mmol). The reaction mixture was heated at 60° C. for 6 h, then quenched with H$_2$O (50 mL) and extracted with EtOAc (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, 40% EtOAc in hexanes) to afford the title compound (0.20 g, 73%) as a colourless liquid. $\delta_H$ (400 MHz, CDCl$_3$) 2.63 (s, 6H), 4.10 (s, 2H), 7.37 (t, J 7.58 Hz, 1H), 7.79-7.89 (m, 1H), 8.12 (t, J 7.34 Hz, 1H). LCMS (Method 3, ES+) 199.00 MH$^+$, 2.88 minutes.

Intermediate 76 tert-Butyl (NE)-N-[(4S)-4-{3-[2-(dimethylaminomethyl)-6-nitroanilino]phenyl}-1,4-dimethyl-6-oxohexahydropyrimidin-2-ylidene]carbamate Prepared from Intermediate 75 and Intermediate 7 using General Method 1a. $\delta_H$ (400 MHz, CDCl$_3$) 1.54 (s, 9H), 1.61 (s, 3H), 2.58 (s, 6H), 2.74-2.87 (m, 1H), 3.08 (d, J 16.14 Hz, 1H), 3.20 (s, 3H), 3.86 (s, 2H), 6.57 (br s, 1H), 6.68 (d, J 7.83 Hz, 1H), 6.88 (d, J 7.34 Hz, 1H), 7.68 (d, J 7.34 Hz, 1H), 7.99 (br s, 1H), 8.05 (d, J 7.83 Hz, 1H), 10.23 (br s, 1H) (1H merged into solvent peak). LCMS (Method 3, ES+) 511.00 MH$^+$, 3.36 minutes.

Intermediate 77 tert-Butyl (NE)-N-[(4S)-4-{3-[2-amino-6-(dimethylaminomethyl)anilino]phenyl}-1,4-dimethyl-6-oxohexahydropyrimidin-2-ylidene]carbamate Prepared from Intermediate 76 using General Method 5. $\delta_H$ (400 MHz, CDCl$_3$) 1.54 (s, 9H), 1.62 (s, 3H), 2.21 (s, 6H), 2.82 (d, J 16.14 Hz, 1H), 3.09-3.18 (m, 1H), 3.21 (s, 3H), 3.25 (s, 2H), 3.72 (s, 2H), 6.51-6.60 (m, 3H), 6.68 (d, J 6.85 Hz, 1H), 6.75 (d, J 7.83 Hz, 1H), 6.95 (t, J 7.09 Hz, 1H), 7.15 (t, J 7.09 Hz, 1H), 10.23 (br s, 1H) (NH absent owing to overlap). LCMS (Method 3, ES+) 481.00 MH$^+$, 3.61 minutes.

Intermediate 78 tert-Butyl (NE)-N-[(4S)-4-{3-[7-(dimethylaminomethyl)-2-methylbenzimidazol-1-yl]-phenyl}-1,4-dimethyl-6-oxohexahydropyrimidin-2-ylidene]carbamate Prepared from Intermediate 77 using General Method 1c. LCMS (Method 3, ES+) 505.00 MH$^+$, 3.15 minutes.

Intermediate 79 (General Method 6)

tert-Butyl (NE)-N-{(4S)-4-[3-(5-chloro-2-nitroanilino)-2-fluorophenyl]-1,4-dimethyl-6-oxohexahydropyrimidin-2-ylidene}carbamate To a solution of Intermediate 33 (0.20 g, 0.57 mmol) in THF (10 mL) was added tert-butyllithium (1.07 mL, 1.71 mmol) at −78° C. The reaction mixture was stirred at −78° C. for 30 minutes. 4-Chloro-2-fluoro-1-nitrobenzene (0.10 g, 0.57 mmol) in THF (5 mL) was added dropwise at −78° C. The reaction mixture was stirred at room temperature for 12 h, then quenched with brine (100 mL) and extracted with EtOAc (2×100 mL). The organic layer was separated, washed with H$_2$O (100 mL) and brine (100 mL), then dried over anhydrous Na$_2$SO$_4$ and concentrated in vacuo. The crude residue was purified by column chromatography (silica, 100-200 mesh, 40% EtOAc in hexanes) to afford the title compound (0.18 g, 63%) as a yellow solid. $\delta_H$ (400 MHz, CDCl$_3$) 1.55-1.60 (s, 9H), 1.83 (s, 3H), 2.93 (d, J 16.14 Hz, 1H), 3.25 (s, 3H), 3.47 (d, J 16.63 Hz, 1H), 6.85 (dd, J 9.29, 1.96 Hz, 1H), 7.04-7.13 (m, 2H), 7.21 (t, J 7.83 Hz, 1H), 7.42 (t, J 7.09 Hz, 1H), 8.21 (d, J 8.80 Hz, 1H), 9.40 (s, 1H), 10.38 (br s, 1H). LCMS (Method 3, ES+) 506.00 MH$^+$, 3.81 minutes.

Intermediate 80 tert-Butyl (NE)-N-{(4S)-4-[3-(2-amino-5-chloroanilino)-2-fluorophenyl]-1,4-dimethyl-6-oxohexahydropyrimidin-2-ylidene}carbamate Prepared from Intermediate 79 using General Method 1b. $\delta_H$ (400 MHz, CDCl$_3$) 1.57 (s, 9H), 1.81 (s, 3H), 2.91 (d, J 16.14 Hz, 1H), 3.23 (s, 3H), 3.49 (d, J 16.14 Hz, 1H), 3.82 (br s, 2H), 5.43 (br s, 1H), 6.60 (t, J 7.34 Hz, 1H), 6.68 (t, J 7.83 Hz, 1H), 6.76 (d, J 8.31 Hz, 1H), 6.93 (t, J 7.58 Hz, 1H), 7.03 (d, J 8.31 Hz, 1H), 7.14 (s, 1H), 10.34 (br s, 1H).

Intermediate 81 tert-Butyl (NE)-N-{(4S)-4-[3-(6-chloro-2-methylbenzimidazol-1-yl)-2-fluorophenyl]-1,4-dimethyl-6-oxohexahydropyrimidin-2-ylidene}carbamate Prepared as a mixture of atropisomers from Intermediate 80 using General Method 1c. LCMS (Method 3, ES+) 500.00 MH$^+$, 3.38 minutes.

Intermediate 82 tert-Butyl (NE)-N-{(4S)-4-[3-(5-chloro-4-methoxy-2-nitroanilino)-2-fluorophenyl]-1,4-dimethyl-6-oxohexahydropyrimidin-2-ylidene}carbamate Prepared from 5-chloro-1-fluoro-4-methoxy-2-nitrobenzene and Intermediate 33 using General Method 6. LCMS (Method 3, ES+) 536.00 MH$^+$, 3.75 minutes.

Intermediate 83 tert-Butyl (NE)-N-{(4S)-4-[3-(2-amino-5-chloro-4-methoxyanilino)-2-fluorophenyl]-1,4-dimethyl-6-oxohexahydropyrimidin-2-ylidene}carbamate Prepared from Intermediate 82 using General Method 1b. $\delta_H$ (400 MHz, CDCl$_3$) 1.60 (s, 9H), 1.80 (s, 3H), 2.90 (d, J 16.2 Hz, 1H), 3.23 (s, 3H), 3.48 (d, J 16.3 Hz, 1H), 3.89 (s, 2H), 3.97 (s, 1H), 5.30 (s, 2H), 6.41 (s, 1H), 6.44-6.54 (m, 2H), 6.84-6.88 (m, 1H), 7.13 (s, 1H), 10.33 (s, 1H). LCMS (Method 3, ES+) 506.00 MH$^+$, 3.45 minutes.

Intermediate 84 tert-Butyl (NE)-N-{(4S)-4-[3-(6-chloro-5-methoxy-2-methylbenzimidazol-1-yl)-2-fluorophenyl]-1,4-dimethyl-6-oxohexahydropyrimidin-2-ylidene}carbamate Prepared as a mixture of atropisomers from Intermediate 83 using General Method 1c. LCMS (Method 3, ES+) 530.00 MH$^+$, 3.26 minutes.

Intermediate 85 tert-Butyl (NE)-N-[(4S)-4-{3-[3-chloro-6-nitro-2-(trifluoromethyl)anilino]-2-fluorophenyl}-1,4-dimethyl-6-oxohexahydropyrimidin-2-ylidene]carbamate Prepared from Intermediate 63 and Intermediate 33 using General Method 6. LCMS (Method 3, ES+) 574.00 MH$^+$, 3.68 minutes.

Intermediate 86 tert-Butyl (NE)-N-[(4S)-4-{3-[6-amino-3-chloro-2-(trifluoromethyl)anilino]-2-fluorophenyl}-1,4-dimethyl-6-oxohexahydropyrimidin-2-ylidene]carbamate Prepared from Intermediate 85 using General Method 1b. LCMS (Method 3, ES+) 544.00 MH$^+$, 3.77 minutes.

Intermediate 87 tert-Butyl (NE)-N-[(4S)-4-{3-[6-chloro-2-methyl-7-(trifluoromethyl)benzimidazol-1-yl]-2-fluorophenyl}-1,4-dimethyl-6-oxohexahydropyrimidin-2-ylidene]carbamate Prepared as a mixture of atropisomers from Intermediate 86 using General Method 1c. LCMS (Method 3, ES+) 568.00 MH$^+$, 3.60 minutes.

Intermediate 88 (General Method 7)

tert-Butyl (NZ)—N-[(4S)-4-{3-[6-chloro-2-(dimethylamino)benzimidazol-1-yl]-2-fluorophenyl}-1,4-dimethyl-6-oxohexahydropyrimidin-2-ylidene]carbamate To a solution of Intermediate 80 (0.20 g, 0.42 mmol) in DCM (10 mL) was added (dichloromethylene)dimethylammonium chloride (0.14 g, 0.84 mmol). The reaction mixture was stirred at room temperature for 4 h, then diluted with H$_2$O (100 mL) and extracted with DCM (2×50 mL). The organic layer was washed with H$_2$O (50 mL) and brine (50 mL), then separated, dried over anhydrous Na$_2$SO$_4$ and concentrated in vacuo. The crude residue was purified by column chromatography (silica, 100-200 mesh, 60% EtOAc in hexanes) to afford the title compound (0.13 g, 61%, mixture of atropisomers) as an off-white solid. LCMS (Method 3, ES+) 529.00 MH$^+$, 3.44 minutes.

Intermediate 89 tert-Butyl (NE)-N-{(4S)-4-[3-(5-chloro-2-nitroanilino)-2,4-difluorophenyl]-1,4-dimethyl-6-oxohexahydropyrimidin-2-ylidene}carbamate Prepared from 4-chloro-2-fluoro-1-nitrobenzene and Intermediate 42 using General Method 6. $\delta_H$ (400 MHz, CDCl$_3$) 1.56 (s, 9H), 1.79 (s, 3H), 2.91 (d, J 16.0 Hz, 1H), 3.23 (s, 3H), 3.42 (d, J 16.0 Hz, 1H), 6.63 (d, J 2.00 Hz, 1H), 6.84-6.87 (m, 1H), 7.05 (d, J 8.80 Hz, 1H), 7.12-7.18 (m, 1H), 8.19 (d, J 8.80 Hz, 1H), 9.12 (s, 1H), 10.37 (s, 1H). LCMS (Method 3, ES+) 524.00 MH$^+$, 3.76 minutes.

Intermediate 90 tert-Butyl (NE)-N-{(4S)-4-[3-(2-amino-5-chloroanilino)-2,4-difluorophenyl]-1,4-dimethyl-6-oxohexahydropyrimidin-2-ylidene}carbamate Prepared from Intermediate 89 using General Method 1b. $\delta_H$ (400 MHz, CDCl$_3$) 1.57 (s, 9H), 1.78 (s, 3H), 2.88 (d, J 16.4 Hz, 1H), 3.23 (s, 3H), 3.41 (d, J 16.4 Hz, 1H), 3.71 (br s, 2H), 5.18 (s, 1H), 6.66 (s, 1H), 6.72 (d, J 8.80 Hz, 1H), 6.78-6.82 (m, 1H), 6.84-6.92 (m, 2H), 10.33 (s, 1H). LCMS (Method 3, ES+) 494.00 MH$^+$, 3.46 minutes.

Intermediate 91 tert-Butyl (NE)-N-{(4S)-4-[3-(6-chloro-2-methylbenzimidazol-1-yl)-2,4-difluorophenyl]-1,4-dimethyl-6-oxohexahydropyrimidin-2-ylidene}carbamate Prepared as a mixture of atropisomers from Intermediate 90 using General Method 1c. LCMS (Method 3, ES+) 518.00 MH$^+$, 3.19 minutes.

Intermediate 92 tert-Butyl (NE)-N-[(4S)-4-{2-fluoro-3-[3-fluoro-6-nitro-2-(trifluoromethyl)anilino]-phenyl}-1,4-dimethyl-6-oxohexahydropyrimidin-2-ylidene]carbamate Prepared from 1,3-difluoro-4-nitro-2-(trifluoromethyl)benzene and Intermediate 33 using General Method 6. $\delta_H$ (400 MHz, DMSO-d$_6$) 1.43 (s, 9H), 1.64 (s, 3H), 3.00 (s, 3H), 3.16 (d, J 16.8 Hz, 1H), 3.28 (d, J 16.8 Hz, 1H), 6.66 (t, J 7.20 Hz, 1H), 6.74 (t, J 8.00 Hz, 1H), 6.99 (t, J 8.00 Hz, 1H), 7.51-7.56 (m, 1H), 8.30-8.34 (m, 2H), 10.11 (s, 1H). LCMS (Method 3, ES+) 558.00 MH$^+$, 3.58 minutes.

Intermediate 93 tert-Butyl (NE)-N-[(4S)-4-{3-[6-amino-3-fluoro-2-(trifluoromethyl)anilino]-2-fluorophenyl}-1,4-dimethyl-6-oxohexahydropyrimidin-2-ylidene]carbamate Prepared from Intermediate 92 using General Method 5. $\delta_H$ (400 MHz, DMSO-d$_6$) 1.43 (s, 9H), 1.68 (s, 3H), 3.00 (s, 3H), 3.16 (d, J 16.0 Hz, 1H), 3.27-3.31 (m, 1H), 5.10 (br s, 2H), 6.08 (t, J 7.20 Hz, 1H), 6.41 (t, J 7.20 Hz, 1H), 6.85 (t, J 7.20 Hz, 1H), 7.02-7.05 (m, 1H), 7.11-7.16 (m, 1H), 7.27 (s, 1H), 10.14 (s, 1H). LCMS (Method 3, ES$^+$) 528.00 MH$^+$, 3.52 minutes.

Intermediate 94 tert-Butyl (NE)-N-[(4S)-4-{2-fluoro-3-[6-fluoro-2-methyl-7-(trifluoromethyl)-benzimidazol-1-yl]phenyl}-1,4-dimethyl-6-oxohexahydropyrimidin-2-ylidene]carbamate Prepared as a mixture of atropisomers from Intermediate 93 using General Method 1c. LCMS (Method 3, ES+) 552.00 MH$^+$, 3.43 minutes.

Intermediate 95 tert-Butyl (NE)-N-[(4S)-4-{3-[2-(dimethylamino)-6-fluoro-7-(trifluoromethyl)-benzimidazol-1-yl]-2-fluorophenyl}-1,4-dimethyl-6-oxohexahydropyrimidin-2-ylidene]-carbamate Prepared as a mixture of atropisomers from Intermediate 93 using General Method 7. LCMS (Method 3, ES+) 581.00 MH$^+$, 3.55 minutes.

Intermediate 96 tert-Butyl (NE)-N-[(4S)-4-{2-fluoro-3-[3-fluoro-6-nitro-2-(trifluoromethyl)anilino]-phenyl}-4-methyl-6-oxohexahydropyrimidin-2-ylidene]carbamate Prepared from 1,3-difluoro-4-nitro-2-(trifluoromethyl)benzene and Intermediate 45 using General Method 6. $\delta_H$ (400 MHz, CDCl$_3$) 1.50 (s, 9H), 1.79 (s, 3H), 2.87 (d, J 16.8 Hz, 1H), 3.29 (d, J 16.4 Hz, 1H), 6.84-6.88 (m, 1H), 6.95-7.03 (m, 4H), 8.05 (s, 1H), 8.26-8.30 (m, 1H), 9.90 (br s, 1H). LCMS (Method 3, ES+) 544.00 MH$^+$, 3.28 minutes.

Intermediate 97 tert-Butyl (NE)-N-[(4S)-4-{3-[6-amino-3-fluoro-2-(trifluoromethyl)anilino]-2-fluorophenyl}-4-methyl-6-oxohexahydropyrimidin-2-ylidene]carbamate Prepared from Intermediate 96 using General Method 5. $\delta_H$ (400 MHz, CDCl$_3$) 1.48 (s, 9H), 1.83 (s, 3H), 2.87 (d, J 16.8 Hz, 1H), 3.36 (d, J 16.4 Hz, 1H), 3.91 (br s, 2H), 5.30 (s, 1H), 6.31 (t, J 8.40 Hz, 1H), 6.66 (t, J 7.20 Hz, 1H), 6.57-6.61 (m, 1H), 6.88-7.02 (m, 3H), 9.92 (s, 1H). LCMS (Method 3, ES+) 514.00 MH$^+$, 3.19 minutes.

Intermediate 98 tert-Butyl (NE)-N-[(4S)-4-{2-fluoro-3-[6-fluoro-2-methyl-7-(trifluoromethyl)-benzimidazol-1-yl]phenyl}-4-methyl-6-oxohexahydropyrimidin-2-ylidene]carbamate Prepared as a mixture of atropisomers from Intermediate 97 using General Method 1c. LCMS (Method 3, ES+) 538.00 MH$^+$, 3.06 minutes.

Intermediate 99 tert-Butyl (NE)-N-[(4S)-4-{2-fluoro-3-[6-fluoro-2-oxo-7-(trifluoromethyl)-3H-benzimidazol-1-yl]phenyl}-1,4-dimethyl-6-oxohexahydropyrimidin-2-ylidene]carbamate To a solution of Intermediate 93 (0.30 g, 0.56 mmol) in THF (40 mL) were added triphosgene (0.16 g, 0.56 mmol) and triethylamine (0.14 mL, 1.42 mmol) at 0° C. The reaction mixture was stirred at room temperature for 2 h, then quenched with H$_2$O (30 mL) and extracted with DCM (3×30 mL). The organic layer was separated and washed with brine (30 mL), then dried over anhydrous Na$_2$SO$_4$ and concentrated in vacuo. The crude residue was purified by column chromatography (silica, 100-200 mesh, 50% EtOAc in hexanes) to afford the title compound (0.24 g, 76%, mixture of atropisomers) as an off-white solid. LCMS (Method 3, ES+) 554.00 MH$^+$, 2.62 minutes.

Intermediate 100 tert-Butyl N-{2-[tert-butyl(dimethyl)silyloxy]ethylcarbamothioyl}carbamate

To a solution of thiourea (1.20 g, 15.7 mmol) in THF (200 mL) was added NaH (1.70 g, 70.9 mmol) at 0° C. The reaction mixture was stirred at room temperature for 1 h, then di-tert-butyl dicarbonate (7.56 g, 34.6 mmol) was added at 0° C. The reaction mixture was stirred at room temperature for 8 h, then NaH (0.64 g, 26.7 mmol) was added at 0° C. The reaction mixture was stirred at 0° C. for 1 h, followed by the addition of trifluoroacetic anhydride (5.09 g, 24.2 mmol). The reaction mixture was stirred at 0° C. for 1 h, followed by the addition of 2-[tert-butyl(dimethyl)silyloxy]ethan-1-amine (4.24 g, 24.2 mmol). The reaction mixture was stirred at room temperature for 16 h, then quenched with ice-cold water (100 mL) and extracted with EtOAc (2×50 mL). The organic layer was separated and washed with brine (50 mL), then dried over anhydrous Na$_2$SO$_4$ and concentrated in vacuo. The crude residue was purified by column chromatography (silica, 100-200 mesh, 20% EtOAc in hexanes) to afford the title compound (6.20 g, 78%) as an off-white semi-solid. $\delta_H$ (400 MHz, DMSO-d$_6$) 0.04 (s, 6H), 0.86 (s, 9H), 1.43 (s, 9H), 3.63-3.66 (m, 2H), 3.73 (t, J 4.8 Hz, 2H), 10.08 (s, 1H), 10.66 (s, 1H).

Intermediate 101 tert-Butyl (NE)-N-[(4S)-4-[3-(benzyloxycarbonylamino)-2-fluorophenyl]-1-{2-[tert-butyl(dimethyl)silyloxy]ethyl}-4-methyl-6-oxohexahydropyrimidin-2-ylidene]carbamate To a solution of Intermediate 100 (6.20 g, 18.6 mmol) in DMF (100 mL) were added Intermediate 31 (6.70 g, 18.6 mmol) and EDCI (5.33 g, 27.9 mmol). The reaction mixture was cooled to 0° C., followed by the addition of DIPEA (4.80 g, 37.2 mmol). The reaction mixture was stirred at room temperature for 16 h, then quenched with water (100 mL) and extracted with EtOAc (3×100 mL). The organic layer was separated, washed with cold water (3×100 mL) and brine (100 mL), then dried over anhydrous $Na_2SO_4$ and concentrated in vacuo. The crude residue was purified by column chromatography (silica, 100-200 mesh, 20% EtOAc in hexanes) to afford the title compound (5.37 g, 46%) as a colourless semi-solid. $\delta_H$ (400 MHz, DMSO-$d_6$) 0.03 (s, 6H), 0.79 (s, 9H), 1.43 (s, 9H), 1.66 (s, 3H), 3.15-3.28 (m, 2H), 3.42-3.54 (m, 2H), 3.70-3.78 (m, 1H), 3.88-3.92 (m, 1H), 5.15 (s, 2H), 6.91-6.96 (m, 1H), 7.11-7.17 (m, 1H), 7.33-7.40 (m, 5H), 7.66-7.72 (m, 1H), 9.54 (s, 1H), 10.28 (s, 1H). LCMS (Method 3, ES+) 629.00 $MH^+$, 4.38 minutes.

Intermediate 102 tert-Butyl (NE)-N-[(4S)-4-(3-amino-2-fluorophenyl)-1-{2-[tert-butyl(dimethyl)silyloxy]-ethyl}-4-methyl-6-oxohexahydropyrimidin-2-ylidene]carbamate To a solution of Intermediate 101 (5.30 g, 8.43 mmol) in MeOH (200 mL) was added Pd/C (2.00 g) at 0° C. The reaction mixture was stirred at room temperature for 2 h under hydrogen pressure, then filtered through Celite and washed with MeOH (3×25 mL). The filtrate was concentrated in vacuo. The crude residue was purified by column chromatography (silica, 100-200 mesh, 30% EtOAc in hexanes) to afford the title compound (1.20 g, 29%) as a colourless liquid. $\delta_H$ (400 MHz, $CDCl_3$) 0.04 (s, 6H), 0.85 (s, 9H), 1.53 (s, 9H), 1.75 (s, 3H), 2.86 (d, J 16.4 Hz, 1H), 3.36 (d, J 16.0 Hz, 1H), 3.57-3.61 (m, 2H), 3.78 (s, 2H), 3.92-4.00 (m, 1H), 4.09-4.16 (m, 1H), 6.54 (t, J 8.0 Hz, 1H), 6.74 (t, J 8.0 Hz, 1H), 6.88 (t, J 8.0 Hz, 1H), 10.26 (s, 1H). LCMS (Method 3, ES+) 495.00 $MH^+$, 4.11 minutes.

Intermediate 103 tert-Butyl N-(ethylcarbamothioyl)carbamate

To a stirred suspension of NaH (3.80 g, 95.4 mmol) in DMF (30 mL) were added tert-butyl carbamate (10.0 g, 85.4 mmol) and isothiocyanatoethane (7.40 mL, 85.4 mmol) solution in DMF (50 mL) dropwise at 0° C. The reaction mixture was stirred at 0° C. for 1 h, then at room temperature for 16 h. The reaction mixture was quenched with water (200 mL) and extracted with EtOAc (2×200 mL). The organic layer was separated, washed with water (200 mL) and brine (200 mL), then dried over anhydrous $Na_2SO_4$ and concentrated in vacuo. The crude residue was purified by column chromatography (silica, 100-200 mesh, 10% EtOAc in hexanes) to afford the title compound as an off-white solid. $\delta_H$ (400 MHz, $CDCl_3$) 1.33 (t, J 7.2 Hz, 3H), 1.50 (s, 9H), 3.68 (q, J 7.2 Hz, 2H), 7.85 (s, 1H), 9.64 (s, 1H).

Intermediate 104 tert-Butyl (NE)-N-[(4S)-4-(3-amino-2-fluorophenyl)-1-ethyl-4-methyl-6-oxohexahydro-pyrimidin-2-ylidene]carbamate Prepared from Intermediate 31 and Intermediate 103 following the experimental procedure utilised for the preparation of Intermediate 33. $\delta_H$ (400 MHz, $CDCl_3$) 1.00 (t, J 6.8 Hz, 3H), 1.56 (s, 9H) 1.75 (s, 3H), 2.84 (d, J 16.0 Hz, 1H), 3.38 (d, J 16.0 Hz, 1H), 3.78 (br s, 2H), 3.82-4.01 (m, 2H), 6.52 (t, J 7.6 Hz, 1H), 6.74 (t, J 8.0 Hz, 1H), 6.88 (t, J 8.0 Hz, 1H), 10.28 (s, 1H). LCMS (Method 3, ES+) 365.00 $MH^+$, 3.17 minutes.

Intermediate 105 tert-Butyl (NE)-N-[(4S)-4-(3-amino-4-fluorophenyl)-1,4-dimethyl-6-oxohexahydro-pyrimidin-2-ylidene]carbamate Prepared from 1-(4-fluoro-3-nitrophenyl)ethanone following the experimental procedure utilised for the preparation of Intermediate 33. $\delta_H$ (400 MHz, DMSO-$d_6$) 1.45 (s, 9H), 1.54 (s, 3H), 3.00 (s, 3H), 3.03 (d, J 15.6 Hz, 1H), 3.12 (d, J 15.6 Hz, 1H), 5.22 (br s, 2H), 6.44-6.77 (m, 1H), 6.70-6.74 (m, 1H), 6.94-6.99 (m, 1H), 9.98 (s, 1H). LCMS (Method 3, ES+) 351.00 $MH^+$, 3.12 minutes.

Intermediate 106

2-Bromo-1,3,5-trifluoro-4-nitrobenzene

To a solution of 2-bromo-1,3,5-trifluorobenzene (15.0 g, 71.4 mmol) in conc. $H_2SO_4$ (60 mL) was added conc. $HNO_3$ (60 mL) dropwise at 0° C. over 30 minutes. The reaction mixture was stirred at 0° C. for 2 h, then quenched with water (160 mL) and extracted with EtOAc (2×100 mL). The organic layer was separated, washed with $H_2O$ (200 mL) solution and brine (200 mL), then dried over anhydrous $Na_2SO_4$ and concentrated in vacuo. The crude residue was purified by column chromatography (silica, 100-200 mesh, 15% EtOAc in hexanes) to afford the title compound (16.5 g, 91%) as a yellow oil. $\delta_H$ (400 MHz, $CDCl_3$) 6.99-7.05 (m, 1H).

Intermediate 107

1-(2,4,6-Trifluoro-3-nitrophenyl)ethanone

Prepared from Intermediate 106 following the reaction conditions described for Intermediate 26. $\delta_H$ (400 MHz, $CDCl_3$) 2.62 (s, 3H), 6.94-6.99 (m, 1H).

Intermediate 108 tert-Butyl (NE)-N-[(4S)-4-(3-amino-2,4,6-trifluorophenyl)-1,4-dimethyl-6-oxohexahydro-pyrimidin-2-ylidene]carbamate Prepared from Intermediate 107 following the reaction conditions described for Intermediate 33. $\delta_H$ (400 MHz, $CDCl_3$) 1.53 (s, 9H), 1.79 (s, 3H), 2.83 (d, J 16.4 Hz, 1H), 3.22 (s, 3H), 3.53 (d, J 16.0 Hz, 1H), 3.61 (s, 2H), 6.61-6.67 (m, 1H), 10.42 (s, 1H). LCMS (Method 3, ES+) 387.00 $MH^+$, 3.21 minutes.

Intermediate 109 tert-Butyl (NE)-N-[(4S)-1-{2-[tert-butyl(dimethyl)silyloxy]ethyl}-4-{2-fluoro-3-[3-fluoro-6-nitro-2-(trifluoromethyl)anilino]phenyl}-4-methyl-6-oxohexahydropyrimidin-2-ylidene]carbamate Prepared from 1,3-difluoro-4-nitro-2-(trifluoromethyl)benzene and Intermediate 102 using General Method 6. $\delta_H$ (400 MHz, CDCl$_3$) 0.03 (s, 6H), 0.85 (s, 9H), 1.53 (s, 9H), 1.77 (s, 3H), 2.89 (d, J 16.0 Hz, 1H), 3.36 (d, J 16.0 Hz, 1H), 3.57-3.61 (m, 2H), 3.92-3.98 (m, 1H), 4.12-4.19 (m, 1H), 6.86 (t, J 8.0 Hz, 1H), 6.91-7.02 (m, 3H), 8.08 (s, 1H), 8.27-8.31 (m, 1H), 10.32 (s, 1H). LCMS (Method 3, ES+) 702.00 MH$^+$, 4.37 minutes.

Intermediate 110 tert-Butyl (NE)-N-[(4S)-4-{3-[6-amino-3-fluoro-2-(trifluoromethyl)anilino]-2-fluorophenyl}-1-{2-[tert-butyl(dimethyl)silyloxy]ethyl}-4-methyl-6-oxohexa-hydropyrimidin-2-ylidene]carbamate Prepared from Intermediate 109 using General Method 5. LCMS (Method 3, ES+) 672.00 MH$^+$, 4.28 minutes.

Intermediate 111 tert-Butyl (NE)-N-[(4S)-1-{2-[tert-butyl(dimethyl) silyloxy]ethyl}-4-{2-fluoro-3-[6-fluoro-2-methyl-7-(trifluoromethyl)benzimidazol-1-yl]phenyl}-4-methyl-6-oxo-hexahydropyrimidin-2-ylidene]carbamate Prepared from Intermediate 110 using General Method 1c. $\delta_H$ (400 MHz, DMSO-d$_6$, mixture of atropisomers) 0.03 (s, 6H), 0.82 (s, 9H), 1.38 (s, 9H), 1.69 (s, 3H), 2.21 (s, 3H), 3.22 (d, J 16.4 Hz, 1H), 3.36-3.42 (m, 3H), 3.76-3.86 (m, 2H), 7.32-7.41 (m, 1H), 7.43-7.49 (m, 2H), 7.69-7.73 (m, 1H), 7.99-8.02 (m, 1H), 10.19 (s, 1H).

Intermediate 112 tert-Butyl (NZ)—N-[(4S)-1-{2-[tert-butyl(dimethyl) silyloxy]ethyl}-4-[3-(5-chloro-2-nitro-anilino)-2-fluorophenyl]-4-methyl-6-oxohexahydropyrimidin-2-ylidene]carbamate Prepared from 4-chloro-2-fluoro-1-nitrobenzene and Intermediate 102 using General Method 6. $\delta_H$ (400 MHz, CDCl$_3$) 0.01 (s, 6H), 0.86 (s, 9H), 1.55 (s, 9H), 1.81 (s, 3H), 2.92 (d, J 16.0 Hz, 1H), 3.41 (d, J 16.4 Hz, 1H), 3.58-3.68 (m, 2H), 4.16-4.20 (m, 2H), 6.82-6.85 (m, 1H), 7.09-7.14 (m, 2H), 7.20 (t, J 8.0 Hz, 1H), 7.41 (t, J 7.2 Hz, 1H), 8.20 (d, J 8.8 Hz, 1H), 9.39 (s, 1H), 10.34 (s, 1H). LCMS (Method 3, ES+) 650 MH$^+$, 4.50 minutes.

Intermediate 113 tert-Butyl (NZ)—N-[(4S)-4-[3-(2-amino-5-chloroanilino)-2-fluorophenyl]-1-{2-[tert-butyl-(dimethyl) silyloxy]ethyl}-4-methyl-6-oxohexahydropyrimidin-2-ylidene]carbamate Prepared from Intermediate 112 using General Method 1b. $\delta_H$ (400 MHz, CDCl$_3$) 0.03 (s, 6H), 0.86 (s, 9H), 1.55 (s, 9H), 1.80 (s, 3H), 2.90 (d, J 16.0 Hz, 1H), 3.41 (d, J 16.0 Hz, 1H), 3.61-3.65 (m, 2H), 3.95-3.40 (m, 1H), 4.11-4.18 (m, 1H), 5.42 (br s, 1H), 5.31 (s, 1H), 6.61-6.71 (m, 2H), 6.75 (t, J 8.4 Hz, 1H), 6.91-6.95 (m, 1H), 7.01-7.05 (m, 1H), 7.14 (d, J 2.4 Hz, 1H), 7.26-7.29 (m, 1H), 10.30 (s, 1H). LCMS (Method 3, ES+) 620.00 MH$^+$, 4.55 minutes.

Intermediate 114 tert-Butyl (NZ)—N-[(4S)-1-{2-[tert-butyl(dimethyl) silyloxy]ethyl}-4-{3-[6-chloro-2-(dimethylamino) benzimidazol-1-yl]-2-fluorophenyl}-4-methyl-6-oxohexahdro-pyrimidin-2-ylidene]carbamate Prepared as a mixture of atropisomers from Intermediate 113 and (dichloro-methylene)dimethylammonium chloride using General Method 7. LCMS (Method 3, ES+) 673.00 MH$^+$, 4.43 minutes.

Intermediate 115 tert-Butyl (NE)-N-{(4S)-4-[3-(5-chloro-2-nitroa-nilino)-2,4,6-trifluorophenyl]-1,4-dimethyl-6-oxo-hexahydropyrimidin-2-ylidene}carbamate Prepared from a mixture of 4-chloro-2-fluoro-1-nitrobenzene and Intermediate 108 using General Method 6. $\delta_H$ (400 MHz, CDCl$_3$) 1.55 (s, 9H), 1.86 (s, 3H), 2.89 (d, J 16.0 Hz, 1H), 3.26 (s, 3H), 3.56 (d, J 16.4 Hz, 1H), 6.52 (d, J 2.0 Hz, 1H), 6.84-6.93 (m, 2H), 8.19 (d, J 9.2 Hz, 1H), 8.98 (s, 1H), 10.53 (s, 1H). LCMS (Method 3, ES+) 542.00 MH$^+$, 95.3 minutes.

Intermediate 116 tert-Butyl (NE)-N-{(4S)-4-[3-(2-amino-5-chloroa-nilino)-2,4,6-trifluorophenyl]-1,4-dimethyl-6-oxo-hexahydropyrimidin-2-ylidene}carbamate Prepared from Intermediate 115 using General Method 1b. $\delta_H$ (400 MHz, CDCl$_3$) 1.53 (s, 9H), 1.84 (s, 3H), 2.87 (d, J 16.4 Hz, 1H), 3.26 (s, 3H), 3.56 (d, J 16.4 Hz, 1H), 5.02 (s, 1H), 5.30 (s, 1H), 6.52 (d, J 2.0 Hz, 1H), 6.70 (d, J 8.4 Hz, 1H), 6.76-6.86 (m, 2H), 10.49 (s, 1H). LCMS (Method 3, ES+) 512.00 MH$^+$, 3.41 minutes.

Intermediate 117 tert-Butyl (NE)-N-{(4S)-4-[3-(6-chloro-2-methyl-benzimidazol-1-yl)-2,4,6-trifluorophenyl]-1,4-dim-ethyl-6-oxohexahydropyrimidin-2-ylidene}carbamate Prepared as a mixture of atropisomers from Intermediate 116 using General Method 1c. LCMS (Method 3, ES+) 536.00 MH$^+$, 3.34 minutes.

Intermediate 118 tert-Butyl (NE)-N-[(4S)-4-{2-fluoro-3-[6-fluoro-2-methoxy-7-(trifluoromethyl)-benzimidazol-1-yl] phenyl}-1,4-dimethyl-6-oxohexahydropyrimidin-2-ylidene]carbamate To a solution of Intermediate 99 (0.24 g, 0.43 mmol) in DCM (70 mL) was added trimethyloxonium tetrafluoroborate (0.09 g, 0.65 mmol). The reaction mixture was stirred at room temperature for 2 h, then quenched with KHCO$_3$ solution (10 mL) and extracted with EtOAc (3×50 mL). The organic layer was separated and washed with brine (50 mL), then dried over anhydrous Na$_2$SO$_4$ and concentrated in vacuo. The crude residue was purified by column chromatography (silica, 100-200 mesh, 50% EtOAc in hexanes) to

Intermediate 119 tert-Butyl (NE)-N-{(4S)-4-[3-(5-chloro-2-nitroanilino)-2-fluorophenyl]-1-ethyl-4-methyl-6-oxohexahydropyrimidin-2-ylidene}carbamate Prepared from a mixture of 4-chloro-2-fluoro-1-nitrobenzene and Intermediate 104 using General Method 6. $\delta_H$ (400 MHz, CDCl$_3$) 1.03 (t, J 6.85 Hz, 3H), 1.57 (s, 9H), 1.81 (s, 3H), 2.91 (d, J 16.14 Hz, 1H), 3.42 (d, J 16.14 Hz, 1H), 3.80-3.92 (m, 1H), 4.00-4.08 (m, 1H), 6.84 (dd, J 8.80, 1.96 Hz, 1H), 7.04-7.13 (m, 2H), 7.21 (t, J 8.07 Hz, 1H), 7.41 (t, J 7.09 Hz, 1H), 8.20 (d, J 8.80 Hz, 1H), 9.40 (s, 1H), 10.37 (br s, 1H).

Intermediate 120 tert-Butyl (NE)-N-{(4S)-4-[3-(2-amino-5-chloroanilino)-2-fluorophenyl]-1-ethyl-4-methyl-6-oxohexahydropyrimidin-2-ylidene}carbamate Prepared from Intermediate 119 using General Method 1b. $\delta_H$ (400 MHz, CDCl$_3$) 1.01 (t, J 6.85 Hz, 3H), 1.56 (s, 9H), 1.79 (s, 3H), 2.87 (d, J 16.14 Hz, 1H), 3.42 (d, J 16.14 Hz, 1H), 3.85-4.03 (m, 2H), 5.42 (d, J 2.93 Hz, 1H), 6.59 (t, J 7.58 Hz, 1H), 6.67 (t, J 7.58 Hz, 1H), 6.74 (d, J 8.80 Hz, 1H), 6.92 (t, J 8.07 Hz, 1H), 7.01 (dd, J 8.56, 2.20 Hz, 1H), 7.12 (d, J 2.45 Hz, 1H), 10.31 (br s, 1H) (NH$_2$ signal absent). LCMS (Method 3, ES+) 490.00 MH$^+$, 3.83 minutes.

Intermediate 121 tert-Butyl (NE)-N-{(4S)-4-[3-(6-chloro-2-methylbenzimidazol-1-yl)-2-fluorophenyl]-1-ethyl-4-methyl-6-oxohexahydropyrimidin-2-ylidene}carbamate Prepared from Intermediate 120 using General Method 1c. LCMS (Method 3, ES+) 514.00 MH$^+$, 3.53 minutes.

Intermediate 122

2-(Difluoromethoxy)-1,3-difluorobenzene

To a solution of 2,6-difluorophenol (1.00 g, 7.69 mmol) in DMF (15 mL) and H$_2$O (2 mL) were added sodium chlorodifluoroacetate (2.33 g, 15.3 mmol) and K$_2$CO$_3$ (1.27 g, 9.22 mmol). The reaction mixture was purged with argon for 10 minutes, then heated at 100° C. for 3 h. The reaction mixture was cooled to room temperature, diluted with HCl (10 mL) and H$_2$O (10 mL), then stirred at room temperature for 1 h. The residue was extracted with diethyl ether (3×50 mL). The organic layer was separated, washed with water (50 mL) and brine (50 mL), then dried over anhydrous Na$_2$SO$_4$ and concentrated in vacuo, to afford the title compound (0.60 g crude) as a colourless liquid. $\delta_H$ (400 MHz, CDCl$_3$) 6.58 (s, 1H), 6.96-7.02 (m, 2H), 7.15-7.25 (m, 1H).

Intermediate 123

2-(Difluoromethoxy)-1,3-difluoro-4-nitrobenzene

To conc. H$_2$SO$_4$ (2 mL) was added conc. HNO$_3$ (2 mL) dropwise at −10° C., followed by dropwise addition of Intermediate 122 (0.20 g, 1.11 mmol) at −10° C. The reaction mixture was stirred at −10° C. for 30 minutes, then poured into ice and extracted with EtOAc (3×25 mL). The organic layer was separated, washed with water (20 mL) and brine (20 mL), then dried over anhydrous Na$_2$SO$_4$ and concentrated in vacuo. The crude residue was purified by column chromatography (silica, 100-200 mesh, 2% EtOAc in hexanes) to afford the title compound (0.13 g, 54%) as a yellow liquid. $\delta_H$ (400 MHz, CDCl$_3$) 6.67 (s, 1H), 7.14-7.19 (m, 1H), 8.05-8.11 (m, 1H).

Intermediate 124 tert-Butyl (NE)-N-[(4S)-4-{3-[2-(difluoromethoxy)-3-fluoro-6-nitroanilino]-2-fluorophenyl}-1,4-dimethyl-6-oxohexahydropyrimidin-2-ylidene]carbamate Prepared from Intermediate 123 and Intermediate 33 using General Method 6. $\delta_H$(400 MHz, CDCl$_3$) 1.55 (s, 9H), 1.78 (s, 3H), 2.89 (d, J 16.8 Hz, 1H), 3.21 (s, 3H), 3.43 (d, J 16.4 Hz, 1H), 6.11 (s, 1H), 6.83 (t, J 9.2 Hz, 1H), 6.97-7.10 (m, 3H), 8.18-8.21 (m, 1H), 8.99 (s, 1H), 10.35 (s, 1H). LCMS (Method 3, ES+) 556.00 MH$^+$, 3.53 minutes.

Intermediate 125 tert-Butyl (NE)-N-[(4S)-4-{3-[6-amino-2-(difluoromethoxy)-3-fluoroanilino]-2-fluorophenyl}-1,4-dimethyl-6-oxohexahydropyrimidin-2-ylidene]carbamate Prepared from Intermediate 124 using General Method 5. LCMS (Method 3, ES+) 526.00 MH$^+$, 3.37 minutes.

Intermediate 126 tert-Butyl (NE)-N-[(4S)-4-{3-[7-(difluoromethoxy)-6-fluoro-2-methylbenzimidazol-1-yl]-2-fluorophenyl}-1,4-dimethyl-6-oxohexahydropyrimidin-2-ylidene]carbamate Prepared as a mixture of atropisomers from Intermediate 125 using General Method 1c. LCMS (Method 3, ES+) 550.00 MH$^+$, 3.31 minutes and 550.00 MH$^+$, 3.35 minutes.

Intermediate 127

2-(Difluoromethyl)-1,3-difluoro-4-nitrobenzene

To conc. H$_2$SO$_4$ (10 mL) was added conc. HNO$_3$ (10 mL) dropwise at 0° C., followed by dropwise addition of 2-(difluoromethyl)-1,3-difluorobenzene (1.20 g, 7.10 mmol) at 0° C. The reaction mixture was stirred at 0° C. for 30 minutes and at room temperature for 2 h, then quenched with ice cold water (150 mL) and extracted with DCM (2×100 mL). The organic layer was separated, washed with water (100 mL) and brine (100 mL), then dried over anhydrous Na$_2$SO$_4$ and concentrated in vacuo. The crude residue was purified by column chromatography (silica, 100-200 mesh, 15% EtOAc in hexanes) to afford the title compound (0.95 g, 64%) as a colourless oil. $\delta_H$ (400 MHz, CDCl$_3$) 6.98 (s, 1H), 7.11-7.18 (m, 1H), 8.24-8.30 (m, 1H).

The heading "afford the title compound (0.09 g, 37%, mixture of atropisomers) as an off-white solid. LCMS (Method 3, ES+) 568.00 MH$^+$, 3.58 minutes." appears at the top of the page before Intermediate 119.

Intermediate 128 tert-Butyl (NE)-N-[(4S)-4-{3-[2-(difluoromethyl)-3-fluoro-6-nitroanilino]-2-fluorophenyl}-1,4-dimethyl-6-oxohexahydropyrimidin-2-ylidene]carbamate Prepared from a mixture of Intermediate 127 and Intermediate 33 using General Method 6. $\delta_H$ (400 MHz, CDCl$_3$) 1.58 (s, 9H), 1.81 (s, 3H), 2.93 (d, J 16.0 Hz, 1H), 3.24 (s, 3H), 3.46 (d, J 16.4 Hz, 1H), 6.74 (s, 1H), 6.87-6.92 (m, 2H), 7.01-7.06 (m, 2H), 8.20 (s, 1H), 8.30-8.33 (m, 1H), 10.37 (s, 1H). LCMS (Method 3, ES+) 540.00 MH$^+$, 3.49 minutes.

Intermediate 129 tert-Butyl (NE)-N-[(4S)-4-{3-[6-amino-2-(difluoromethyl)-3-fluoroanilino]-2-fluorophenyl}-1,4-dimethyl-6-oxohexahydropyrimidin-2-ylidene]carbamate Prepared from Intermediate 128 using General Method 5. $\delta_H$ (400 MHz, CDCl$_3$) 1.57 (s, 9H), 1.76 (s, 3H), 2.86 (d, J 16.4 Hz, 1H), 3.21 (s, 3H), 3.42 (d, J 16.4 Hz, 1H), 3.79 (br s, 2H), 5.86 (br s, 1H), 6.37 (t, J 8.0 Hz, 1H), 6.51 (t, J 7.2 Hz, 1H), 6.60 (t, J 7.2 Hz, 1H), 6.73-6.86 (m, 1H), 6.86-6.96 (m, 2H), 10.35 (s, 1H). LCMS (Method 3, ES+) 510.00 MH$^+$, 3.37 minutes.

Intermediate 130 tert-Butyl (NE)-N-[(4S)-4-{3-[7-(difluoromethyl)-6-fluoro-2-methylbenzimidazol-1-yl]-2-fluorophenyl}-1,4-dimethyl-6-oxohexahydropyrimidin-2-ylidene]carbamate Prepared as a mixture of atropisomers from Intermediate 129 using General Method 1c. LCMS (Method 3, ES+) 534.00 MH$^+$, 3.25 minutes.

Intermediate 131 tert-Butyl (NE)-N-[(4S)-4-{2-fluoro-3-[6-fluoro-2-(1-hydroxy-1-methylethyl)-7-(trifluoromethyl)benzimidazol-1-yl]phenyl}-1,4-dimethyl-6-oxohexahydropyrimidin-2-ylidene]carbamate To a solution of Intermediate 168 (0.40 g, 0.74 mmol) in THF (20 mL) was added n-butyllithium (1.31 mL, 2.23 mmol) at −78° C. The reaction mixture was stirred at −78° C. for 1 h, then acetone (0.20 mL) was added at −78° C. The reaction mixture was stirred at −78° C. for 10 minutes and at room temperature for 4 h, then quenched with saturated aqueous NH$_4$Cl solution (20 mL) and extracted with EtOAc (20 mL). The organic layer was separated and washed with water (2×20 mL), then dried over anhydrous Na$_2$SO$_4$ and concentrated in vacuo, to afford the title compound (0.55 g crude) as a brown solid which was utilised as such without further purification. LCMS (Method 3, ES+) 596.00 MH$^+$, 3.40 minutes.

Intermediate 132 (General Method 8)

tert-Butyl (NE)-N-[(4S)-4-{3-[6-chloro-2-(methylamino)benzimidazol-1-yl]-2-fluorophenyl}-1,4-dimethyl-6-oxohexahydropyrimidin-2-ylidene]carbamate To a solution of Intermediate 80 (0.30 g, 0.63 mmol) in THF (50 mL) was added methyl isothiocyanate (0.13 g, 1.87 mmol). The reaction mixture was heated at 45° C. for 16 h, then EDCI (0.11 g, 0.63 mmol) was added. The reaction mixture was heated at 70° C. for 2 h, then quenched with water (20 mL) and extracted with EtOAc (3×20 mL). The organic layer was separated and washed with brine (20 mL), then dried over anhydrous Na$_2$SO$_4$ and concentrated in vacuo. The crude residue was purified by column chromatography (silica, 100-200 mesh, EtOAc) to afford the title compound (0.23 g, 74%) as a brown solid. LCMS (Method 3, ES+) 515.00 MH$^+$, 3.32 and 3.36 minutes.

Intermediate 133 (General Method 9)

2-Chloro-4-fluoro-5-nitrobenzonitrile

To a solution of 2-chloro-4-fluorobenzonitrile (0.50 g, 3.22 mmol) in conc. H$_2$SO$_4$ (5 mL) was added KNO$_3$ (0.65 g, 6.45 mmol) at 0° C. The reaction mixture was stirred at 0° C. for 30 minutes and at room temperature for 2 h, then poured into ice-cold water (100 mL) and extracted with EtOAc (2×100 mL). The organic layer was separated, washed with water (100 mL) and brine (100 mL), then dried over anhydrous Na$_2$SO$_4$ and concentrated in vacuo. The crude residue was purified by column chromatography (silica, 100-200 mesh, 10% EtOAc in hexanes) to afford the title compound (0.35 g, 54%) as a yellow liquid. $\delta_H$ (400 MHz, DMSO-d$_6$) 8.29 (d, J 10.8 Hz, 1H), 8.96 (d, J 8.00 Hz, 1H).

Intermediate 134 tert-Butyl (NE)-N-{(4S)-4-[3-(5-chloro-4-cyano-2-nitroanilino)-2-fluorophenyl]-1,4-dimethyl-6-oxohexahydropyrimidin-2-ylidene}carbamate Prepared from a mixture of Intermediate 133 and Intermediate 33 using General Method 6. $\delta_H$ (400 MHz, CDCl$_3$) 1.57 (s, 9H), 1.82 (s, 3H), 2.84-2.96 (m, 1H), 3.23 (s, 3H), 3.40-3.48 (m, 1H), 6.51 (d, J 7.2 Hz, 1H), 6.74 (d, J 8.0 Hz, 1H), 6.86 (d, J 7.6 Hz, 1H), 7.21 (d, J 7.6 Hz, 1H), 7.39 (d, J 6.8 Hz, 1H), 9.69 (m, 1H), 10.39 (s, 1H). LCMS (Method 3, ES+) 531.00 MH$^+$, 3.59 minutes.

Intermediate 135 tert-Butyl (NE)-N-{(4S)-4-[3-(2-amino-5-chloro-4-cyanoanilino)-2-fluorophenyl]-1,4-dimethyl-6-oxohexahydropyrimidin-2-ylidene}carbamate Prepared from Intermediate 134 using General Method 1b. $\delta_H$ (400 MHz, CDCl$_3$) 1.57 (s, 9H), 1.80 (s, 3H), 2.91 (d, J 16.0 Hz, 1H), 3.22 (s, 3H), 3.46 (d, J 16.4 Hz, 1H), 3.77 (br s, 2H), 5.76 (s, 1H), 6.78-6.82 (m, 1H), 7.01-7.07 (m, 3H), 7.20 (s, 1H), 10.35 (s, 1H). LCMS (Method 3, ES+) 501.00 MH$^+$, 3.43 minutes.

Intermediate 136 tert-Butyl (NZ)—N-[(4S)-4-{3-[6-chloro-5-cyano-2-(dimethylamino)benzimidazol-1-yl]-2-fluorophenyl}-1,4-dimethyl-6-oxohexahydropyrimidin-2-ylidene]carbamate Prepared as a mixture of atropisomers from Intermediate 135 and (dichloro-methylene)dimethylammonium chloride using General Method 7. LCMS (Method 3, ES+) 454.00 [M+H-BOC]$^+$, 3.38 minutes.

Intermediate 137

5-Chloro-3-fluoro-2-nitrobenzonitrile

Prepared from from 3-chloro-5-fluorobenzonitrile using General Method 9. LCMS (Method 3, ES+) 242.00 [M+H+ $CH_3CN$]$^+$, 2.31 minutes.

Intermediate 138 tert-Butyl (NE)-N-{(4S)-4-[3-(5-chloro-3-cyano-2-nitroanilino)-2-fluorophenyl]-1,4-dimethyl-6-oxo-hexahydropyrimidin-2-ylidene}carbamate Prepared from a mixture of Intermediate 137 and Intermediate 33 using General Method 6. LCMS (Method 3, ES+) 531.00 MH$^+$, 3.55 minutes.

Intermediate 139 tert-Butyl (NE)-N-{(4S)-4-[3-(2-amino-5-chloro-3-cyanoanilino)-2-fluorophenyl]-1,4-dimethyl-6-oxo-hexahydropyrimidin-2-ylidene}carbamate Prepared from Intermediate 138 using General Method 5. LCMS (Method 3, ES+) 501.00 MH$^+$, 3.58 minutes.

Intermediate 140 tert-Butyl (NE)-N-{(4S)-4-[3-(2-amino-3-cyanoanilino)-2-fluorophenyl]-1,4-dimethyl-6-oxohexahydropyrimidin-2-ylidene}carbamate Prepared from Intermediate 138 using General Method 5. LCMS (Method 3, ES+) 467.00 MH$^+$, 3.37 minutes.

Intermediate 141 tert-Butyl (NZ)—N-[(4S)-4-{3-[6-chloro-4-cyano-2-(dimethylamino)benzimidazol-1-yl]-2-fluorophenyl}-1,4-dimethyl-6-oxohexahydropyrimidin-2-ylidene]carbamate Prepared from Intermediate 139 and (dichloromethylene)dimethylammonium chloride using General Method 7. LCMS (Method 3, ES+) 554.00 MH$^+$, 3.60 minutes.

Intermediate 142 tert-Butyl (NZ)—N-[(4S)-4-{3-[4-cyano-2-(dimethylamino)benzimidazol-1-yl]-2-fluorophenyl}-1,4-dimethyl-6-oxohexahydropyrimidin-2-ylidene]carbamate Prepared from Intermediate 140 and (dichloromethylene)dimethylammonium chloride using General Method 7. LCMS (Method 3, ES+) 520.00 MH$^+$, 3.34 minutes.

Intermediate 143 tert-Butyl (NZ)—N-[(4S)-4-{2-fluoro-3-[6-fluoro-2-(methylamino)-7-(trifluoromethyl)-benzimidazol-1-yl]phenyl}-1,4-dimethyl-6-oxohexahydropyrimidin-2-ylidene]carbamate Prepared as a mixture of atropisomers from Intermediate 93 using General Method 8. LCMS (Method 3, ES+) 567.00 MH$^+$, 3.28 minutes.

Intermediate 144 (General Method 10)

tert-Butyl (NE)-N-{(4S)-4-[3-(6-chloro-2-oxo-3H-benzimidazol-1-yl)-2-fluorophenyl]-1,4-dimethyl-6-oxohexahydropyrimidin-2-ylidene}carbamate To a solution of Intermediate 80 (0.50 g, 1.05 mmol) in THF (50 mL) were added triethylamine (0.43 g, 3.15 mmol) and triphosgene (0.31 g, 1.05 mmol) at 0° C. The reaction mixture was stirred at room temperature for 2 h, then concentrated in vacuo. The residue was diluted with water (30 mL) and extracted with EtOAc (2×30 mL). The organic layer was separated, dried over anhydrous $Na_2SO_4$ and concentrated in vacuo. The crude residue was purified by column chromatography (silica, 100-200 mesh, 50% EtOAc in hexanes) to afford the title compound (0.37 g, 70%) as a brown solid. LCMS (Method 3, ES+) 502.00 MH$^+$, 3.15 minutes.

Intermediate 145 (General Method 11)

(6S)-6-[3-(2,6-Dichlorobenzimidazol-1-yl)-2-fluoro-phenyl]-2-imino-3,6-dimethyl-hexahydropyrimidin-4-one A stirred solution of Intermediate 144 (0.25 g, 0.49 mmol) in $POCl_3$ (10 mL) was heated at 100° C. for 16 h, then the reaction mixture was concentrated in vacuo. The crude residue was purified by column chromatography (silica, 100-200 mesh, 20% EtOAc in hexanes) to afford the title compound (0.30 g crude) as a brown solid. LCMS (Method 3, ES+) 420.00 MH$^+$, 2.76 minutes.

Intermediate 146 tert-Butyl (NE)-N-{(4S)-4-[3-(6-chloro-2-oxo-3H-benzimidazol-1-yl)-2,4-difluoro-phenyl]-1,4-dimethyl-6-oxohexahydropyrimidin-2-ylidene}carbamate Prepared as a mixture of atropisomers from Intermediate 90 using General Method 10. LCMS (Method 3, ES+) 520.00 MH$^+$, 3.19 minutes.

Intermediate 147 tert-Butyl (NE)-N-[(4S)-4-{3-[6-chloro-2-(dimethylamino)benzimidazol-yl]-2,4-difluorophenyl}-1,4-dimethyl-6-oxohexahydropyrimidin-2-ylidene]carbamate Prepared as a mixture of atropisomers from Intermediate 90 and (dichloro-methylene)dimethylammonium chloride using General Method 7. LCMS (Method 3, ES+) 547.00 MH$^+$, 3.49 minutes.

Intermediate 148 tert-Butyl (NE)-N-[(4S)-4-{3-[3-chloro-6-nitro-2-(trifluoromethyl)anilino]-2,4-difluoro-phenyl}-1,4-dimethyl-6-oxohexahydropyrimidin-2-ylidene]carbamate Prepared from a mixture of Intermediate 42 and Intermediate 63 using General Method 6. $\delta_H$ (400 MHz, CDCl$_3$) 1.55 (s, 9H), 1.73 (s, 3H), 2.85 (d, J 16.0 Hz, 1H), 3.20 (s, 3H), 3.39 (d, J 16.0 Hz, 1H), 6.43-6.49 (m, 1H), 6.76 (t, J 8.8

Hz, 1H), 6.90 (d, J 8.0 Hz, 1H), 7.25 (d, J 8.0 Hz, 1H), 8.02 (br s, 1H), 10.30 (s, 1H). LCMS (Method 3, ES+) 592.00 MH$^+$, 3.18 minutes.

Intermediate 149 tert-Butyl (NE)-N-[(4S)-4-{3-[6-amino-3-chloro-2-(trifluoromethyl)anilino]-2,4-difluoro-phenyl}-1,4-dimethyl-6-oxohexahydropyrimidin-2-ylidene]carbamate Prepared from Intermediate 148 using General Method 1b. LCMS (Method 3, ES+) 562.00 MH$^+$, 3.57 minutes.

Intermediate 150 tert-Butyl (NE)-N-[(4S)-4-{3-[6-chloro-2-oxo-7-(trifluoromethyl)-3H-benzimidazol-1-yl]-2,4-difluorophenyl}-1,4-dimethyl-6-oxohexahdropyrimidin-2-ylidene]carbamate Prepared as a mixture of atropisomers from Intermediate 149 using General Method 10. LCMS (Method 3, ES+) 588.00 MH$^+$, 2.43 minutes.

Intermediate 151 tert-Butyl (NZ)—N-[(4S)-4-{3-[2-(benzylamino)-6-fluoro-7-(trifluoromethyl)-benzimidazol-1-yl]-2-fluorophenyl}-1,4-dimethyl-6-oxohexahydropyrimidin-2-ylidene]-carbamate To a solution of Intermediate 93 (0.50 g, 0.94 mmol) in pyridine (10 mL) was added benzyl isothiocyanate (0.42 g, 2.84 mmol). The reaction mixture was heated at 90° C. for 2 h, then EDCI (0.36 g, 1.89 mmol) was added. The reaction mixture was heated at 90° C. for 3 h, then concentrated in vacuo. The residue was diluted with water (10 mL) and extracted with EtOAc (20 mL). The organic layer was separated and washed with water (20 mL), then dried over anhydrous Na$_2$SO$_4$ and concentrated in vacuo. The crude residue was purified by column chromatography (silica, 100-200 mesh, 50% EtOAc in hexanes) to afford the title compound (0.20 g, 33%, mixture of atropisomers) as a brown solid. LCMS (Method 3, ES+) 643.00 MH$^+$, 3.46 minutes.

Intermediate 152 (General Method 12)

tert-Butyl (NZ)—N-[(4S)-4-{3-[2-cyclobutyl-6-fluoro-7-(trifluoromethyl)benzimidazol-1-yl]-2-fluorophenyl}-1,4-dimethyl-6-oxohexahydropyrimidin-2-ylidene]carbamate To a solution of Intermediate 93 (0.20 g, 0.37 mmol) in MeOH (6 mL) were added copper(II) acetate (0.13 g, 0.75 mmol) and cyclobutanecarbaldehyde (0.16 g, 1.89 mmol). The reaction mixture was heated at 80° C. for 2 h, then concentrated in vacuo. The residue was dissolved in EtOAc (100 mL). The organic layer was separated, washed with water (100 mL) and brine (100 mL), then dried over anhydrous Na$_2$SO$_4$ and concentrated in vacuo. The crude residue was purified by column chromatography (silica, 100-200 mesh, 50% EtOAc in hexanes) to afford the title compound (0.15 g, 67%, mixture of atropisomers) as a brown solid. LCMS (Method 3, ES+) 592.00 MH$^+$, 3.75 minutes.

Intermediate 153 tert-Butyl (NZ)—N-{(4S)-4-[3-(6-chloro-2-cyclobutylbenzimidazol-1-yl)-2-fluorophenyl]-1,4-dimethyl-6-oxohexahydropyrimidin-2-ylidene}carbamate Prepared as a mixture of atropisomers from Intermediate 80 using General Method 12. LCMS (Method 3, ES+) 540.00 MH$^+$, 3.67 minutes.

Intermediate 154 tert-Butyl (NZ)—N-[(4S)-4-{3-[2-cyclopropyl-6-fluoro-7-(trifluoromethyl)benzimidazol-1-yl]-2-fluorophenyl}-1,4-dimethyl-6-oxohexahydropyrimidin-2-ylidene]carbamate To a solution of Intermediate 93 (0.10 g, 0.18 mmol) in MeOH (10 mL) were added copper(II) acetate (0.07 g, 0.37 mmol) and cyclopropanecarbaldehyde (0.07 mL, 0.94 mmol). The reaction mixture was heated at 80° C. for 1 h, then concentrated in vacuo. The residue was diluted with water (10 mL) and extracted with EtOAc (3×10 mL). The organic layer was separated and washed with brine (10 mL), then dried over anhydrous Na$_2$SO$_4$ and concentrated in vacuo. The crude residue was purified by column chromatography (silica, 100-200 mesh, 50% EtOAc in hexanes) to afford the title compound (0.10 g, 91%, mixture of atropisomers) as a brown solid. LCMS (Method 3, ES+) 578.00 MH$^+$, 3.67 minutes.

Intermediate 155

(6S)-6-{3-[2-Chloro-6-fluoro-7-(trifluoromethyl)benzimidazol-1-yl]-2-fluorophenyl}-2-imino-3,6-dimethylhexahydropyrimidin-4-one Prepared as a mixture of atropisomers from Intermediate 99 using General Method 11. LCMS (Method 3, ES+) 472.00 MH$^+$, 2.84 minutes.

Intermediate 156 tert-Butyl (NE)-N-[(4S)-4-{4-fluoro-3-[3-fluoro-6-nitro-2-(trifluoromethyl)anilino]-phenyl}-1,4-dimethyl-6-oxohexahydropyrimidin-2-ylidene]carbamate Prepared from a mixture of Intermediate 105 and 1,3-difluoro-4-nitro-2-(trifluoro-methyl)benzene using General Method 6. LCMS (Method 3, ES+) 558.00 MH$^+$, 3.53 minutes.

Intermediate 157 tert-Butyl (NE)-N-[(4S)-4-{3-[6-amino-3-fluoro-2-(trifluoromethyl)anilino]-4-fluorophenyl}-1,4-dimethyl-6-oxohexahydropyrimidin-2-ylidene]carbamate Prepared from Intermediate 156 using General Method 5. LCMS (Method 3, ES+) 528.00 MH$^+$, 3.41 minutes.

Intermediate 158 tert-Butyl (NZ)—N-[(4S)-4-{3-[2-(dimethylamino)-6-fluoro-7-(trifluoromethyl)-benzimidazol-1-yl]-4-fluorophenyl}-1,4-dimethyl-6-oxohexahydropyrimidin-2-ylidene]carbamate Prepared as a mixture of atropisomers from Intermediate 157 and (dichloro-methylene)dimethylammonium chloride using General Method 7. LCMS (Method 3, ES+) 581.00 MH+, 3.51 minutes.

Intermediate 159 tert-Butyl (NE)-N-{(4S)-4-[3-(5-chloro-2-nitroanilino)-4-fluorophenyl]-1,4-dimethyl-6-oxohexahydropyrimidin-2-ylidene}carbamate Prepared from a mixture of Intermediate 105 and 4-chloro-2-fluoro-1-nitrobenzene using General Method 6. $\delta_H$ (400 MHz, DMSO-$d_6$) 1.42 (s, 9H), 1.63 (s, 3H), 3.07 (s, 3H), 3.11 (d, J 16.0 Hz, 1H), 3.31 (d, J 16.0 Hz, 1H), 6.70 (s, 1H), 6.94 (dd, J 2.00, 9.2 Hz, 1H), 7.33-7.36 (m, 1H), 7.40-7.45 (m, 1H), 7.49-7.52 (m, 1H), 8.16 (d, J 9.2 Hz, 1H), 9.42 (s, 1H) 9.97 (s, 1H). LCMS (Method 3, ES+) 506.00 MH+, 3.77 minutes.

Intermediate 160 tert-Butyl (NE)-N-{(4S)-4-[3-(2-amino-5-chloroanilino)-4-fluorophenyl]-1,4-dimethyl-6-oxohexahydropyrimidin-2-ylidene}carbamate Prepared from Intermediate 159 using General Method 1b. $\delta_H$ (400 MHz, DMSO-$d_6$) 1.40 (s, 9H), 1.53 (s, 3H), 2.99 (s, 3H), 3.02 (d, J 16.0 Hz, 1H), 3.11 (d, J 16.0 Hz, 1H), 4.88 (s, 2H), 6.65-6.73 (m, 3H), 6.81 (d, J 8.8 Hz, 2H), 7.14-7.19 (m, 2H), 9.89 (s, 1H). LCMS (Method 3, ES+) 476.00 MH+, 3.46 minutes.

Intermediate 161 tert-Butyl (NZ)—N-[(4S)-4-{3-[6-chloro-2-(dimethylamino)benzimidazol-1-yl]-4-fluorophenyl}-1,4-dimethyl-6-oxohexahydropyrimidin-2-ylidene]carbamate Prepared as a mixture of atropisomers from Intermediate 160 and (dichloro-methylene)dimethylammonium chloride using General Method 7. LCMS (Method 3, ES+) 529.00 MH+, 3.42 minutes.

Intermediate 162

1-(2-Chloro-3-nitrophenyl)ethanone

Prepared from 1-bromo-2-chloro-3-nitrobenzene following the reaction conditions described for Intermediate 26. $\delta_H$ (400 MHz, CDCl$_3$) 2.62 (s, 3H), 7.70 (t, J 8.0 Hz, 1H), 7.98 (dd, J 1.6, 8.0 Hz, 1H), 8.15 (dd, J 1.6, 8.0 Hz, 1H).

Intermediate 163 tert-Butyl (NE)-N-[(4S)-4-(3-amino-2-chlorophenyl)-1,4-dimethyl-6-oxohexahydro-pyrimidin-2-ylidene]carbamate Prepared from Intermediate 162 following the reaction conditions described for Intermediate 33. $\delta_H$ (400 MHz, DMSO-$d_6$) 1.55 (s, 9H), 1.87 (s, 3H), 2.83 (d, J 16.0 Hz, 1H), 3.19 (s, 3H), 3.76 (d, J 16.8 Hz, 1H), 4.20 (br s, 2H), 6.69 (d, J 8.0 Hz, 1H), 6.76 (d, J 8.0 Hz, 1H), 7.03 (t, J 8.0 Hz, 1H), 10.47 (s, 1H). LCMS (Method 3, ES+) 367.00 MH+, 3.18 minutes.

Intermediate 164 tert-Butyl (NE)-N-{(4S)-4-[2-chloro-3-(5-chloro-2-nitroanilino)phenyl]-1,4-dimethyl-6-oxohexahydropyrimidin-2-ylidene}carbamate Prepared from Intermediate 163 and 4-chloro-2-fluoro-1-nitrobenzene using General Method 6.

Intermediate 165 tert-Butyl (NE)-N-{(4S)-4-[3-(2-amino-5-chloroanilino)-2-chlorophenyl]-1,4-dimethyl-6-oxohexahydropyrimidin-2-ylidene}carbamate Prepared from Intermediate 164 using General Method 1b. LCMS (Method 3, ES+) 492.00 MH+, 2.2 minutes.

Intermediate 166 tert-Butyl (NE)-N-[(4S)-4-{2-chloro-3-[6-chloro-2-(pyrrolidin-1-yl)benzimidazol-1-yl]-phenyl}-1,4-dimethyl-6-oxohexahydropyrimidin-2-ylidene]carbamate Prepared as a mixture of atropisomers from Intermediate 165 and 1-(dichloro-methylene)pyrrolidinium chloride using General Method 7. LCMS (Method 3, ES+) 571.00 MH+, 2.16 minutes.

Intermediate 167 tert-Butyl (NE)-N-[(4S)-1-{2-[tert-butyl(dimethyl)silyloxy]ethyl}-4-{3-[6-chloro-2-(pyrrolidin-1-yl)benzimidazol-1-yl]-2-fluorophenyl}-4-methyl-6-oxohexahydro-pyrimidin-2-ylidene]carbamate Prepared as a mixture of atropisomers from Intermediate 113 and 1-(dichloro-methylene)pyrrolidinium chloride using General Method 7. LCMS (Method 3, ES+) 699.00 MH+, 2.60 minutes.

Intermediate 168 tert-Butyl (NE)-N-[(4S)-4-{2-fluoro-3-[6-fluoro-7-(trifluoromethyl)benzimidazol-1-yl]-phenyl}-1,4-dimethyl-6-oxohexahydropyrimidin-2-ylidene]carbamate To a solution of Intermediate 93 (0.45 g, 0.85 mmol) in MeOH (20 mL) were added copper(II) acetate (0.30 g, 1.70 mmol) and HCHO (0.06 mL, 1.70 mmol). The reaction mixture was heated at 80° C. for 3 h, then concentrated in vacuo. The residue was diluted with EtOAc (20 mL). The organic layer was washed with water (20 mL), dried over anhydrous Na$_2$SO$_4$ and concentrated in vacuo. The crude residue was purified by column chromatography (silica, 100-200 mesh, 30-50% EtOAc in hexanes) to afford the title compound (0.40 g, 88%) as a brown solid. LCMS (Method 3, ES+) 538.00 MH+, 3.46 minutes.

Example 1 (General Method 3)

1-{3-[(4S)-2-Imino-1,4-dimethyl-6-oxohexahydro-pyrimidin-4-yl]phenyl}-2-methyl-1H-benzimidazole-5-carbonitrile To a solution of Intermediate 14 (0.10 g, 0.21 mmol) in DCM (6 mL) was added TFA (0.2 mL) at 0° C. The reaction mixture was stirred at room temperature for 6 h, then concentrated in vacuo. The residue was washed with diethyl ether (100 mL), then lyophilised and dried in vacuo, to afford the TFA salt of the title compound (0.07 g, 95%) as a brown solid. $\delta_H$ (400 MHz, DMSO-$d_6$) 1.68 (s, 3H), 2.45 (s, 3H), 3.10 (s, 3H), 3.22 (d, J 16.7 Hz, 1H), 3.50 (d, J 16.2 Hz, 1H), 7.24 (d, J 8.1 Hz, 1H), 7.56-7.66 (m, 4H), 7.71 (d, J 7.6 Hz, 1H), 8.22 (br s, 1H), 10.45 (br s, 1H). LCMS (Method 1, ES+) 373 MH+, 0.64 minutes.

Example 2

1-{3-[(4)-2-Imino-1,4-dimethyl-6-oxohexahydropyrimidin-4-yl]phenyl}-N,N,2-trimethyl-1H-benzimidazole-4-carboxamide Prepared as the TFA salt from Intermediate 7 and Intermediate 23 according to General Methods 1a, 1b & 1c followed by General Method 3. LCMS (Method 1, ES+) 419 MH+, 0.59 minutes.

Example 3

1-{3-[(4)-2-Imino-1,4-dimethyl-6-oxohexahydropyrimidin-4-yl]phenyl}-2-methyl-1H-benzimidazole-4-carbonitrile Prepared as the TFA salt from 3-fluoro-2-nitrobenzonitrile and Intermediate 7 according to General Methods 1a, 1b & 1c followed by General Method 3. LCMS (Method 1, ES+) 373 MH+, 0.65 minutes.

Example 4

1-{3-[(4)-2-Imino-1,4-dimethyl-6-oxohexahydropyrimidin-4-yl]phenyl}-2-methyl-1H-benzimidazole-6-carboxylic Acid Prepared as the TFA salt from 3-fluoro-4-nitrobenzoic acid and Intermediate 7 according to General Methods 1a, 1b & 1c followed by General Method 3. LCMS (Method 1, ES+) 392 MH+, 0.43 minutes.

Example 5

1-{3-[(4)-2-Imino-1,4-dimethyl-6-oxohexahydropyrimidin-4-yl]phenyl}-N,N,2-trimethyl-1H-benzimidazole-7-carboxamide Prepared as the TFA salt from Intermediate 7 and Intermediate 24 according to General Methods 1a, 1b & 1c followed by General Method 3. LCMS (Method 1, ES+) 419 MH+, 0.55 minutes.

Example 6

1-{3-[(4S)-2-Imino-1,4-dimethyl-6-oxohexahydro-pyrimidin-4-yl]phenyl}-N,N,2-trimethyl-1H-benzimidazole-5-carboxamide Prepared as the TFA salt from Intermediate 7 and Intermediate 25 according to General Methods 1a, 1b & 1c followed by General Method 3. LCMS (Method 1, ES+) 419 MH+, 0.58 minutes.

Example 7

(6S)-2-Imino-3,6-dimethyl-6-{3-[2-methyl-6-(1-methyl-1H-pyrazol-4-yl)-1H-benzimidazol-1-yl]phenyl}tetrahydropyrimidin-4(1H)-one Example 8 (113 mg, 0.26 mmol), (XPhos) palladium(II) phenethylamine chloride (10.0 mg, 0.013 mmol), potassium tert-butoxide (45 mg, 0.39 mmol), 2-methyl-tetrahydrofuran (5 mL) and 1-methyl-4-(4,4,5,5-tetramethyl-1,3,2-dioxaborolan-2-yl)-1H-pyrazole (68 mg, 0.32 mmol) were placed in a round-bottomed flask and the reaction mixture was degassed. The reaction mixture was stirred under nitrogen, whilst heating at 65° C. overnight, then heated at 80° C. for a further 4 h. The reaction mixture was diluted with water (50 mL) and extracted with EtOAc (2×50 mL), then dried with $Na_2SO_4$. The solvent removed under vacuum. The resulting crude product was purified on Biotage Isolera 4 (SNAP C18, 12 g KP), eluting with a gradient of 0-50% acetonitrile (containing 0.1% formic acid) in aqueous acetic acid (10 mM), to afford the title compound (39 mg, 34%). $\delta_H$ (400 MHz, DMSO-$d_6$) 8.24 (s, 1H), 8.14 (s, 1H), 7.87 (d, J 0.8 Hz, 1H), 7.81 (d, J 1.5 Hz, 1H), 7.67-7.55 (m, 4H), 7.48-7.37 (m, 2H), 7.07 (d, J 8.4 Hz, 1H), 3.87 (s, 3H), 3.05 (d, J 16.0 Hz, 1H), 3.04 (s, 3H), 2.97-2.83 (m, 1H), 2.43 (s, 3H), 1.48 (s, 3H). LCMS (Method 1, ES+) 428 MH+, 1.45 minutes.

Example 8

(6S)-6-[3-(6-Bromo-2-methyl-1H-benzimidazol-1-yl)phenyl]-2-imino-3,6-dimethyl-tetrahydropyrimidin-4(1H)-one Prepared as the TFA salt from Intermediate 20 according to General Method 1c followed by General Method 3. LCMS (Method 1, ES+) 427 MH+, 1.24 minutes.

Example 9

(6S)-6-[3-(6-Chloro-2-ethyl-1H-benzimidazol-1-yl)phenyl]-2-imino-3,6-dimethyl-tetrahydropyrimidin-4(1H)-one Propionic acid (2 mL) was added to Intermediate 16 (150 mg, 0.3275 mmol). The reaction mixture was heated at 150° C. under microwave irradiation for 30 minutes. The solvent was removed by evaporation. The crude material was dissolved in EtOAc, then the solution was neutralised with 2M aqueous NaOH solution. The organic layer was dried with sodium sulfate, then the solvent was evaporated. The resulting oil was purified by preparative reverse phase HPLC to afford the title compound (3 mg, 2%) as a pale lyophilised solid. $\delta_H$ (300 MHz, DMSO-$d_6$) 8.30 (s, 1H), 7.73-7.51 (m, 4H), 7.42 (dt, J 7.3, 1.7 Hz, 1H), 7.25 (dd, J 8.6, 2.0 Hz, 1H), 7.03 (d, J 1.9 Hz, 1H), 2.86 (d, J 16.0 Hz, 1H), 2.72 (q, J 7.5

Hz, 2H), 1.47 (s, 3H), 1.21 (t, J 7.5 Hz, 3H). LCMS (Method 1, ES+) 396 MH+, 0.74 minutes.

Example 10

1-{3-[(4S)-2-Imino-1,4-dimethyl-6-oxohexahydropyrimidin-4-yl]phenyl}-2-methyl-1H-benzimidazole-7-carbonitrile Prepared as the TFA salt from 2-fluoro-3-nitrobenzonitrile and Intermediate 7 according to General Methods 1a, 1b & 1c followed by General Method 3. $\delta_H$ (400 MHz, DMSO-$d_6$) 1.65 (s, 3H), 2.35 (s, 3H), 3.05 (d, J 4.9 Hz, 3H), 3.20 (d, J 16.6 Hz, 1H), 3.55 (dd, J 16.6, 7.34 Hz, 1H), 7.39 (t, J 7.8 Hz, 1H), 7.58-7.72 (m, 5H), 8.02 (d, J 8.31 Hz, 1H), 10.41-10.52 (m, 1H). LCMS (Method 1, ES+) 373 MH+, 0.61 minutes.

Example 11

(6S)-2-Imino-3,6-dimethyl-6-{3-[2-methyl-4-(trifluoromethyl)-1H-benzimidazol-1-yl]-phenyl}tetrahydropyrimidin-4(1H)-one Prepared as the TFA salt from 1-fluoro-2-nitro-3-(trifluoromethyl)benzene and Intermediate 7 according to General Methods 1a, 1b & 1c followed by General Method 3. $\delta_H$ (400 MHz, DMSO-$d_6$) 1.68 (s, 3H), 2.47 (s, 3H), 3.10 (s, 3H), 3.23 (d, J 16.1 Hz, 1H), 3.50 (d, J 16.6 Hz, 1H), 7.32-7.40 (m, 2H), 7.61 (m, 3H), 7.65 (s, 1H), 7.69-7.77 (m, 1H), 10.47 (s, 1H). LCMS (Method 1, ES+) 416 MH+, 0.78 minutes.

Example 12

(6S)-2-Imino-3,6-dimethyl-6-{3-[2-methyl-6-(methylsulfonyl)-1H-benzimidazol-1-yl]-phenyl}tetrahydropyrimidin-4(1H)-one Prepared as the TFA salt from 2-fluoro-4-(methylsulfonyl)-1-nitrobenzene and Intermediate 7 according to General Methods 1a, 1b & 1c followed by General Method 3. LCMS (Method 1, ES+) 426 MH+, 0.60 minutes.

Example 13

(6S)-6-[3-(2,5-Dimethyl-3H-imidazo[4,5-b]pyridin-3-yl)phenyl]-2-imino-3,6-dimethyl-tetrahydropyrimidin-4(1H)-one Prepared as the TFA salt from 2-fluoro-6-methyl-3-nitropyridine and Intermediate 7 according to General Methods 1a, 1b & 1c followed by General Method 7. LCMS (Method 1, ES+) 363 MH+, 1.07 minutes.

Example 14

(6S)-2-Imino-3,6-dimethyl-6-{3-[2-methyl-5-(trifluoromethyl)-1H-benzimidazol-1-yl]-phenyl}tetrahydropyrimidin-4(1H)-one Prepared as the TFA salt from 1-fluoro-2-nitro-4-(trifluoromethyl)benzene and Intermediate 7 according to General Methods 1a, 1b & 1c followed by General Method 3. $\delta_H$ (400 MHz, DMSO-$d_6$) 1.68 (s, 3H), 3.10 (s, 3H), 3.23 (d, J 16.1 Hz, 1H), 3.51 (d, J 16.1 Hz, 1H), 7.29 (d, J 8.3 Hz, 1H), 7.55 (d, J 8.3 Hz, 1H), 7.59-7.67 (m, 3H), 7.69-7.77 (m, 1H), 8.03 (s, 1H), 10.70 (br s, 1H) (3H submerged in solvent peak). LCMS (Method 1, ES+) 416 MH+, 1.30 minutes.

Example 15

(6S)-2-Imino-3,6-dimethyl-6-{3-[2-methyl-7-(trifluoromethyl)-1H-benzimidazol-1-yl]-phenyl}tetrahydropyrimidin-4(1H)-one Prepared as the TFA salt from 2-fluoro-1-nitro-3-(trifluoromethyl)benzene and Intermediate 7 according to General Methods 1a, 1b & 1c followed by General Method 3. $\delta_H$ (400 MHz, DMSO-$d_6$) 1.63 (s, 3H), 2.22 (s, 3H), 3.03 (s, 3H), 3.20 (d, J 16.1 Hz, 1H), 3.44-3.54 (m, 1H), 7.41 (t, J 7.8 Hz, 1H), 7.49 (d, J 6.8 Hz, 1H), 7.53 (d, J 6.8 Hz, 1H), 7.58 (d, J 7.3 Hz, 1H), 7.61-7.66 (m, 2H), 7.99 (d, J 7.8 Hz, 1H), 10.53-10.64 (m, 1H). LCMS (Method 1, ES+) 416 MH+, 1.34 minutes.

Example 16

(6S)-6-[3-(6-Chloro-2-methyl-1H-imidazo[4,5-b]pyridin-1-yl)phenyl]-2-imino-3,6-dimethyltetrahydropyrimidin-4(1H)-one Prepared as the TFA salt from Intermediate 18 according to General Method 1c followed by General Method 3. LCMS (Method 1, ES+) 384 MH+, 0.65 minutes.

Example 17

(6S)-6-{3-[6-Chloro-2-(hydroxymethyl)-1H-benzimidazol-1-yl]phenyl}-2-imino-3,6-dimethyltetrahydropyrimidin-4(1H)-one Glycolic acid (199 mg, 2.62 mmol) was added to Intermediate 16 (150 mg, 0.33 mmol). The reaction mixture was heated at 150° C. under microwave irradiation for 30 minutes. The solvent was removed by evaporation. The crude residue was dissolved in EtOAc, then the solution was neutralised with 2M aqueous NaOH solution. The organic layer was separated and dried with $Na_2SO_4$, then the solvent was evaporated. The resulting oil was purified by preparative reverse phase HPLC to afford the title compound (22 mg, 17%) as a pale lyophilised solid. $\delta_H$ (300 MHz, DMSO-$d_6$) 7.73 (d, J 8.6 Hz, 1H), 7.63 (s, 1H), 7.55-7.44 (m, 2H), 7.30 (dd, J 8.6, 2.0 Hz, 1H), 7.12 (s, 1H), 4.55 (s, 3H), 3.12 (d, J 16.0 Hz, 1H), 2.93 (d, J 16.0 Hz, 1H), 1.50 (s, 3H).

Example 18

(6S)-6-[3-(6-Chloro-1H-benzimidazol-1-yl)phenyl]-2-imino-3,6-dimethyltetrahydro-pyrimidin-4(1H)-one Formic acid (1.8 mL, 41 mmol) was added to Intermediate 16 (100 mg, 0.22 mmol). The reaction mixture was heated at 180° C. under microwave irradiation for 30 minutes. The solvent was removed by evaporation. The crude residue was dissolved in EtOAc, then the solution was neutralised with saturated aqueous $Na_2CO_3$ solution. The organic layer was separated and dried with $Na_2SO_4$, then the solvent was evaporated. The resulting oil was purified by preparative reverse phase HPLC to afford the title compound (32 mg, 39%) as a white lyophilised solid. LCMS (Method 1, ES+) 368 MH+, 0.70 minutes.

Example 19

1-{3-[(4S)-2-Imino-1,4-dimethyl-6-oxohexahydropyrimidin-4-yl]phenyl}-N,N,2-trimethyl-1H-benzimidazole-6-sulfonamide Prepared as the TFA salt from 3-fluoro-N,N-dimethyl-4-nitrobenzene-1-sulfonamide and Intermediate 7 according to General Methods 1a, 1b & 1c followed by General Method 3. LCMS (Method 1, ES+) 455 MH+, 0.66 minutes.

Example 20

(6S)-2-Imino-6-[3-(6-methoxy-2-methyl-1H-benzimidazol-1-yl)phenyl]-3,6-dimethyl-tetrahydropyrimidin-4(1H)-one Prepared as the TFA salt from 2-fluoro-4-methoxy-1-nitrobenzene and Intermediate 7 according to General Methods 1a, 1b & 1c followed by General Method 3. LCMS (Method 1, ES+) 378 MH+, 1.19 minutes.

Example 21 (General Method 4)

(6S)-6-[3-(2,5-Dimethylpyrazolo[1,5-a]pyridin-3-yl)phenyl]-2-imino-3,6-dimethyl-tetrahydropyrimidin-4(1H)-one To a solution of Intermediate 11 (0.20 g, 0.50 mmol) and tetrahydroxy diboron (0.14 g, 1.50 mmol) in EtOH (5 mL) were added XPhos Pd G2 (0.003 g, 0.001 mmol), XPhos (0.004 g, 0.01 mmol) and potassium acetate (0.14 g, 1.50 mmol). The reaction mixture was heated under microwave irradiation at 80° C. for 3 h, then Intermediate 21 (0.11 g, 0.50 mmol) and $K_2CO_3$ (0.21 g, 1.5 mmol) in $H_2O$ (0.7 mL) were added. The reaction mixture was heated at 80° C. for 12 h, then concentrated in vacuo. The residue was dissolved in EtOAc (100 mL), then washed with $H_2O$ (100 mL) and brine (100 mL). The organic layer was separated and dried over anhydrous $Na_2SO_4$, then concentrated in vacuo. The crude residue was purified by column chromatography (silica 100-200 mesh, 45% EtOAc in hexanes). To the resulting white solid (0.08 g) in 1,4-dioxane (2 mL) was added 4M HCl in 1,4-dioxane (1 mL). The reaction mixture was stirred at room temperature for 16 h, then concentrated in vacuo. The crude residue was purified by washing with diethyl ether (80 mL) to afford the hydrochloride salt of the title compound (0.06 g, 97%) as an off-white solid. $\delta_H$ (400 MHz, DMSO-$d_6$) 1.65 (s, 3H), 2.36 (s, 3H), 2.44 (s, 3H), 3.09 (s, 3H), 3.22 (d, J 16.4 Hz, 1H), 6.72 (d, J 6.9 Hz, 1H), 7.35-7.40 (m, 2H), 7.53-7.41 (m, 4H), 8.70 (br s, 1H), 10.58 (s, 1H). LCMS (Method 1, ES+) 378 MH+, 1.28 minutes.

Example 22

(6S)-6-[3-(6-Chloro-2-methylimidazo[1,2-a]pyridin-3-yl)phenyl]-2-imino-3,6-dimethyl-tetrahydropyrimidin-4(1H)-one Prepared as the HCl salt from Intermediate 11 and Intermediate 22 according to General Method 4. LCMS (Method 1, ES+) 381 MH+, 1.22 minutes.

Example 23

(6S)-2-Imino-3,6-dimethyl-6-{3-[2-methyl-6-(1-methyl-1H-pyrazol-4-yl)imidazo[1,2-a]-pyridin-3-yl]phenyl}tetrahydropyrimidin-4(1H)-one Prepared from 1-methyl-4-(4,4,5,5-tetramethyl-1,3,2-dioxaborolan-2-yl)pyrazole and Example 22 by analogy with the Suzuki procedure described in Example 21. LCMS (Method 1, ES+) 428 MH+, 0.56 minutes.

Example 24

6-Chloro-1-{3-[(4S)-2-imino-1,4-dimethyl-6-oxohexahydropyrimidin-4-yl]phenyl}-2-methyl-1H-indole-3-carbonitrile 2-(4-Chlorophenyl)-3-oxobutanenitrile (210 mg, 1.083 mmol), Intermediate 7 (300 mg, 0.903 mmol) and molecular sieves (200 mg) were suspended in acetic acid (2.5 mL) in a microwave vial. The reaction was heated at 120° C. under microwave irradiation for 20 minutes, then the solvent was removed by evaporation. The resulting oil was dissolved in DCM. The solution was cooled to 0° C., then [bis(trifluoroacetoxy)iodo]-benzene (232 mg, 0.540 mmol) was added. The reaction mixture was stirred at 0° C. for 15 minutes, then at room temperature for 20 minutes. The reaction mixture was adsorbed onto silica (3 g) and passed through 10 g silica, eluting with 100% DCM (100 mL), then 5% MeOH/DCM (200 mL). The resulting off-white solid was purified by preparative HPLC (0.2% TFA buffer) to give the TFA salt of the title compound (48.5 mg, 13%) as a pale yellow solid. $\delta_H$ (400 MHz, CDCl$_3$) 1.75 (s, 3H), 2.42 (s, 3H), 3.07 (d, J 16.5 Hz, 1H), 3.31 (s, 3H), 3.41 (d, J 16.5 Hz, 1H), 6.99 (s, 1H), 7.33-7.43 (m, 2H), 7.49-7.71 (m, 4H), 10.21 (br s, 1H), 11.58 (br s, 1H). LCMS (Method 1, ES+) 406 MH+, 0.82 minutes.

Example 25

(6S)-6-[3-(5,6-Dichloro-2-methyl-1H-benzimidazol-1-yl)phenyl]-2-imino-3,6-dimethyl-tetrahydropyrimidin-4(1H)-one Prepared as the TFA salt from 1,2-dichloro-4-fluoro-5-nitrobenzene and Intermediate 7 according to General Methods 1a, 1b & 1c followed by General Method 3. LCMS (Method 2, ES+) 417 MH+, 5.19 minutes.

Example 26

(6S)-6-[3-(7-Chloro-2-methyl-1H-benzimidazol-1-yl)phenyl]-2-imino-3,6-dimethyl-tetrahydropyrimidin-4(1H)-one Prepared as the TFA salt from 1-chloro-2-fluoro-3-nitrobenzene and Intermediate 7 according to General Methods 1a, 1b & 1c followed by General Method 3. LCMS (Method 2, ES+) 382 MH+, 4.52 minutes.

Example 27

(6S)-6-[3-(4-Chloro-2-methyl-1H-benzimidazol-1-yl)phenyl]-2-imino-3,6-dimethyl-tetrahydropyrimidin-4(1H)-one Prepared as the TFA salt from 1-chloro-3-fluoro-2-nitrobenzene and Intermediate 7 according to General Methods 1a, 1b & 1c followed by General Method 3. LCMS (Method 2, ES+) 382 MH+, 4.56 minutes.

Example 28

(6S)-6-[3-(6-Chloro-2-methyl-1H-benzimidazol-1-yl)phenyl]-2-imino-3,6-dimethyl-tetrahydropyrimidin-4(1H)-one Prepared as the TFA salt from 4-chloro-2-fluoro-1-nitrobenzene and Intermediate 7 according to General Methods 1a, 1b & 1c followed by General Method 3. $\delta_H$ (400 MHz, CDCl$_3$) 1.69 (s, 3H), 2.64 (s, 3H), 3.12 (s, 3H), 3.27 (d, J 16.3 Hz, 1H), 3.48 (d, J 16.3 Hz, 1H), 7.41-7.36 (m, 1H), 7.56 (dd, J 8.6, 1.5 Hz, 1H), 7.72-7.65 (m, 1H), 7.91-7.72 (m, 4H), 8.98 (s, 1H), 11.06 (s, 1H). LCMS (Method 1, ES+) 382 MH+, 1.26 minutes.

Example 29

1-{3-[(4S)-2-Imino-1,4-dimethyl-6-oxohexahydropyrimidin-4-yl]phenyl}-2-methyl-1H-benzimidazole-6-carbonitrile Prepared as the TFA salt from 3-fluoro-4-nitrobenzonitrile and Intermediate 7 according to General Methods 1a, 1b & 1c followed by General Method 3. LCMS (Method 1, ES+) 373 MH+, 1.15 minutes.

Example 30

(6S)-2-Imino-3,6-dimethyl-6-[3-(2-methyl-1H-benzimidazol-1-yl)phenyl]tetrahydro-pyrimidin-4(1H)-one Prepared as the TFA salt from 1-fluoro-2-nitrobenzene and Intermediate 7 according to General Methods 1a, 1b & 1c followed by General Method 3. $\delta_H$ (400 MHz, DMSO-d$_6$) 1.69 (s, 3H), 2.53 (s, 3H), 3.10 (s, 3H), 3.24 (d, J 16.63 Hz, 1H), 3.48 (d, J 16.14 Hz, 1H), 7.22 (d, J 7.83 Hz, 1H), 7.33-7.39 (m, 1H), 7.40-7.46 (m, 1H), 7.60-7.66 (m, 1H), 7.68 (br s, 2H), 7.76 (m, 2H), 10.66 (s, 1H). LCMS (Method 1, ES+) 348 MH+, 0.67 minutes.

Example 31

(6S)-6-[3-(5-Chloro-1H-indazol-1-yl)phenyl]-2-imino-3,6-dimethyltetrahydropyrimidin-4(1H)-one Intermediate 11 (20 mg, 0.045 mmol), 5-chloro-1H-indazole (8 mg, 0.054 mmol) and copper(II) acetate (15 mg, 0.081 mmol) were suspended in DMF (0.25 mL). Pyridine (1 mL) was added and the reaction mixture was heated at 120° C. under microwave irradiation for 30 minutes. The solvent was removed under reduced pressure and the residue was purified using preparative HPLC to afford the title compound. LCMS (Method 2, ES+) 368 MH+, 5.33 minutes.

Example 32

(6S)-6-[3-(5-Chloro-2-methyl-1H-benzimidazol-1-yl)phenyl]-2-imino-3,6-dimethyl-tetrahydropyrimidin-4(1H)-one Prepared as the TFA salt from 4-chloro-1-fluoro-2-nitrobenzene and Intermediate 7 according to General Methods 1a, 1b & 1c followed by General Method 3. LCMS (Method 2, ES+) 382 MH+, 4.74 minutes.

Example 33

(6S)-6-[3-(1,3-Benzothiazol-2-yl)phenyl]-2-imino-3,6-dimethyltetrahydropyrimidin-4(1H)-one Prepared as the HCl salt from 2-bromobenzothiazole and Intermediate 11 according to General Method 4. LCMS (Method 2, ES+) 351 MH+, 5.42 minutes.

Example 34

(6S)-6-[3-(Imidazo[1,2-a]pyridin-3-yl)phenyl]-2-imino-3,6-dimethyltetrahydropyrimidin-4(1H)-one Prepared as the HCl salt from 3-bromoimidazo[1,2-a]pyridine and Intermediate 11 according to General Method 4. LCMS (Method 2, ES+) 333 MH+, 3.19 minutes.

Example 35

(6S)-2-Imino-3,6-dimethyl-6-[3-(quinolin-3-yl)phenyl]tetrahydropyrimidin-4(1H)-one Prepared as the HCl salt from 3-bromoquinoline and Intermediate 11 according to General Method 4. LCMS (Method 2, ES+) 345 MH+, 3.64 minutes.

Example 36

(6S)-6-{3-[5-(Hydroxymethyl)-2-methylbenzimidazol-1-yl]phenyl}-2-imino-3,6-dimethylhexahydropyrimidin-4-one Prepared as the TFA salt from Intermediate 50 using General Method 3. $\delta_H$ (400 MHz, DMSO-d$_6$) 1.69 (s, 3H), 3.10 (s, 3H), 3.20-3.31 (m, 1H), 3.48 (m, 1H), 4.64 (s, 2H), 7.15 (d, J 8.11 Hz, 1H), 7.31 (d, J 8.11 Hz, 1H), 7.56-7.82 (m, 5H), 8.72 (br s, 2H), 10.41-10.55 (m, 1H) (3H merged into solvent peak). LCMS (Method 3, ES+) 378.00 MH+ 1.51 minutes.

Example 37

(6S)-6-{3-[5-(1-Hydroxyethyl)-2-methylbenzimidazol-1-yl]phenyl}-2-imino-3,6-dimethylhexahydropyrimidin-4-one Prepared as the TFA salt from Intermediate 55 using General Method 3. $\delta_H$ (400 MHz, DMSO-d$_6$) 1.37 (d, J 5.79 Hz, 3H), 1.69 (s, 3H), 3.10 (s, 3H), 3.24 (d, J 16.42 Hz, 1H), 3.49 (d, J 16.42 Hz, 1H), 4.88 (d, J 6.28 Hz, 1H), 7.13 (d, J 8.21 Hz, 1H), 7.34 (d, J 8.21 Hz, 1H), 7.50-7.80 (m, 5H), 10.48 (br s, 1H) (5H merged into solvent peak). LCMS (Method 3, ES+) 392.00 MH+, 1.62 minutes.

Example 38

(6S)-6-{3-[5-(1-Hydroxy-1-methylethyl)-2-methylbenzimidazol-1-yl]phenyl}-2-imino-3,6-dimethylhexahydropyrimidin-4-one Prepared as the TFA salt from Intermediate 59 using General Method 3. $\delta_H$ (400 MHz, DMSO-d$_6$) 1.44 (s, 6H), 2.39 (s, 3H), 2.60-2.67 (m, 1H), 2.80 (d, J 15.65 Hz, 1H), 3.00 (s, 3H), 5.00 (s, 1H), 6.99 (d, J 8.80 Hz, 1H), 7.30 (d, J 8.80 Hz, 1H), 7.37 (d, J 7.83 Hz, 1H), 7.52-7.62 (m, 4H), 7.68 (br s, 1H), 8.21 (br s, 1H) (3H merged into solvent peak). LCMS (ESI) 406.00 MH$^+$, 1.64 minutes.

Example 39

(6S)-6-[3-(5-Hydroxy-2-methylbenzimidazol-1-yl)phenyl]-2-imino-3,6-dimethyl-hexahydropyrimidin-4-one Prepared as the TFA salt from Intermediate 62 using General Method 3. $\delta_H$ (400 MHz, DMSO-d$_6$) 1.68 (s, 3H), 3.10 (s, 3H), 3.23 (d, J 16.14 Hz, 1H), 6.84 (d, J 7.83 Hz, 1H), 7.00-7.13 (m, 2H), 7.52-7.82 (m, 5H), 9.64 (s, 1H), 10.30-10.49 (m, 1H) (4H merged into solvent peak). LCMS (Method 3, ES+) 364.00 MH$^+$, 1.53 minutes.

Example 40

(6S)-6-{3-[6-Chloro-2-methyl-7-(trifluoromethyl)benzimidazol-1-yl]phenyl}-2-imino-3,6-dimethyl-hexahydropyrimidin-4-one Prepared as the TFA salt from Intermediate 66 using General Method 3. $\delta_H$ (400 MHz, DMSO-d$_6$) 1.63 (s, 3H), 2.21 (s, 3H), 3.05 (d, J 6.36 Hz, 3H), 3.19 (dd, J 16.63, 3.91 Hz, 1H), 3.47 (dd, J 16.63, 5.38 Hz, 1H), 7.41-7.68 (m, 5H), 7.95 (d, J 8.31 Hz, 1H), 10.37 (d, J 16.63 Hz, 1H) (NH signal absent). LCMS (Method 3, ES+) 450.00 MH$^+$, 2.34 minutes.

Example 41

(6S)-2-Imino-3,6-dimethyl-6-{3-[2-methyl-6-(trifluoromethyl)benzimidazol-1-yl]-phenyl}hexahydropyrimidin-4-one Prepared as the TFA salt from Intermediate 69 using General Method 3. $\delta_H$ (400 MHz, CD$_3$OD) 1.79 (s, 3H), 2.59 (s, 3H), 3.21 (s, 3H), 3.55 (d, J 16.63 Hz, 1H), 7.43 (br s, 1H), 7.60 (d, J 6.36 Hz, 1H), 7.64-7.81 (m, 5H), 7.89 (d, J 7.83 Hz, 1H) (NH signals absent). LCMS (Method 3, ES+) 416.00 MH$^+$, 2.26 minutes.

Example 42

1-{3-[(4S)-2-Imino-1,4-dimethyl-6-oxohexahydropyrimidin-4-yl]phenyl}-2-methyl-benzimidazole-5-carboxylic Acid Prepared as the TFA salt from Intermediate 72 using General Method 3. LCMS (Method 3, ES+) 392.00 MH$^+$, 1.24 minutes.

Example 43

(6)-6-{3-[7-(Dimethylaminomethyl)-2-methylbenzimidazol-1-yl]phenyl}-2-imino-3,6-dimethylhexahydropyrimidin-4-one Prepared as the TFA salt from Intermediate 78 using General Method 3. LCMS (Method 3, ES+) 405.00 MH$^+$, 2.26 minutes.

Example 44

(6S)-6-[3-(6-Chloro-2-methylbenzimidazol-1-yl)-2-fluorophenyl]-2-imino-3,6-dimethyl-tetrahydropyrimidin-4(1H)-one Prepared as the TFA salt of a mixture of atropisomers from Intermediate 81 using General Method 3. LCMS (Method 3, ES+) 400.00 MH$^+$, 2.15 minutes.

Example 45

(6S)-6-[3-(6-Chloro-2-methylbenzimidazol-1-yl)-2,4-difluorophenyl]-2-imino-3,6-dimethyltetrahydropyrimidin-4(1H)-one Prepared as the TFA salt of a mixture of atropisomers from Intermediate 91 using General Method 3. LCMS (Method 3, ES+) 418.00 MH$^+$, 2.49 minutes.

Example 46

6-Chloro-1-{2-fluoro-3-[(4S)-2-imino-1,4-dimethyl-6-oxohexahydropyrimidin-4-yl]-phenyl}-2-methyl-indole-3-carbonitrile To a solution of Intermediate 33 (0.15 g, 0.42 mmol) in acetic acid (2.5 mL) were added 2-(4-chlorophenyl)-3-oxobutanenitrile (0.10 g, 0.51 mmol) and molecular sieves (0.15 g). The reaction mixture was heated under microwave irradiation at 130° C. for 30 minutes. The reaction mixture was cooled to 0° C., followed by the addition of DCM (6 mL) and PIFA (0.11 g, 0.25 mmol). The reaction mixture was stirred at room temperature for 6 h, then concentrated in vacuo. The crude residue was purified by preparative HPLC to afford the title compound (0.014 g, 8%, mixture of atropisomers) as an off-white solid. LCMS (Method 3, ES+) 424.00 MH$^+$, 3.07 minutes.

Example 47

(6S)-6-[3-(6-Chloro-5-methoxy-2-methylbenzimidazol-1-yl)-2-fluorophenyl]-2-imino-3,6-dimethyl-hexahydropyrimidin-4-one Prepared as the TFA salt of a mixture of atropisomers from Intermediate 84 using General Method 3. LCMS (Method 3, ES+) 430.00 MH$^+$, 2.12 minutes.

Example 48

(6S)-6-[3-(6-Chloro-5-hydroxy-2-methylbenzimidazol-1-yl)-2-fluorophenyl]-2-imino-3,6-dimethyl-hexahydropyrimidin-4-one To a solution of Intermediate 84 (0.03 g, 0.06 mmol) in DCM (5 mL) was added boron tribromide (0.05 mL) at 0° C. The reaction mixture was stirred at room temperature for 16 h, then concentrated in vacuo. The residue was washed with diethyl ether (10 mL) and DCM (10 mL). The residue was diluted with H$_2$O (20 mL) and saturated aqueous NaHCO$_3$ solution (25 mL), then extracted with EtOAc (2×25 mL). The organic layer was separated, washed with H$_2$O (25 mL) and brine (25 mL), then dried over anhydrous Na$_2$SO$_4$ and concentrated in vacuo, to afford the title compound (0.02 g, 87%, mixture of atropisomers) as an off-white solid. LCMS (Method 3, ES+) 416.00 MH$^+$, 1.75 minutes.

Example 49

(6S)-6-{3-[6-Chloro-2-methyl-7-(trifluoromethyl)benzimidazol-1-yl]-2-fluorophenyl}-2-imino-3,6-dimethylhexahydropyrimidin-4-one Prepared, as the free base of a mixture of atropisomers after purification by preparative HPLC, from Intermediate 87 using General Method 3. LCMS (Method 3, ES+) 468.00 MH$^+$, 2.16 minutes.

Example 50

(6S)-6-{3-[6-Chloro-2-(dimethylamino)benzimidazol-1-yl]-2-fluorophenyl}-2-imino-3,6-dimethylhexahydropyrimidin-4-one Prepared as the TFA salt of a mixture of atropisomers from Intermediate 88 using General Method 3. LCMS (Method 3, ES+) 429.00 MH$^+$, 1.57 minutes.

Example 51

(6S)-6-{2-Fluoro-3-[6-fluoro-2-methyl-7-(trifluoromethyl)benzimidazol-1-yl]phenyl}-2-imino-3,6-dimethylhexahydropyrimidin-4-one Prepared, as the TFA salt of a mixture of atropisomers in a 1:1 ratio, from Intermediate 94 using General Method 3. The atropisomers were separated using the following method:
HPLC Conditions
Column: DIOL, 250 mm×4.6 mm, 5μ
Mobile Phase A: 0.1% DEA in MTBE
Mobile Phase B: 0.1% DEA in MTOH:IPA (80:20)
Isocratic: 10% B
Flow rate: 1.0 mL/minute
UV: 290 nm
Retention time of atropisomer A: 6.13 minutes; HPLC Purity: 95.8%.
Retention time of atropisomer B: 5.90 minutes; HPLC Purity: 95.8%.
Atropisomer A: δ$_H$ (400 MHz, DMSO-d$_6$) 1.44 (s, 3H), 2.19 (s, 3H), 2.79-2.85 (m, 1H), 2.87-2.94 (m, 1H), 3.01 (s, 3H), 7.32-7.45 (m, 3H), 7.58 (t, J 7.09 Hz, 1H), 7.70-7.78 (m, 1H), 8.01 (dd, J 8.80, 4.40 Hz, 1H) (NH signal absent). LCMS (Method 3, ES+) 452.00 MH$^+$, 1.99 minutes.
Atropoisomer B: δ$_H$ (400 MHz, DMSO-d$_6$) 1.48 (s, 3H), 2.20 (s, 3H), 2.84-2.92 (m, 2H), 3.03 (s, 3H), 7.32-7.42 (m, 3H), 7.59 (t, J 7.09 Hz, 1H), 7.70-7.74 (m, 1H), 7.96-8.02 (m, 1H) (NH signal absent). LCMS (Method 3, ES+) 452.00 MH$^+$, 2.03 minutes.

Example 52

(6S)-6-{2-Fluoro-3-[6-fluoro-7-(trifluoromethyl)benzimidazol-1-yl]phenyl}-2-imino-3,6-dimethylhexahydropyrimidin-4-one A stirred solution of Intermediate 93 (0.10 g, 0.18 mmol) and 2-hydroxy-2-methylpropanoic acid (0.19 g, 1.89 mmol) in 4M HCl (5 mL) was heated in a sealed tube at 110° C. for 3 h. The reaction mixture was diluted with EtOAc (20 mL) and washed with saturated aqueous NaHCO$_3$ solution (2×5 mL). The organic layer was separated, dried over anhydrous Na$_2$SO$_4$ and concentrated in vacuo. The crude residue was purified by preparative HPLC to afford the title compound (0.032 g, 40%, mixture of atropisomers) as a brown solid. LCMS (Method 3, ES+) 438.00 MH$^+$, 2.28 minutes.

Example 53

(6S)-6-{3-[2-(Dimethylamino)-6-fluoro-7-(trifluoromethyl)benzimidazol-1-yl]-2-fluorophenyl}-2-imino-3,6-dimethylhexahydropyrimidin-4-one Prepared as the TFA salt of a mixture of atropisomers from Intermediate 95 using General Method 3. LCMS (Method 3, ES+) 481.00 MH$^+$, 2.06 minutes.

Example 54

(6S)-6-{2-Fluoro-3-[6-fluoro-2-methyl-7-(trifluoromethyl)benzimidazol-1-yl]phenyl}-2-imino-6-methylhexahydropyrimidin-4-one Prepared, as the free base of a mixture of atropisomers after purification by preparative HPLC, from Intermediate 98 using General Method 3. LCMS (Method 3, ES+) 438.00 MH$^+$, 1.99 minutes.

Example 55

5-Fluoro-3-{2-fluoro-3-[(4S)-2-imino-1,4-dimethyl-6-oxohexahydropyrimidin-4-yl]-phenyl}-4-(trifluoromethyl)-1H-benzimidazol-2-one Prepared as the TFA salt of a mixture of atropisomers from Intermediate 99 using General Method 3. Atropisomer A: LCMS (Method 3, ES+) 454.00 MH$^+$, 1.94 minutes. Atropoisomer B: LCMS (Method 3, ES+) 454.00 MH$^+$, 2.00 minutes.

Example 56

(6S)-6-[3-(6-Chloro-2-methylbenzimidazol-1-yl)-2-fluorophenyl]-3-ethyl-2-imino-6-methylhexahydropyrimidin-4-one Prepared, as the free base of a mixture of atropisomers after purification by preparative HPLC, from Intermediate 121 using General Method 3. LCMS (Method 3, ES+) 414.00 MH$^+$, 2.28 minutes.

Example 57

(6)-6-{2-Fluoro-3-[6-fluoro-2-methyl-7-(trifluoromethyl)benzimidazol-1-yl]phenyl}-3-(2-hydroxyethyl)-2-imino-6-methylhexahydropyrimidin-4-one Prepared as the free base of a mixture of atropisomers after purification by preparative HPLC, from Intermediate 111 using General Method 3. LCMS (Method 3, ES+) 482.00 MH$^+$, 1.99 minutes.

Example 58

(6S)-6-{2-Fluoro-3-[6-fluoro-2-methoxy-7-(trifluoromethyl)benzimidazol-1-yl]phenyl}-2-imino-3,6-dimethylhexahydropyrimidin-4-one

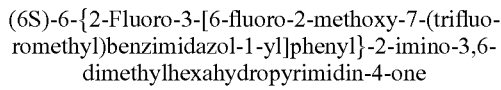

Prepared as the TFA salt of a mixture of atropisomers from Intermediate 118 using General Method 3. LCMS (Method 3, ES+) 468.00 MH$^+$, 2.44 and 2.47 minutes.

Example 59

(6S)-6-{3-[7-(Difluoromethoxy)-6-fluoro-2-methylbenzimidazol-1-yl]-2-fluorophenyl}-2-imino-3,6-dimethylhexahydropyrimidin-4-one

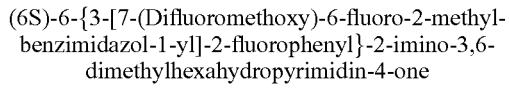

Prepared, as the free base of a mixture of atropisomers after purification by preparative HPLC, from Intermediate 126 using General Method 3. LCMS (Method 3, ES+) 450.00 MH$^+$, 1.84 and 1.88 minutes.

Example 60

(6S)-6-{3-[7-(Difluoromethyl)-6-fluoro-2-methylbenzimidazol-1-yl]-2-fluorophenyl}-2-imino-3,6-dimethylhexahydropyrimidin-4-one

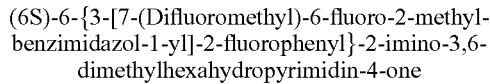

Prepared as the TFA salt of a mixture of atropisomers from Intermediate 130 using General Method 3. LCMS (Method 3, ES+) 434.00 MH$^+$, 1.83 and 1.87 minutes.

Example 61

(6)-6-{2-Fluoro-3-[6-fluoro-2-(1-hydroxy-1-methylethyl)-7-(trifluoromethyl)-benzimidazol-1-yl]phenyl}-2-imino-3,6-dimethylhexahydropyrimidin-4-one

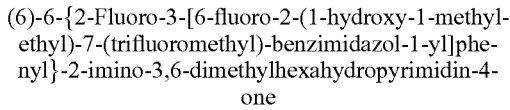

Prepared, as the free base of a mixture of atropisomers after purification by preparative HPLC, from Intermediate 131 using General Method 3. LCMS (Method 3, ES+) 496.00 MH$^+$, 1.99 and 2.04 minutes.

Example 62

(6S)-6-{3-[6-Chloro-2-(methylamino)benzimidazol-1-yl]-2-fluorophenyl}-2-imino-3,6-dimethylhexahydropyrimidin-4-one

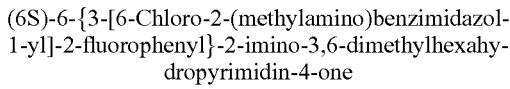

Prepared, as the free base of a mixture of atropisomers after purification by preparative HPLC, from Intermediate 132 using General Method 3. LCMS (Method 3, ES+) 415.00 MH$^+$, 1.56 and 1.63 minutes.

Example 63

6-Chloro-2-(dimethylamino)-1-{2-fluoro-3-[(4S)-2-imino-1,4-dimethyl-6-oxohexahydro-pyrimidin-4-yl]phenyl}benzimidazole-5-carbonitrile

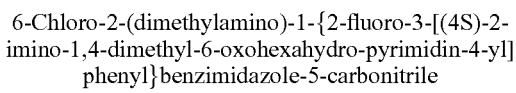

Prepared as the TFA salt of a mixture of atropisomers from Intermediate 136 using General Method 3. LCMS (Method 3, ES+) 454.00 MH$^+$, 1.86 and 1.90 minutes.

Example 64

(6S)-6-{2-Fluoro-3-[6-fluoro-2-(methylamino)-7-(trifluoromethyl)benzimidazol-1-yl]-phenyl}-2-imino-3,6-dimethylhexahydropyrimidin-4-one

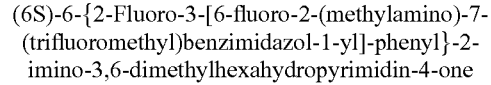

Prepared as the TFA salt of a mixture of atropisomers from Intermediate 143 using General Method 3. LCMS (Method 3, ES+) 467.00 MH$^+$, 2.28 and 2.32 minutes.

Example 65

6-Chloro-2-(dimethylamino)-1-{2-fluoro-3-[(4S)-2-imino-1,4-dimethyl-6-oxohexahydro-pyrimidin-4-yl]phenyl}benzimidazole-4-carbonitrile

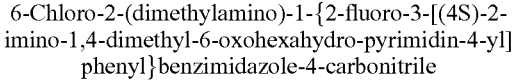

Prepared as the TFA salt of a mixture of atropisomers from Intermediate 141 using General Method 3. LCMS (Method 3, ES+) 454.00 MH$^+$, 2.45 minutes.

Example 66

2-(Dimethylamino)-1-{2-fluoro-3-[(4S)-2-imino-1,4-dimethyl-6-oxohexahydropyrimidin-4-yl]phenyl}benzimidazole-4-carbonitrile

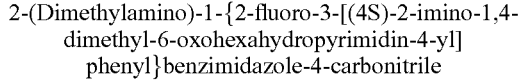

Prepared as the TFA salt of a mixture of atropisomers from Intermediate 142 using General Method 3. LCMS (Method 3, ES+) 420.00 MH$^+$, 1.96 minutes.

Example 67

(6S)-6-{3-[6-Chloro-2-(pyrrolidin-1-yl)benzimidazol-1-yl]-2-fluorophenyl}-2-imino-3,6-dimethylhexahydropyrimidin-4-one

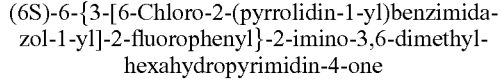

To a solution of Intermediate 145 (0.30 g, 0.71 mmol) in propan-2-ol (5 mL) was added pyrrolidine (0.26 g, 3.57 mmol). The reaction mixture was heated at 100° C. for 16 h, then quenched with brine (20 mL) and extracted with EtOAc (2×20 mL). The organic layer was separated, dried over anhydrous Na$_2$SO$_4$ and concentrated in vacuo. The crude residue was purified by column chromatography (silica, 100-200 mesh, 20% MeOH in DCM) and preparative HPLC to afford the title compound (TFA salt, 0.034 g, 10%, mixture of atropisomers) as an off-white solid. LCMS (Method 3, ES+) 455.00 MH$^+$, 2.35 minutes.

Example 68

5-Chloro-3-{2,6-difluoro-3-[(4S)-2-imino-1,4-dimethyl-6-oxohexahydropyrimidin-4-yl]phenyl}-1H-benzimidazol-2-one

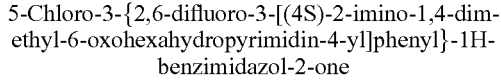

Prepared as the TFA salt of a mixture of atropisomers from Intermediate 146 using General Method 3. LCMS (Method 3, ES+) 420.00 MH$^+$, 2.00 minutes.

Example 69

(6S)-6-{3-[6-Chloro-2-(dimethylamino)benzimidazol-1-yl]-2,4-difluorophenyl}-2-imino-3,6-dimethylhexahydropyrimidin-4-one

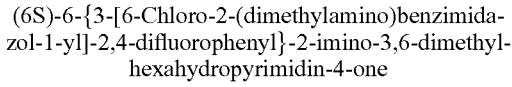

Prepared as the TFA salt of a mixture of atropisomers from Intermediate 147 using General Method 3. LCMS (Method 3, ES+) 447.00 MH$^+$, 2.35 minutes.

Example 70

(6S)-6-{3-[6-Chloro-2-(dimethylamino)benzimidazol-1-yl]-2-fluorophenyl}-3-(2-hydroxyethyl)-2-imino-6-methylhexahydropyrimidin-4-one Prepared as the TFA salt of a mixture of atropisomers from Intermediate 114 using General Method 3. LCMS (Method 3, ES+) 459.00 MH$^+$, 3.06 minutes.

Example 71

(6S)-6-{3-[2-(Benzylamino)-6-fluoro-7-(trifluoromethyl)benzimidazol-1-yl]-2-fluorophenyl}-2-imino-3,6-dimethylhexahydropyrimidin-4-one Prepared as the TFA salt of a mixture of atropisomers from Intermediate 151 using General Method 3. LCMS (Method 3, ES+) 543.00 MH$^+$, 3.41 minutes.

Example 72

5-Chloro-3-{2,6-difluoro-3-[(4S)-2-imino-1,4-dimethyl-6-oxohexahydropyrimidin-4-yl]-phenyl}-4-(trifluoromethyl)-1H-benzimidazol-2-one Prepared as the TFA salt of a mixture of atropisomers from Intermediate 150 using General Method 3. LCMS (Method 3, ES+) 488.00 MH$^+$, 3.16 and 3.18 minutes.

Example 73

(6S)-6-{3-[2-Cyclobutyl-6-fluoro-7-(trifluoromethyl)benzimidazol-1-yl]-2-fluorophenyl}-2-imino-3,6-dimethylhexahydropyrimidin-4-one Prepared as the TFA salt of a mixture of atropisomers from Intermediate 152 using General Method 3. LCMS (Method 3, ES+) 492.00 MH$^+$, 2.59 minutes.

Example 74

(6S)-6-[3-(6-Chloro-2-cyclobutylbenzimidazol-1-yl)-2-fluorophenyl]-2-imino-3,6-dimethylhexahydropyrimidin-4-one Prepared as the TFA salt of a mixture of atropisomers from Intermediate 153 using General Method 3. LCMS (Method 3, ES+) 440.00 MH$^+$, 2.87 minutes.

Example 75

(6S)-6-{3-[2-Cyclopropyl-6-fluoro-7-(trifluoromethyl)benzimidazol-1-yl]-2-fluorophenyl}-2-imino-3,6-dimethylhexahydropyrimidin-4-one Prepared as the TFA salt of a mixture of atropisomers from Intermediate 154 using General Method 3. LCMS (Method 3, ES+) 478.00 MH$^+$, 2.43 minutes.

Example 76

(6S)-6-{3-[2-Amino-6-fluoro-7-(trifluoromethyl)benzimidazol-1-yl]-2-fluorophenyl}-2-imino-3,6-dimethylhexahydropyrimidin-4-one A stirred solution of Intermediate 155 (0.10 g, 0.21 mmol) in methanolic NH$_3$ (5 mL) was heated at 90° C. for 16 h, then the reaction mixture was concentrated in vacuo. The crude residue was purified by preparative HPLC to afford the title compound (0.019 g, 20%, mixture of atropisomers) as an off-white solid. LCMS (Method 3, ES+) 453.00 MH$^+$, 1.71 and 1.79 minutes.

Example 77

(6S)-6-[3-(6-Chloro-2-methylbenzimidazol-1-yl)-2,4,6-trifluorophenyl]-2-imino-3,6-dimethylhexahydropyrimidin-4-one Prepared as the TFA salt of a mixture of atropisomers from Intermediate 117 using GeneralMethod 3. LCMS (Method 3, ES+) 436.00 MH$^+$, 3.09 minutes.

Example 78

(6S)-6-{3-[2-(Dimethylamino)-6-fluoro-7-(trifluoromethyl)benzimidazol-1-yl]-4-fluorophenyl}-2-imino-3,6-dimethylhexahydropyrimidin-4-one Prepared as the TFA salt of a mixture of atropisomers from Intermediate 158 using General Method 3. LCMS (Method 3, ES+) 481.00 MH$^+$, 2.46 minutes.

Example 79

(6S)-6-{3-[6-Chloro-2-(dimethylamino)benzimidazol-1-yl]-4-fluorophenyl}-2-imino-3,6-dimethylhexahydropyrimidin-4-one Prepared as the TFA salt of a mixture of atropisomers from Intermediate 161 using General Method 3. LCMS (Method 3, ES+) 429.00 MH$^+$, 1.67 and 1.69 minutes.

Example 80

(6)-6-{2-Chloro-3-[6-chloro-2-(pyrrolidin-1-yl)benzimidazol-1-yl]phenyl}-2-imino-3,6-dimethylhexahydropyrimidin-4-one Prepared as the TFA salt of a mixture of atropisomers from Intermediate 166 using General Method 3. LCMS (Method 3, ES+) 471.00 MH$^+$, 1.67 and 2.40 minutes.

Example 81

(6S)-6-{3-[6-Chloro-2-(morpholin-4-yl)benzimidazol-1-yl]-2-fluorophenyl}-2-imino-3,6-dimethylhexahydropyrimidin-4-one To a solution of Intermediate 145 (0.30 g, 0.71 mmol) in propan-2-ol (10 mL) was added morpholine (0.62 g, 7.14 mmol). The reaction mixture was heated at 110° C. for 16 h, then concentrated in vacuo. The crude residue was purified by preparative HPLC to afford the title compound (0.024 g, 7%, mixture of atropisomers) as an off-white solid. LCMS (Method 3, ES+) 471.00 MH$^+$, 2.20 minutes.

Example 82

(6S)-6-{3-[6-Chloro-2-(pyrrolidin-1-yl)benzimidazol-1-yl]-2-fluorophenyl}-3-(2-hydroxyethyl)-2-imino-6-methylhexahydropyrimidin-4-one Prepared as the TFA salt of a mixture of atropisomers from Intermediate 167 using General Method 3. LCMS (Method 3, ES+) 485.00 MH$^+$, 2.33 minutes.

The invention claimed is:

1. A compound represented by formula (IIA), or a pharmaceutically acceptable salt thereof:

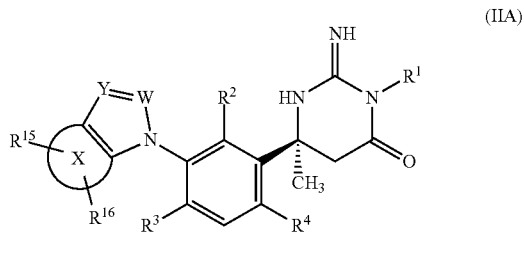

(IIA)

wherein
R$^1$ represents hydrogen; or R$^1$ represents C$_{1-6}$ alkyl, optionally substituted by hydroxy;
R$^2$, R$^3$ and R$^4$ independently represent hydrogen or halogen;
ring X represents a benzene or pyridine ring;
W represents N or C—R$^{13-}$;
Y represents N or C—R$^{14-}$;
R$^{13}$ represents hydrogen, methyl, ethyl, cyclopropyl, cyclobutyl, pyrrolidinyl, morpholinyl, hydroxymethyl, hydroxyisopropyl, methoxy, amino, methylamino, dimethylamino or benzylamino;
R$^{14}$ represents hydrogen, cyano or C$_{1-4}$ alkyl;
R$^{15}$ and R$^{16}$ independently represent hydrogen, halogen, cyano, nitro, C$_{1-6}$ alkyl, difluoromethyl, trifluoromethyl, methylpyrazolyl, hydroxy, hydroxy(C$_{1-6}$)alkyl, C$_{1-6}$ alkoxy, difluoromethoxy, trifluoromethoxy, C$_{1-6}$ alkylthio, C$_{1-6}$ alkylsulfinyl, C$_{1-6}$alkylsulfonyl, amino, C$_{1-6}$ alkylamino, di(C$_{1-6}$)alkylamino, di(C$_{1-6}$)alkylamino(C$_{1-6}$)alkyl, C$_{2-6}$ alkylcarbonylamino, C$_{2-6}$ alkoxycarbonylamino, C$_{1-6}$ alkylsulfonylamino, formyl, C$_{2-6}$ alkylcarbonyl, carboxy, C$_{2-6}$ alkoxycarbonyl, aminocarbonyl, C$_{1-6}$ alkylamino-carbonyl, di(C$_{1-6}$)alkylaminocarbonyl, aminosulfonyl, C$_{1-6}$ alkylaminosulfonyl or di(C$_{1-6}$) alkylaminosulfonyl.

2. A compound as claimed in claim 1 represented by formula (IIA-1a), or a pharmaceutically acceptable salt thereof:

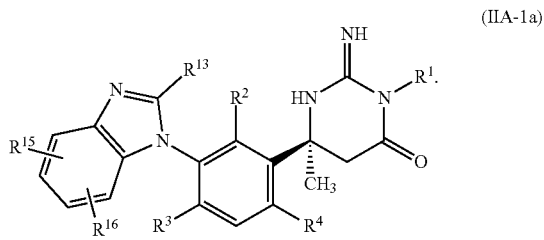

(IIA-1a)

3. A pharmaceutical composition comprising a compound of formula (IIA) as defined in claim 1 or a pharmaceutically acceptable salt thereof and a pharmaceutically acceptable carrier.

4. A method for the treatment of malaria, which comprises administering to a patient in need of such treatment an effective amount of a compound of formula (IIA) as defined in claim 1 or a pharmaceutically acceptable salt thereof.

5. A compound as claimed in claim 1 wherein R$^1$ represents hydrogen, methyl, ethyl or 2-hydroxyethyl.

6. A compound as claimed in claim 2 wherein R$^1$ represents hydrogen, methyl, ethyl or 2-hydroxyethyl.

7. A compound according to claim 1, wherein the compound is of formula (IIA-1b)

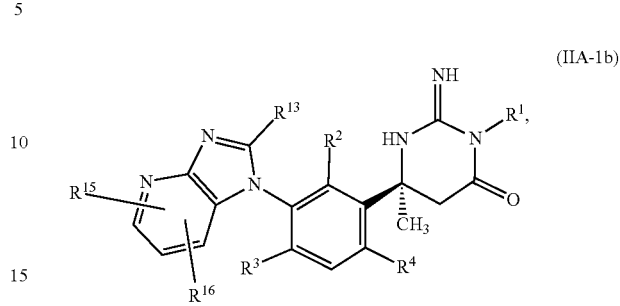

(IIA-1b)

or a pharmaceutically acceptable salt thereof.

8. A compound according to claim 1, wherein the compound is of formula (IIA-1c)

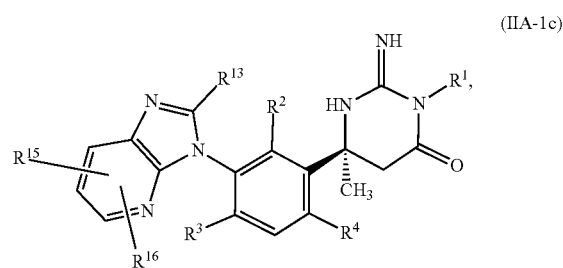

(IIA-1c)

or a pharmaceutically acceptable salt thereof.

9. A compound according to claim 1, wherein the compound is of formula (IIA-2a)

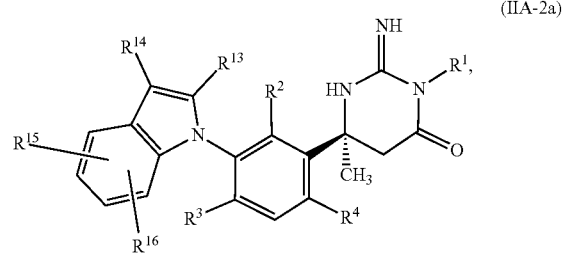

(IIA-2a)

or a pharmaceutically acceptable salt thereof.

10. A compound according to claim 1, wherein the compound is of formula (IIA-3a)

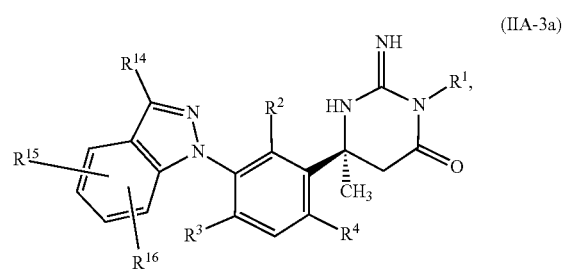

(IIA-3a)

or a pharmaceutically acceptable salt thereof.

* * * * *